US007439420B2

(12) United States Patent
Falco et al.

(10) Patent No.: US 7,439,420 B2
(45) Date of Patent: Oct. 21, 2008

(54) PLANT AMINO ACID BIOSYNTHETIC ENZYMES

(75) Inventors: Saverio Carl Falco, Arden, DE (US); Stephen M. Allen, Wilmington, DE (US)

(73) Assignee: E.I. duPont Nemours and Company, Wilmington, DE (US)

(*) Notice: Subject to any disclaimer, the term of this patent is extended or adjusted under 35 U.S.C. 154(b) by 155 days.

(21) Appl. No.: 11/501,425

(22) Filed: Aug. 9, 2006

(65) Prior Publication Data

US 2006/0277624 A1 Dec. 7, 2006

Related U.S. Application Data

(63) Continuation of application No. 09/931,457, filed on Aug. 16, 2001, now abandoned, which is a continuation-in-part of application No. 09/424,976, filed as application No. PCT/US98/12073 on Jun. 11, 1998, now abandoned.

(60) Provisional application No. 60/049,406, filed on Jun. 12, 1997, provisional application No. 60/065,385, filed on Nov. 12, 1997.

(51) Int. Cl.

| | |
|---|---|
| *C12N 15/29* | (2006.01) |
| *C12N 15/52* | (2006.01) |
| *C12N 15/82* | (2006.01) |
| *A01H 5/00* | (2006.01) |
| *A01H 5/10* | (2006.01) |

(52) U.S. Cl. ....................... 800/298; 800/287; 800/278; 536/23.1; 536/23.6; 536/24.1; 435/320.1; 435/419; 435/468

(58) Field of Classification Search ....................... None
See application file for complete search history.

(56) References Cited

OTHER PUBLICATIONS

Noji, M. et al. Mol. Gen. Gen. 244:57-66; 1994.*

Saito K. et al.; FEBS Lett. 324:247-252 1993.*

National Center for Biotechnology Information General Identifer No. 14595120, Jul. 5, 2001, Kaneko, T. et. al., Sequence Analysis of the Genome of the Unicellular Cyanobacterium Synechocystics Sp. Strain PCC6803. II. Sequence Determination of the Entire Genome and Assignment of Potential Protein-Coding Regions.

Takakazu Kaneko et al., DNA Research, vol. 2:153-166, 1995, Sequence Analysis of the Genome of the Unicellular Cyanobacterium Synechocystis SP. Strain PCC6803. I. Sequence Features in the 1 MB Region From Map Positions 64% to 92% of the Genome.

Takakazu Kaneko et al., DNA Research, vol. 3:109-136, 1996, Sequence Analysis of the Genome of the Unicellular Cyanobacterium Synechocystis SP. Strain PCC6803. II. Sequence Determination of the Entire Genome and Assignment of Potential Protein-Coding Region.

National Center for Biotechnology Information General Identifier No. 1001379, Jul. 5, 2001, Kanekao, T. et. al., Sequence Analysis of the Genome of the Unicellular Cyanobacterium Synechocystis SP. Strain PCC6803. I. Sequence Features in the 1 MB Region From Map Positions 64% to 92% of the genome.

National Center for Biotechnology Information General Identifier No. 2645881, May 1, 1998, Harb, O. S. et. al., Identification of the Aspartate-Beta-Semialdehyde Dehydrogenase Gene of Legionella Pneumophila and Characterization of a Null Mutant.

Omar S. Harb et. al., Infection and Immunity, vol. 66: 1898-1903, 1998, Identification of the Aspartate-B-Semialdehyde Dehydorgenase Gene of Legionella Pneumophila and Characterization of a Null Mutant.

Natiional Center for Biotechnology Information General Identifer No. 2645882, May 1, 1998, Harb, O. S. et. al., Identification of the Aspartate-Semialdehyde Dehydrogenase Gene of Legionella Pneumophila and Characterization of a Null Mutant.

National Center for Biotechnology Information General Identifer No. 6225258, Aug. 20, 2001, Deckert, G. et. al., The Complete Genome of the Hyperthermophilic Bacterium Aquifex Aeolicus.

National Center for Biotechnology Information General Identifer No. 2983641, Mar. 25, 1998, Deckert, G. et. al., The Complete Genome of the Hyperthermophilic Bacterium Aquifex Aeolicus.

National Center for Biotechnology Information General Identifer No. 2983642, Mar. 25, 1998, Deckert, G. et. al., The Complete Genome of the Hyperthermophilic Bacterium Aquifex Aeolicus.

National Center for Biotechnology Information General Identifer No. 340818, Aug. 4, 1993, Martin, C. et. al., Pseudomonas Aeruginosa Diaminopimelate Decarboxylase: Evolutionary Relationship With Other Amino Acid Decarboxylases.

National Center for Biotechnology Information General Identifer No. 118304, Jul. 1, 1993, Martin, C. et. al., Pseudomonas Aeruginosa Diaminopimelate Decarboxylase: Evolutionary Relationship With Other Amino Acid Decarboxylases.

National Center for Biotechnology Information General Identifer No. 1929092, Jun. 28, 1998, Dekkers, L. C. et. al., A Site-Specific Recombinase is Required for Competitive Root Colonization by Pseudomonas Fluorescens WCS365.

National Center for Biotechnology Information General Identifer No. 1929095, Jun. 28, 1998, Dekkers, L. C. et. al., A Site-Specific Recombinase is Required for Competitive Root Colonization by Pseudomonas Fluorescens WCS365.

National Center for Biotechnology Information General Identifer No. 6225241, Aug. 20, 2001, Dekkert, G. et. al., The Complete Genome of the Hyperthermophilic Bacterium Aquifex Aeolicus.

National Center for Biotechnology Information General Identifer No. 9279586, Dec. 27, 2000, Sato, S. et. al., Structural Analysis of Arabidopsis Thaliana Chromosome 3. I. Sequence Features of the Regions of 4,504,864 BP Covered by Sixty P1 and TAC Clones.

National Center for Biotechnology Information General Indetifier No. 1591744, Jan. 28, 1998, Bult, C. J., et. al., Complete Genome Sequence of the Methanogenic Archaeon, Methanococcus Jannaschii.

(Continued)

*Primary Examiner*—Russell Kallis

(57) ABSTRACT

This invention relates to an isolated nucleic acid fragment encoding a plant cysteine γ synthase. The invention also relates to the construction of a chimeric gene encoding all or a portion of the plant cysteine γ synthase, in sense or antisense orientation, wherein expression of the chimeric gene results in production of altered levels of the plant biosynthetic enzyme in a transformed host cell.

14 Claims, 20 Drawing Sheets

OTHER PUBLICATIONS

Figure 1:
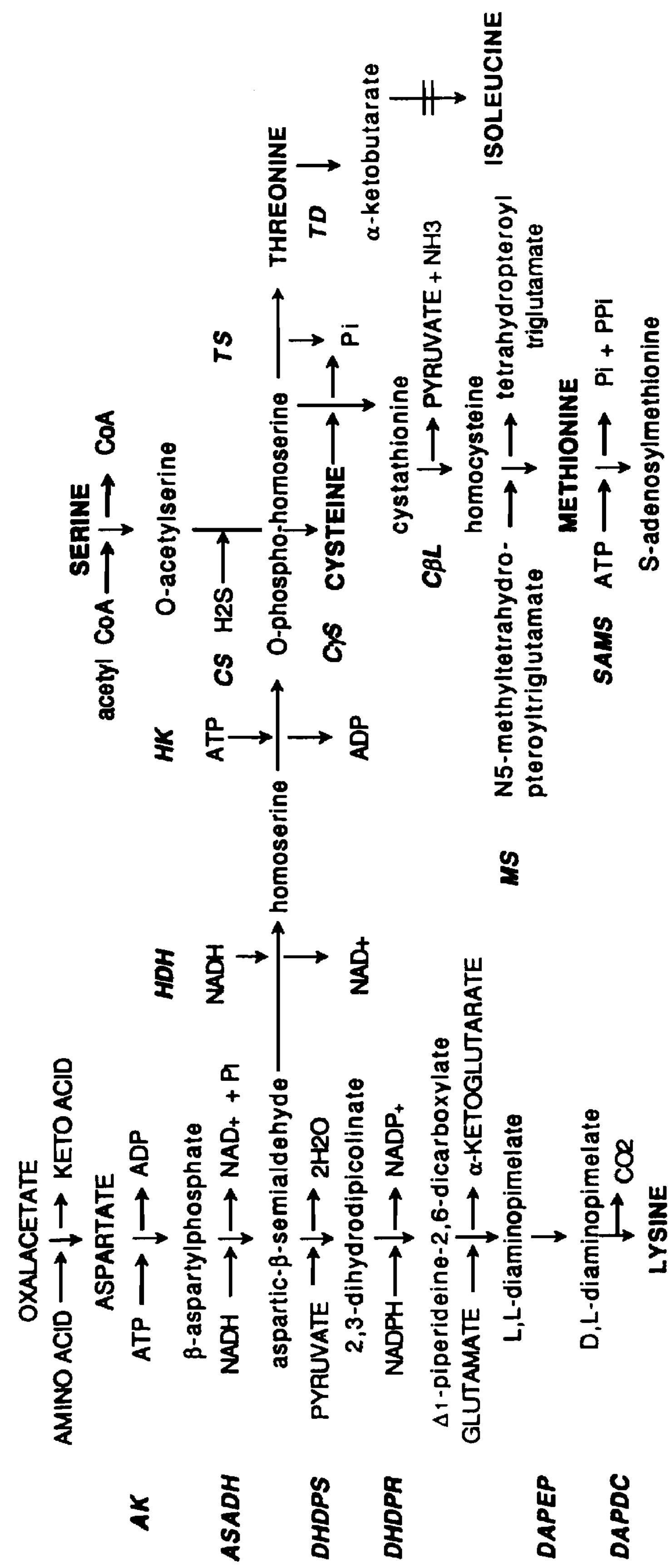

National Center for Biotechnology Information General Indetifier No. 1591748, Jan. 28, 1998, Bult, C. J. et. al., Complete Genome Sequence of the Methanogenic Archaeon, Methanococcus Jannaschii.

National Center for Biotechnology Information General Indetifier No. 4927412, Feb. 29, 2000, Lee, M. et. al., Identification of the Gene Encoding Homoserine Kinase From Arabidopsis Thaliana and Characterization of the Recombinant Enzyme Derived From the Gene.

National Center for Biotechnology Information General Indetifier No. 466530, Feb. 7, 1999, Noji, M. et. al. Molecular Cloning of a Cysteine Synthase CDNA From *Citrullus vulgaris* (Watermelon) by Genetic Complementation in an *Escherichia coli*-CYS-Auxotroph.

National Center for Biotechnology Information General Indetifier No. 540497, Feb. 7, 1999, Noji, M. et. al. Molecular Cloning of a Cysteine Synthase CDNA From *Citrullus vulgaris* (Watermelon) by Genetic Complementation in an *Escherichia coli*-CYS-Auxotroph.

National Center for Biotechnology Information General Indetifier No. 416869, May 30, 2000, Saito, K. et. al., CDNA Cloning and Expression of Cysteine Synthase B Localized In Chloroplasts of Spinacia Oleracae.

National Center for Biotechnology Information General Indetifier No. 11131628, Aug. 20, 2001, Hesse, H. et. al., Isolation of CDNAS Encoding Cytosolic and Plastidic Cysteine Synthase Isoforms From Solanum Tubersum.

National Center for Biotechnology Information General Indetifier No. 704396, May 9, 1996, Ravenel, S. et. al., Cloning of an Arabidopsis Thaliana CDNA Encoding Cystathionine Beta-Lyase by Functional Complementation in *Escherichia coli*.

National Center for Biotechnology Information General Indetifier No. 1708993, Aug. 20, 2001, Ravanel, S. et. al. Cloning of an Arabidopsis Thaliana CDNA Encoding Cystathionine Beta-Lyase by Functional Complementation in *Escherichia coli*.

* cited by examiner

Figure 2A

```
                                                                 *  **  *****++**  *
SEQ ID NO: 7   MS--------RHL-----------------------------NVAIVGATGAVGETFLTV
SEQ ID NO:52   MG----------Y-----------------------------RVAIVGATGEVGRTFLKV
SEQ ID NO:43   ------------------------------------------------------------
SEQ ID NO: 2   ------------------------------------------------------------
SEQ ID NO:45   MQAAAAAVHRPHLLGAYPGGGRARRPSST---VRMALREDGPSVAIVGATGAVGQEFLRV
SEQ ID NO: 6   -MASLSVLRHNHLFSG-PLPARPKPTSSSSSRIRMSLRENGPSIAVVGVTGAVGQEFLSV
SEQ ID NO:49   -MASLSVLRHNHLFSG-PLPARPKPTSSSSSRIRMSLRENGPSIAVVGVTGAVGQEFLSV
SEQ ID NO:47   ARASLSVLRHNHLFSG-PLPARPKPTSSSSSRIRMSLRENGPSIAVVGVTGAVGQEFLSV
SEQ ID NO: 4   ------------------------------------------------------------
SEQ ID NO:51   MQAAAA-VHRPHLLAASPLGGRASRRPST---VRMALREDGPSVAIVGATGAVGQEFLRV
               1                                                          60

                  *  **++*   ***  **+*  +   *+    *  *+  *   +   *+***********   *
SEQ ID NO: 7   LEERNFPIKSLYPLASSRSVGKTVTFRDQELDVLDLA-EFDFSKVDLALFSAGGAVSKEY
SEQ ID NO:52   LEERNFPVDELVLYASERSEGKVLTFKGKEYTVKALNKENSFKGIDIALFSAGGSTSKEW
SEQ ID NO:43   -------------------------------AVQDLAAPGAFDGVDIALFSAGGSVSRKY
SEQ ID NO: 2   ------------------------------------------------------------
SEQ ID NO:45   ISSRGFPYRSLRLLASERSAGKRLPFEGQEYTVQDLAAPGAFDGVDIALFSAGGGVSRAH
SEQ ID NO: 6   LSDRDFPYRSIHMLASKRSAGRRITFED--------------------------------
SEQ ID NO:49   LSDRDFPYRSIHMLASKRSAGRRITFEDRDYVVQELT-PESFDGVDIALFSAGGSISKHF
SEQ ID NO:47   LSDRDFPYRSIHMLASKRSAGRRITFEDRDYVVQELT-PESFDGVDIALFSAGGSISKHF
SEQ ID NO: 4   ------------------------------------------------------------
SEQ ID NO:51   ITARDFPYRSLRLLASERSAGKRIDFEGRDYTVQDLAAPGAFDGVDIALFSAGGSISRAH
              61                                                          120
```

Figure 2B

```
                * **  * ******** **   ****+******++         ++  ******** ++
SEQ ID NO: 7   APKAVAAGCVVVDNTSCFRYEDDIPLVVPGSESSSNRDYT----KRGIIANPNCSTIQMV
SEQ ID NO:52   APKFAKDGVVVIDNSSAWRMDPDVPLVVPEVNPEDVKDFK----KKGIIANPNCSTIQMV
SEQ ID NO:43   GPAAVASGAVVVDNSSAFRMEPEVPLVIPEVNPEAMANVRLG--QGAIVANPNCSTIICL
SEQ ID NO: 2   ------------------------------------------------------------
SEQ ID NO:45   APAAVASGAVVVDNSSAFRMDPEVPLVIPEVNPEAMAHVRLG--KGAIVANPNCSTIICL
SEQ ID NO: 6   ------------------------------------------------------------
SEQ ID NO:49   GPIAVNRGTVVVDNSSAFRMDEKVPLVIPEVNPEAMQNIKAGTGKGALIANPNCSTIRCL
SEQ ID NO:47   GPIAVNRGTVVVDNSSAFRMNEKVPLVIPEVNPEAMQNIKAGTGKGALIANPNCSTIICL
SEQ ID NO: 4   -----------------------------------------------------------L
SEQ ID NO:51   APAAVASGAVVVDNSSAYRMDPDVPLVIPEVNPEAMADVRLG--KGAIVANPNCSTIICL
             121                                                          180

               +*++*  + *++ *+*******+*****+*+*** +** ++****  *++ +*  *+***
SEQ ID NO: 7   VALKPIYDAVGISRINVATYQSVSGTGKKAISELVAQVGDLLNGRP-ANVQVYPQQIAFN
SEQ ID NO:52   VALKPIYDKAGIKRVVVSTYQAVSGAGAKAIEDLKNQTKAWCEGKEMPKAQKFPHQIAFN
SEQ ID NO:43   MAATPLHRHAKVLRMVVSTYQAASGAGAAAMEELKLQTQEVLEGKA-PTCNIFKQQYAFN
SEQ ID NO: 2   -----WYRHAKVVRMVVSTYQAASGAGAAAMEELKLQTQEVLAGKA-PTCNIFSQQYAFN
SEQ ID NO:45   MAATPLHRHAKVVRMVVSTYQAASGAGAAAMEELKLQTQEVLAGKA-PTCNIFSQQYAFN
SEQ ID NO: 6   MAVTPLHRHAKVKRMVVSTYQAASGAGAAAMEELKLQTREVLEGKP-PTCNIFSQQYAFN
SEQ ID NO:49   KAATPLHRRAKVLRMVVSTYQAASGAGAAAMEELELQTREVLEGKP-PTCKIFNRQYAFN
SEQ ID NO:47   MAATPLHRRAKVLRMVVSTYQAASGAGAAAMEELELQTREVLEGKP-PTCKIFNRQYAFN
SEQ ID NO: 4   ------------------------------------------------------------
SEQ ID NO:51   MAVTPLHRHAKVKRMVVSTYQAASGAGAAAMEELKLQTREVLEGKP-PTCNIFSQQYAFN
             181                                                          240
```

Figure 2C

```
               ++*+++    ***++******+*****++*+ + *+***+*** +++++***+*++* **
SEQ ID NO: 7   ALPHIDQFEDNGYTREEMKMVWETRKIMEDDSIMVNPTAVRVPVIYGHSEAVHLELKKPL
SEQ ID NO:52   ALPHIDVFFEDGYTKEENKMLYETRKIMHDENIKVSATCVRIPVFYGHSESISMETEKEI
SEQ ID NO:43   IFSHNAPVLENGYNEEEMKMVKETRKIWNDKEVKVTATCIRVPVMRAHAESVNLQFEKPL
SEQ ID NO: 2   IFSHNAPIVENGYNEEEMKMVKETRKIWNDKDVKVTATCIRVPVMRAHAESVNLQFEKPL
SEQ ID NO:45   IFSHNAPIVENGYNEEEMKMVKETRKIWNDKDVKVTATCIRVPVMRAHAESVNLQFEKPL
SEQ ID NO: 6   ------------------------------------------------------------
SEQ ID NO:49   LFSHNASVLSNGYNEEEMKMVKETRKIWNDKDVKVTATCIRVPIMRAHAESVNLQFERPL
SEQ ID NO:47   LFSHNASVLSNGYNEEEMKMVKETRKIWNDKDVKVTATCIRVPIMRAHAESVNLQFERPL
SEQ ID NO: 4   IFSHNAPIVENGYNEEEMKMVKETRKIWNDKDVRVTATCIRVPTMRAHAESVNLQFEKPL
SEQ ID NO:51   IFSHNAPIVENGYNEEEMKMVKETRKIWNDKDVRVTATCIRVPTMRAHAESVNLQFEKPL
             241                                                          300

               ++*+** +*  ****   *++  * +***+ +++ +*** *******+* + + **  +*
SEQ ID NO: 7   TADDARALLAKAPGVTVVDNLSKASYPTAIKNAVGHDDVFVGRIRQDISHPC--GLNLWI
SEQ ID NO:52   SPEEAREVLKNAPGVIVIDNPQNNEYPMPIM-AEGRDEVFVGRIRKDRVFEP--GLSMWV
SEQ ID NO:43   DEDTAREILRAAPGVTIIDDRASNRFPTPL-EVSDKDDVAVGRIRQDLSLDGNRGLDIFV
SEQ ID NO: 2   DEDTAREILRAAEGVTIIDDRASNRFPTPL-EVSDKDDVAVGRIRQDLSQDDNKGLDIFV
SEQ ID NO:45   DEDTAREILRAAEGVTIIDDRASNRFPTPL-EVSDKDDVAVGRIRQDLSQDDNKGLDIFV
SEQ ID NO: 6   ------------------------------------------------------------
SEQ ID NO:49   DEDTARDILKNAPGVVVIDDRESNHFPTPL-EVSNKDDVAVGRIRQDLSQDGNQGLDIFV
SEQ ID NO:47   DEDTARDILKNAPGVVVIDDRESNHFPTPL-EVSNKDDVAVGRIRQDLSQDGNQGLDIFV
SEQ ID NO: 4   DEDTAREILRAAPGVTISDDRAANRFPTPL-EVSDKDDVSVGRIRQDLSQDDNRGLELFV
SEQ ID NO:51   DEDTAREILRAAPGVTISDDRAANRFPTPL-EVSDKDDVSVGRIRQDLSQDDNRGLELFV
             301                                                          360
```

Figure 2D

```
                  ++*+******+** ****+*         *
SEQ ID NO: 7      VADNIRKGAATNAVQIAEILQREFLLKLSLPQ
SEQ ID NO:52      VADNIRKGAATNAVQIAELLVKEGLI------
SEQ ID NO:43      CGDQIRKGAALNAVQIAEML---------LK-
SEQ ID NO: 2      CGDQIRKGAALNAVQIAEML---------LK-
SEQ ID NO:45      CGDQIRKGAALNAVQIAEML---------LK-
SEQ ID NO: 6      --------------------------------
SEQ ID NO:49      CGDQIRKGAALNAIQIAEML---------L--
SEQ ID NO:47      CGDQIRKGAALNAIQIAEML---------L--
SEQ ID NO: 4      CGDQIRKGAALNAVQIAEML---------LK-
SEQ ID NO:51      CGDQIRKGAALNAVQIAEML---------LK-
                361                             392
```

Figure 3A

```
SEQ ID NO:20  MD-----------------------------TFSYRDAE---------------------
SEQ ID NO:57  MGQTNSETQQARLYTQNSQKQLLRSFLLLHLIFGYQSHKTLRMAAATQFLSQPSSLNPHQ
SEQ ID NO: 9  ------------------------------------------------------------
SEQ ID NO:11  M---------------AAANLLSRSLL--------PTPNTIRTSHPTPRSPAV-------
SEQ ID NO:13  L---------------H-------------------------------------------
SEQ ID NO:15  ------------------------------------------------------------
SEQ ID NO:19  ------------------------------------------------------------
SEQ ID NO:54  C---------------NTHCLVGKIFH--------QQHTAMAGSNILSHSPSLPKTYSHS
SEQ ID NO:17  ------------------------------------------------------------
SEQ ID NO:56  ------------------------------------------------------------
              1                                                         60

              +                                               +++    ** *+
SEQ ID NO:20  ----------------------------------------------------------LF
SEQ ID NO:57  LKNQTSQRSRSIPVLSLKSTLKPLKRLSV--KAAVVSQNSSKTVTKFDHCFKKSSDGFLY
SEQ ID NO: 9  ------------------------------------------------------------
SEQ ID NO:11  --------------VSFPRRRARLSVCASVSMASPSPPPQPAAAGVPKHCFRRGADGYLY
SEQ ID NO:13  ------------------------------------------------------------
SEQ ID NO:15  ------------------------------------------------------------
SEQ ID NO:19  ------------------------------------------------------------
SEQ ID NO:54  LNQNALSQKLFFLPLKFKATTKPRALRAVLSQNAVKTSVEDTKNAHFQHCFTKSEDGYLY
SEQ ID NO:17  ------------------------------------------------------------
SEQ ID NO:56  ------------------------------------------------------------
              61                                                       120
```

Figure 3B

```
                   +**  + + +   ++ *+*+**+ +* ++  **  ** *  +  ++* ***+**  *  *
SEQ ID NO:20       AEGVALSRIAERFG-TPTYVYSRAHIEAQYRAYADALAGMPHLVCFAVKANSNLGVLNVL
SEQ ID NO:57       CEGTKVEDIMESVERRPFYLYSKPQITRNLEAYKEALEGVSSVIGYAIKANNNLKILEHL
SEQ ID NO: 9       ------------------------------------------------------------
SEQ ID NO:11       CEGVRVEDAMAAAERSPFYLYSKLQILRNFAAYRDALQGLRSIVGYAVKANNNLPVLRVL
SEQ ID NO:13       ------------------------------------------------------------
SEQ ID NO:15       ------------------------------------------------------------
SEQ ID NO:19       --------------RRPFYLYSKPQITRNVEAYKDALEGLNSIIGYAIKANNNLKILXHL
SEQ ID NO:54       CEGLKVHDIMESVERRPFYLYSKPQITRNVEAYKDALEGLNSIIGYAIKANNNLKILEHL
SEQ ID NO:17       ------------------------------------------------------------
SEQ ID NO:56       ------------------------------------------------------------
                   121                                                      180

                   + **+*+++**++** ++* **+**  ++*+*+** ++ + +*+  **+ +* +*+++*
SEQ ID NO:20       ARLGAGFDIVSRGELERVLAAGGDPAKVVFSGVGKTRDDMRRALEVGVHCFNVESGEELE
SEQ ID NO:57       RSLGCGAVLVSGNELRLALRAGFDPTKCIFNGNGKSLEDLVLAAQEGVF-VNVDSEFDLN
SEQ ID NO: 9       -----------------------------FNGNGKTLEHLKLAAESGVF-VNVDSEFDLE
SEQ ID NO:11       RELGCGAVLVSGNELRLALQAGFDPARCIFNGNGKTLEDLKLAAESGVF-VNVDSEFDLE
SEQ ID NO:13       ----------------------------------------------GVF-VNIDSEFDLE
SEQ ID NO:15       ------------------------------------------------------------
SEQ ID NO:19       RHLGCGAVLVSGNELK--------------------------------------------
SEQ ID NO:54       RHLGCGAVLVSGNELKLALRAGFDPTRCIFNGNGKILEDLVLAAQEGVF-VNIDSEFDLE
SEQ ID NO:17       ------------------------------------------------------------
SEQ ID NO:56       ------------------------------------------------------------
                   181                                                      240
```

Figure 3C

```
                   +++ +    *+ + *+**+*****+*+****++**+* +****++++++ ++    +
SEQ ID NO:20       RLQRVAAELGVKAPVSLRVNPDVDAQTHPYISTGLKENKFGIAIDEAEAVYARAAEL-DH
SEQ ID NO:57       NIVEASRISGKQVNVLLRINPDVDPQVHPYVATGNKNSKFGIRNEKLQWFLDQVKAHPKE
SEQ ID NO: 9       NIVRAARATGKKVPVLLRINPDVDPQVHPYVATGNKTSKFGIRNEKLQWFLDSIKSYPNE
SEQ ID NO:11       NIVRAARATGKKVPVLLRINPDVDPQVHPYVATGNKTSKFGIRNEKLQWFLNSIKSYSNE
SEQ ID NO:13       NIVTAARVAGKKVPVLLRINPDVDPQVHPYVATGNKTSKFGIRNEKLQWFLDSIKSYSND
SEQ ID NO:15       ------------------------------VATGNKNSKFGIRNEKLQCFLDAVKEHPNE
SEQ ID NO:19       ------------------------------------------------------------
SEQ ID NO:54       NIVEAAKRAGKKVNVLLRINPDVDPQVHPYVATGNKNSKFGIRNEKLQCFLDAVKEHPNE
SEQ ID NO:17       ------------------------------------------------------------
SEQ ID NO:56       ------------------------------------------------------------
                  241                                                         300

                     ++* +**+**++*++++*+**+   +   + * ++ +*+    +*++*****++* +  +
SEQ ID NO:20       LEVIGVDCHIGSQLTQLEPFLDALERLLGLVDRLAGKGIGIRHLDLGGGLGVRYRDEQPP
SEQ ID NO:57       LKLVGAHCHLGSTITKVDIFRDAAVLMIEYIDEIRRQGFEVSYLNIGGGLGIDYYHAGAV
SEQ ID NO: 9       IKLVGVHCHLGSTITKVDIFRDAAVLMLNYVDEIRAQGFKLEYLNIGGGLGIDYHHTDAV
SEQ ID NO:11       IKLVGVHCHLGSTITKVDIFRDAAVLMVNYVDEIRAQGFKLEYLNIGGGLGIDYHHTDAV
SEQ ID NO:13       ITLVGVHCHLGSTITKVDIFRDAAGLMVNYVDEIRAQGFELEYLNIGGGLGIXYHHTDAV
SEQ ID NO:15       LKLVGAHCHLGSTITKVDIFRDAATIMINYIDQIRDQGFEVDYLNIGGGLGIDYYHSGAI
SEQ ID NO:19       ------------------------------------------------------------
SEQ ID NO:54       LKLVGAHCHLGSTITKVDIFRDAATIMINYIDQIRDQGFEVDYLNIGGGLGIDYYHSGAI
SEQ ID NO:17       ------------------------------------------------------------
SEQ ID NO:56       --------------------------------------FELEYLNIGGGLGIDYHHTGAV
                  301                                                         360
```

Figure 3D

```
                   *+++              ++ +  * *++*****++**+++ +++*+++* ++ *+*++ *++*
SEQ ID NO:20   LA---GDYIRAIRERLHGRDLTLVFEPGRSIVANAGVLLTRVEYLKHTEHKDFAIVDAAM
SEQ ID NO:57   LPTPMD-LINTVRELVLSRDLNLIIEPGRSLIANTCCFVNHVTGVKTNGTKNFIVIDGSM
SEQ ID NO: 9   LPTPMD-LINTVRELVLSQDLTLIIEPGRSLIANTCCFVNRVTGVKSNGTKNFIVVDGSM
SEQ ID NO:11   LPTPMD-LINTVRELVLSQDLTLIIEPGRSLIANTCCFVNRVTGVKSNGTKNFIVVDGSM
SEQ ID NO:13   LPTPMGPHQHCAEELVLSRDLTLIIEPGRSLIANTCCFVNRVTGVKSNGTKNFIVVDGSM
SEQ ID NO:15   LPTPRD-LIDTVRDLVISRGLNLIIEPGRSLIANTCCLVNRVTGVKTNGSKNFIVIDGSM
SEQ ID NO:19   ------------------------------------------------------------
SEQ ID NO:54   LPTPRD-LIDTVRDLVISRGLNLIIEPGRSLIANTCCLVNRVTGVKTNGSKNFIVIDGSM
SEQ ID NO:17   -PTPMD-LINTVRELVLSRDLTLIIEPGRSLIANTCCFVNKVTGVKSNGTKNFIVVDGSM
SEQ ID NO:56   LPTPMD-LINTVRELVLSRDLTLIIEPGRSLIANTCCFVNKVTGVKSNGTKNFIVVDGSM
              361                                                         420

               ++*****+** *+++++***      +    +* ******++***+* *+*+++  * +*+*
SEQ ID NO:20   NDLIRPALYQAWMDVQAVRPRDAAPR--RYDLVGPICETGDFLAKDRDLALAE-GDLLAV
SEQ ID NO:57   AELIRPSLYDAYQHIELVSPPPAEAEVTKFDVVGPVCESADFLGKDRELPTPPQGAGLVV
SEQ ID NO: 9   AELIRPSLYGAYQHIELVSPPTPGAEAATFDIVGPVCESADFLGKDRELPTPDEGAGLVV
SEQ ID NO:11   AELIRPSLYGAYQHIELVSPPTPGAEVATFDIVGPVCESADFLGKDRELPTPDEGAGLVV
SEQ ID NO:13   AELIRPSLYGAYQHIELVSPS-PDAEVATFDIVGPVCESADFLGKDRELPTPDKGAGLVV
SEQ ID NO:15   AELIRPSLYDAYQHIELVSPAPSNAETETFDVVGPVCESADFLGKGRELPTPAKGTGLVV
SEQ ID NO:19   ------------------------------------------------------------
SEQ ID NO:54   AELIRPSLYDAYQHIELVSPAPSNAETETFDVVGPVCESADFLGKGRELPTPAKGTGLVV
SEQ ID NO:17   AELIRPSLYGAYQHI---------------------------------------------
SEQ ID NO:56   AELIRPSLYGAYQHIELVSPS-PGAEVATFDIVGPVCESADFLGKDRELPTPDKGAGLVV
              421                                                         480
```

Figure 3E

```
               ++****+++*+*+**++ *+ *++*+ +++  ++*+ *   +   ++     *
SEQ ID NO:20   RSAGAYGFVMSSNYNTRGRAAEVLVDGQQT-HEVRRRETVEE---LYAGESLLPQ
SEQ ID NO:57   HDAGAYCMSMASTYNLKMRPPEYWVEEDGSITKIRHAETFDDHLRFFEG---L--
SEQ ID NO: 9   HDAGAYCMSMASTYNLKLRPPEYWVEADGSIVKIRHGEKLDDYMKFFDG---LPA
SEQ ID NO:11   HDAGAYCMSMASTYNLKLRPPEYWVEEDGSIVKIRHEEKLDDYMKFFDG---LPA
SEQ ID NO:13   HDAGAYCMSMASTYNLKLRPPEYWVEDDGSIAKIRRGESFDDYMKFFDN---LSA
SEQ ID NO:15   HDAGAYCMSMASTYNLKMRPPEYWVEDDGSVSKIRHGETFEDHIRFFEG---L--
SEQ ID NO:19   -------------------------------------------------------
SEQ ID NO:54   HDAGAYCMSMASTYNLKMRPPEYWVEDDGSVSKIRHGETFEDHIRFFEG---L--
SEQ ID NO:17   -------------------------------------------------------
SEQ ID NO:56   HDAGAYCMSMASTYNLKMRPAEYWVEDDGSIVKIRHGETFDDYMKFFDG---LPA
              481                                                     535
```

Figure 4A

```
                                                                      *
SEQ ID NO:60  MA-SLCFQSPSKPISYFQPKSNPSPPLFAKVSVFRCRASVQTLVAVEPEPVFVSVKTFAP
SEQ ID NO:29  M----------------------------------------------REIMKVRVKA--P
SEQ ID NO:22  ------------------------------------------------------------
SEQ ID NO:24  ------------------------------------------------------------
SEQ ID NO:59  ------------------------------------------------------------
SEQ ID NO:26  MATSTCFLCPSTA-------SLKGRARF-RIRI-RCSSSVSVNIRREPEPVTTLVKAFAP
SEQ ID NO:28  ------------------------------------------------------------
              1                                                         60

              +*+****+***++* *++++* +   + +++ +  +*+ *+ + +    +++ +*+ *++
SEQ ID NO:60  ATVANLGPGFDFLG-CAVDGLGDHVTLRVDPSVRAGEVSISEITG-TTTKLSTNPLRNCA
SEQ ID NO:29  CTSANLGVGFDVFGLC----LKEPYDVIEVEAIDDKEIII-EVDD---KNIPTDPDKNVA
SEQ ID NO:22  ------------------------------------------------------------
SEQ ID NO:24  ------------------------------------------------------------
SEQ ID NO:59  -----------------------------------------------------------H
SEQ ID NO:26  ATVANLGPGFDFLG-CAVDGLGDIVSVKVDPQVHPGEICISDISGHAPNKLSKNPLWNCA
SEQ ID NO:28  ------------------------------------------------------------
             61                                                          120

                +*+     +   +   +  + **+++**********+*++* *+  +*+  *    *+
SEQ ID NO:60  GIAAIATMKMLGIRSVGLSLDLHKGLPLGSGLGSSAASAAAAAVAVNEIFGRKLGSDQLV
SEQ ID NO:29  GIVAKKMIDDFNI-GKGVKITIKKGVKAGSGLGSSAASSAGTAYAINELF--KLNLDKLK
SEQ ID NO:22  ------------------------------------------------------------
SEQ ID NO:24  -----------------VSIHLTKGLPLGSGLGSSAASAAAAAKAVDALFGSLLHQDDLV
SEQ ID NO:59  EVAAIAALRALDVKSHAVSIHLTKGLPLGSGLGSSAASAAAAAKAVDALFGSLLHQDDLV
SEQ ID NO:26  GIAAIEVMKMLSIRSVGLSLSLEKGLPLGSGLGSSAASAAAAAVAVNELFGKKLSVEELV
SEQ ID NO:28  ------------------------------------------------------------
             121                                                         180
```

Figure 4B

```
                *+ + *  *  +*   **** ** * ***++   * *  + +*  *    * + +  * +
SEQ ID NO:60    LAGLES--EAKVS-GYHADNIAPAIMGGFVLIRNYEPLDLKPLKFPSDKDLFFVLVSPEF
SEQ ID NO:29    LVDYASYGELASSGAKHADNVAPAIFGGFTMVTNYEPLEV--LHIPIDFKLDILIAIPNI
SEQ ID NO:22    ------------------DNIAPAILGGFVLVRSYDPFHLVPLSFPPALRLHFVLVTPDF
SEQ ID NO:24    LAGLES--EKAVSGXXHADNIAPAILGGFVLVRSYDP---------------FHLI----
SEQ ID NO:59    LAGLES--EKAVSG-FHADNIAPAILGGFVLVRSYDPFHLIPLSSPPALRLHFVLVTPDF
SEQ ID NO:26    LASLKS--EEKVSG-YHADNVAPSIMGGFVLIGSYSPLELMPLKFPAEKELYFVLVTPEF
SEQ ID NO:28    ---LES--EKAVSG-FHADNIAPAILGGFVLVRSYDPFHLVPLSFPPALRLHFVLVTPDF
              181                                                           240
                +++* ++*++**       +* * ++* ++*+*++ +*    * + +** ++**+*++**
SEQ ID NO:60    EAPTKKMRAALPTEIPMVHHVWNSSQAAALVAAVLEGDAVMLGKALSSDKIVEPTRAPLI
SEQ ID NO:29    SINTKEAREILPKAVGLKDLVNNVGKACGMVYALYNKDKSLFGRYMMSDKVIEPVRGKLI
SEQ ID NO:22    EAPTSKMRAALPRQVDVQQHVRNSSQAAALVAAVLQGDAGLIGSAMSSDGIVEPTRAPLI
SEQ ID NO:24    ------------------------------------------------------------
SEQ ID NO:59    EAPTSKMRAALPKQVAVHQHVRNSSQAAALVAAVLQGDATLIGSAMSSDGIVEPTRAPLI
SEQ ID NO:26    EAPTKKMRAALPTEIGMPHHVWNCSQAGALVASVLQGDVVGLGKALSSDKIVEPRRAPLI
SEQ ID NO:28    EAPTSKMRAALPRQVDVQQHVRNSSQAAAL------------------------------
              241                                                           300

                *++ ++* ++  +++ *+****+**+ +*++  +  +      +  ++   + ++  + +
SEQ ID NO:60    PGMEAVKKAALEAGAFGCTISGAGPTAVAVIDSEEKGQVIGEKMVEAFWKVGHLKSVASV
SEQ ID NO:29    PNYFKIKEE-VKDKVYGITISGSGPSIIA-------------------------------
SEQ ID NO:22    PGMAAVKAAALQAGALGCTISGAGPTVVAVIQGEERGEEVARKMVDAFWSAGKLKATATV
SEQ ID NO:24    ------------------------------------------------------------
SEQ ID NO:59    PGMAAVKAAALEAGALGCTISGAGPTAVAVIDGEEKGEEVGRRMVEAFANAGNLKATATV
SEQ ID NO:26    PGMEAVKRAAIQAGAFGCTISGAGPTAVAVIDDEQTGHLIAKHMIDAFLHVGNLKASANV
SEQ ID NO:28    ------------------------------------------------------------
              301                                                           360
```

Figure 4C

```
                ++  +++
SEQ ID NO:60  KKLDKVGAR---------------------------------------------------
SEQ ID NO:29  ------------------------FPKEEFIDEVENILR----DYYE-------------
SEQ ID NO:22  AQLDTLGARVIATS----SLN---------------------------------------
SEQ ID NO:24  ------------------------------------------------------------
SEQ ID NO:59  AQLDRVGARVISTS----TLE---------------------------------------
SEQ ID NO:26  KQLDRLGARRIPNTFSSLSLEACRFQEPDFFQLARNTLSADRSHVFEISDQSSILVWRSE
SEQ ID NO:28  ------------------------------------------------------------
             361                                                         420

SEQ ID NO:60  ------------------------------------------------LVNSVSR-----
SEQ ID NO:29  NTIRTEVGKGV---EVV-------------------------------------------
SEQ ID NO:22  ------------------------------------------------------------
SEQ ID NO:24  ------------------------------------------------------------
SEQ ID NO:59  ------------------------------------------------------------
SEQ ID NO:26  QEKHTQAGSSVWVVEIIDELKTIRSVLWTLKHVLDFLCFVFIIFLSCYLSQSSKRSHFYF
SEQ ID NO:28  ------------------------------------------------------------
             421                                                         480

SEQ ID NO:60  ----------------
SEQ ID NO:29  ----------------
SEQ ID NO:22  ----------------
SEQ ID NO:24  ----------------
SEQ ID NO:59  ----------------
SEQ ID NO:26  LVSLCLILAFEHVLFL
SEQ ID NO:28  ----------------
             481               496
```

Figure 5A

```
SEQ ID NO:66   M--ASFINNPLTSLCNTKSERNNLFKISL----------YEAQSLGFSKLNGSRKVAFPS
SEQ ID NO:32   M--AD--------------AKST-------------------------------------
SEQ ID NO:65   M--ASLVNNAYAAIRTSKLE-----------------------------LREVKNLANFR
SEQ ID NO:62   ---------------------MASWSSPSAAANAASGARFGPFPSGGQRLAPCPSLVRGT
SEQ ID NO:64   ARGSNYGTTPLSNTSESEQRKMASWSSPVAA--AALQVHFGSSCFFSAR-SPRQTLLLPP
SEQ ID NO:31   M--AV--------------ERSG-------------------------------------
               1                                                          60

                                                           ***** **  *** **
SEQ ID NO:66   VVCKAV---------------SVPTKSS-----------TEIEGLNIAEDVTQLIGNTPM
SEQ ID NO:32   ----------------------------------------------IAKDVTELIGNTPL
SEQ ID NO:65   VGPPSSLS------CNNFKKVSSSPIT---CKAVSLSPPSTIEGLNIAEDVSQLIGKTPM
SEQ ID NO:62   PAPTLVLRLHPDGRGHGLLAHTGPSPSSR-CRAVA----AEVGGLNIANDVTQLIGNTPM
SEQ ID NO:64   LARNPTLTIQP--RPHPFRNINSSSSSWMCHAVA----AEVEGLNIADDVTQLIGKTPM
SEQ ID NO:31   ----------------------------------------------IAKDVTELIGKTPL
               61                                                        120

               ****    * **  ***** **** ******* *** *** ** * **   * * *****
SEQ ID NO:66   VYLNTIAKGCVANIAAKLEIMEPCCSVKDRIGFSMIVDAEEKGLISPGKTVLVEPTSGNT
SEQ ID NO:32   VYLNRVVDGCVARVAAKLEMMEPCSSVKDRIGYSMISDAENKGLITPGESVLIEPTSGNT
SEQ ID NO:65   VYLNNVSKGSVANIAAKLESMEPCCSVKDRIGYSMIDDAEQKGVITPGKTTLVEPTSGNT
SEQ ID NO:62   VYLNNVVKGSVANVAAKLEIMEPCCSVKDRIGYSMINDAEQKGLITPGKSVLVEATSGNT
SEQ ID NO:64   VYLNNIVKGCVANVAAKLEIMEPCCSVKDRIGYSMISDAEEKGLITPGKSVLVEPTSGNT
SEQ ID NO:31   VYLNKLADGCVARVAAKLELMEPCSSVKDRIGYSMIADAEEKGLITPGKSVLIEPTSGNT
               121                                                       180
```

Figure 5B

```
              ****** **  ***    ** *** ***  * ********** * * ***  ** **
SEQ ID NO:66  GIGLAFIAASRGYKLILTMPASMSLERRVILKAFGAELVLTDPAKGMKGAVSKAEEILNN
SEQ ID NO:32  GIGLAFIAAAKGYRLIICMPASMSLERRTILRAFGAELVLTDPARGMKGAVQKAEEIKAK
SEQ ID NO:65  GIGLAFIAAARGYKITLTMPASMSMERRVILKAFGAELVLTDPAKGMKGAVEKAEEILKK
SEQ ID NO:62  GIGLAFIAASKGYKLILTMPSSMSMERRVLLRAFGAELVLTDAAKGMKGALDKATEILNK
SEQ ID NO:64  GIGLAFIAASRGYKLILTMPASMSMERRVLLKAFGAELVLTDAAKGMKGAVDKATEILNK
SEQ ID NO:31  GIGLAFMAAARGYKLIITMPASMSLERRIILLAFGAELVLTDPAKGMKGAVQKAEEILAK
             181                                                        240

              **  * **** *****  **********    ** *    *******  * *  *** **
SEQ ID NO:66  TPDAYILQQFDNPANPKIHYETTGPEIWEDTKGKIDILVAGIGTGGTITGTGRFLKEQNP
SEQ ID NO:32  TPNSYILQQFENPANPKIHYETTGPEIWRGSGGKIDALVSGIGTGGTVTGAGKYLKEQNP
SEQ ID NO:65  TPDSYMLQQFDNPANPKIHYETTGPEIWEDTKGKVDIFVAGIGTGGTISGVGRYLKERNP
SEQ ID NO:62  TPNSYMLQQFDNPANPQVHYETTGPEIWEDSKGKVDIFIGGIGTGGTISGAGRFLKEKNP
SEQ ID NO:64  TPDAYMLQQFDNPANPKVHYETTGPEIWEDSKGKVDVFIGGIGTGGTISGAGRFLKEKNP
SEQ ID NO:31  TPNAYILQQFENPANPKVHYETTGPEIWKGSDGKIDAFVSGIGTGGTITGAGKYLKEQNP
             241                                                        300

                   * ** **  ****************** *  *     ***   ** *  * *  *
SEQ ID NO:66  NIKIIGVEPTESNVLSGGKPGPHKIQGIGAGFIPGNLDQDVMDEVIEISSDEAVETARTL
SEQ ID NO:32  NIKLYGVEPVESAILSGGKPGPHKIQGIGAGFIPGVLDVNLLDEVIQVSSEESIETAKLL
SEQ ID NO:65  GVQVIGIEPTESNILSGGKPGPHKIQGLGAGFVPSNLDLGVMDEVIEVSSEEAVEMAKQL
SEQ ID NO:62  GIKVIGIEPSESNILSGGKPGPHKIQGIGAGFVPRNLDSDILDEVIEISSDEAVETAKQL
SEQ ID NO:64  GIKVIGIEPSESNILSGGKPGPHKIQGIGAGFVPRNLDSEVLDEVIEISSDEAVETAKQL
SEQ ID NO:31  NIKLIGVEPVESPVLSGGKPGPHKIQGIGAGFIPGVLEVNLLDEVVQISSDEAIETAKLL
             301                                                        360
```

Figure 5C

```
              *  *** ********* **    *********   **** ******  *  *   * *
SEQ ID NO:66  ALQEGLLVGISSGAAALAAIQVGKRPENAGKLIGVVFPSYGERYLSSILFQSIREECEKM
SEQ ID NO:32  ALKEGLLVGISSGAAAAAAIRIAKRPENAGKLIVAVFPSFGERYLSTVLFESVKRETENM
SEQ ID NO:65  AMKEGLLVGISSGAAAAAAVRIGKRPENAGKLIAVVFPSFGERYLSSILFQSIREECENM
SEQ ID NO:62  AVQEGLLVGISSGAAAAAAIKVAKRPENAGKLIVVVFPSFGERYLSSVLYQSIREECENM
SEQ ID NO:64  ALQEGLLVGISSGAAAAAAIKVAKRPENAGKLVVVVFPSFGERYLSSILFQSIREECEKL
SEQ ID NO:31  ALKEGLFVGISSGAAAAAAFQIAKRPENAGKLIVAVFPSFGERYLSSVLFESVRREAESM
             361                                                           420

                *
SEQ ID NO:66  KPEL
SEQ ID NO:32  VFEP
SEQ ID NO:65  KPE-
SEQ ID NO:62  QPEP
SEQ ID NO:64  QPEP
SEQ ID NO:31  TFEP
             421  424
```

Figure 6A

```
              *
SEQ ID NO:41  MTSSLSLHSS----------FVPSFADLSDRGLISKNSPTSVSISKVPTWEKKQISNR-N
SEQ ID NO:34  ------------------------------------------------------------
SEQ ID NO:68  M--------AVAVPNAPGRLFLLQSTPFPN-PSSSASAARAQSF-RVPP-LRLSLFRRMA
SEQ ID NO:36  ------------------------------------------------------------
SEQ ID NO:70  MSAAAAAAAAAAIPTSLGRLFHLRPTPN---PSRNLSGSSAQPLLRLSYHPRLTLSRRME
SEQ ID NO:38  MFSSAISQKPFLQSLVIDR-YAQSTTAATRWECLGFNKSENFSTKRVL---------RAE
SEQ ID NO:40  ------------------------------------------------------------
SEQ ID NO:72  M--------AAA---AATRLFLLHSSPPSSLPCPNPSPSSAHTP-RPAY-PRLALAHRMA
              1                                                          60

                 *                                       *  *        **
SEQ ID NO:41  SFKLNCVMEKSVDGQTHSTVNNTT-DSLNTMNIKE------EASVSTLLVNLDNKFDPFD
SEQ ID NO:34  ------------------------------------------------------------
SEQ ID NO:68  GRSLTVIAGASGGSERDLSASAVSVEALDSVASDSD-LETKEPSVSTMLTSFENSFDKYG
SEQ ID NO:36  ------------------------------------------------------------
SEQ ID NO:70  AP--AAIADSHGGG--DLSASAVGAEALGAVAAPDFDVEMKEPSVATILTSFENSFDGFG
SEQ ID NO:38  GFKLNCLVE-----NREMEVESSSSSLVDDAAMSLSEEDLGEPSISTMVMNFESKFDPFG
SEQ ID NO:40  -----------------------------------------HESVATILTSFENSFDKYG
SEQ ID NO:72  AAP-AAIAGPSGDSERDLSASAVSLEALGAVESSGDGLERKEPSVATILTSFENSFDKYG
             61                                                           120
```

Figure 6B

```
                *************** * ************ * ** *** *** * ******* *
SEQ ID NO:41    AMSTPLYQTATFKQPSAIENGPYDYTRSGNPTRDALESLLAKLDKADRAFCFTSGMAALS
SEQ ID NO:34    ------------------------------------------------------------
SEQ ID NO:68    ALSTPLYQTATFKQPSATDYGTYDYTRSGNPTRDVLQSLMAKLEKADQAFCFTSGMAALA
SEQ ID NO:36    -------------------------------------LMAKLEKADQAFCFTSGMAALA
SEQ ID NO:70    SMSTPLYQTATFKQPSATDNGPYDYTRSGNPTRDVLQSLMAKLEKADQAFCFTSGMAALA
SEQ ID NO:38    AISTPLYQTATFKQPSAIENGPYDYTRSGNPTRDALESLLAKLDKADRALCFTSGMAALS
SEQ ID NO:40    ALSTPLYQTATFKQPSATVNGAYDYTRSGNPTRDVLQSLMAKLEKADQAFCFTSGMASLA
SEQ ID NO:72    ALSTPLYQTATFKQPSATVNGAYDYTRSGNPTRDVLQSLMAKLEKADQAFCFTSGMASLA
             121                                                            180

                **  *   * *** * * *********** ** * ****  *     *  ***  * ***
SEQ ID NO:41    AVTHLIKNGEEIVAGDDVYGGSDRLLSQVVPRSGVVVKRVNTTKLDEVAAAIGPQTKLVW
SEQ ID NO:34    ------------------------------------------------------------
SEQ ID NO:68    AVKHLLQAGQEIVAGEDIYGGSDRLLSQVVPRNGIVVKRVDTTKISDVVSAIGPSTRLVW
SEQ ID NO:36    AVTHLLKSGQEIVAGEDIYGGSDRLLSQVAPRHGIVVKRIDTTKISEVTSAIG-------
SEQ ID NO:70    AVTHLLKSGQEIVAGEDIYGGSDRLLSQVAPRHGIVVKRIDTTKISEVTSAIGPLTKLVW
SEQ ID NO:38    AVVRLVGTGEEIVTGDDVYGGSDRLLSQVVPRTGIVVKRVNTCDLDEVAAAIGLRTKLVW
SEQ ID NO:40    AVTHLLQAGQEIVAGEDIYGGSDRLLSQVVPRNGIVVKRVDTTKINDVTAAIGPLTRLVW
SEQ ID NO:72    AVTHLLQAGQEIVAGEDIYGGSDRLLSQVVPRNGIVVKRVDTTKINDVTAAIGPLTRLVW
             181                                                            240
```

Figure 6C

```
              ******** ** ** ** * **  **************** * *****************
SEQ ID NO:41  LESPTNPRQQISDIRKISEMAHAQGALVLVDNSIMSPVLSRPLELGADIVMHSATKFIAG
SEQ ID NO:34  ------------------IAHSHGALVLVDNSIMSPVLSRPIELGADIVMHSATKFIAG
SEQ ID NO:68  LESPTNPRQQITDIKTISEIAHSHGALVLVDNSIMSPVLSRPIELGADIVMHSATKFIAG
SEQ ID NO:36  ------------------------------------------------------------
SEQ ID NO:70  LESPTNPRLQITDIKKIAEIAHYHGALVLVDNSIMSPVLSRPLELGADIVMHSATKFIAG
SEQ ID NO:38  LESPTNPRLQISDIRKISEMAHSHGALVLVDNSIMSPVLSQPLELGADIVMHSATKFIAG
SEQ ID NO:40  LESPTNPRQQITDIKKISEIAHSHGALVLVDNSIMSPVLSWPIELGADIVMHSATKFIAG
SEQ ID NO:72  LESPTNPRQQITDIKKISEIAHSHGALVLVDNSIMSPVLSWPIELGADIVMHSATKFIAG
            241                                                         300

              *** *** ******  * **  **** *********************** **** ** *
SEQ ID NO:41  HSDVMAGVLAVKGEK-LAKEVYFLQNSEGSGLAPFDCWLCLRGIKTMALRIEKQQENARK
SEQ ID NO:34  HSDLMAGILAVKGES-LAKEVGFLQNAEGSGLAPFDCWLCLRGIKTMALRVEKQQANAQK
SEQ ID NO:68  HSDLMAGILAVKGES-LAKEVGFLQNAEGSGLAPFDCWLCLRGIKTMALRVEKQQANAQK
SEQ ID NO:36  ------------------------------------------------------------
SEQ ID NO:70  HSDLMAGILAVKGESSLAKEIAFLQNAEGSGLAPFDCWLCLRGIKTMALRVEKQQANAQK
SEQ ID NO:38  HSDIMAGVLAVKGEK-LGKEMYFLQNAEGSGLAPFDCWLCLRGIKTMALRIEKQQDNAQK
SEQ ID NO:40  HSDLMAGILAVKGES-LAKEIAFLQNAEGSGLAPFDCWLCLRGIKTMALRVEKQQDNAQK
SEQ ID NO:72  HSDLMAGILAVKGES-LAKEIAFLQNAEGSGLAPFDCWLCLRGIKTMALRVEKQQDNAQK
            301                                                         360
```

Figure 6D

```
                 *** * ****** * ***** ***   * ********* ** ***  **** *******
SEQ ID NO:41     IAMYLSSHPRVKKVYYAGLPDHPGHHLHFSQAKGAGSVFSFITGSVALSKHLVETTKYFS
SEQ ID NO:34     IAEFLASHPRVKQVNYAGLPDHPGRALHYSQAKGAGSVLSFLTGSLALSKHVVETTKYFS
SEQ ID NO:68     IAEFLASHPRVKQVNYAGLPDHPGRALHYSQAKGAGSVLSFLTGSLALSKHVVETTKYFS
SEQ ID NO:36     ------------------------------------------------------------
SEQ ID NO:70     IAEFLASHPRVKKVNYAGLPDHPGRSLHYSQAKGAGSVLSFLTGSLALSKHVVETTKYFN
SEQ ID NO:38     IAEFLASHPRVKEVNYAGLPGHPGRDLHYSQAKGAGSVLSFLTGSLALSKHIVETTKYFS
SEQ ID NO:40     IAEFLASHPRVKQVNYAGLPDHPGRSLHYSQAKGAGSVLSFQTGSLSLSKHVVETTKYFN
SEQ ID NO:72     IAEFLASHPRVKQVNYAGLPDHPGRSLHYSQAKGAGSVLSFQTGSLSLSKHVVETTKYFN
                361                                                         420

                  *********** ********** *** **** ****** ****  *** **  *   *
SEQ ID NO:41     IAVSFGSVKSLISMPCFMSHASIPAEVREARGLTEDLVRISAGIEDVDDLISDLDIAFKTFPL
SEQ ID NO:34     VTVSFGSVKSLISLPCFMSHASIPASVREERGLTDDLVRISVGIEDVEDLIADLDRALRTGPV
SEQ ID NO:68     VTVSFGSVKSLISLPCFMSHASIPASVREERGLTDDLVRISVGIEDVEDLIADLDRALRTGPV
SEQ ID NO:36     ---------------------------------------------------------------
SEQ ID NO:70     VTVSFGSVKSLISLPCFMSHASIPSAVREERGLTDDLVRISVGIEDADDLIADLDHALRSGPA
SEQ ID NO:38     ITVSFGSVKSLISMPCFMSHASIPAAVREARGLTEDLVRISVGIEDVNDLIADLGNALRTGPL
SEQ ID NO:40     VTVSFGSVKSLISLPCFMSHASIPSSVREERGLTDDLVRISVGIEDVDDLIADLDYALRSGPA
SEQ ID NO:72     VTVSFGSVKSLISLPCFMSHASIPSSVREERGLTDDLVRISVGIEDVDDLIADLDYALRSGPA
                421                                                            483
```

PLANT AMINO ACID BIOSYNTHETIC ENZYMES

This application is a continuation of application Ser. No. 09/931,457 filed Aug. 16, 2001, now abandoned, which is a continuation-in-part of application Ser. No. 09/424,976 filed on Dec. 2, 1999 now abandoned which is a national stage application of PCT/US98/12073 with an International filing date of Jun. 11, 1998, which in turn claims priority benefit of U.S. Provisional Application No. 60/049,406, filed Jun. 12, 1997 and U.S. Provisional Application No. 60/065,385, filed Nov. 12, 1997.

FIELD OF THE INVENTION

This invention is in the field of plant molecular biology. More specifically, this invention pertains to nucleic acid fragments encoding enzymes involved in amino acid biosynthesis in plants and seeds.

BACKGROUND OF THE INVENTION

Many vertebrates, including humans, lack the ability to manufacture a number of amino acids and therefore require these amino acids in their diet. These are called essential amino acids. Grain-derived foods or feed, however, are deficient in certain essential amino acids, such as lysine, the sulfur-containing amino acids methionine and cysteine, threonine and tryptophan. For example, in corn (*Zea mays* L.) lysine is the most limiting amino acid for the dietary requirements of many animals, and soybean (*Glycine max* L.) meal is used as an additive to corn-based animal feeds primarily as a lysine supplement. Often microbial-fermentation produced lysine is needed for such supplementation. Thus, an increase in lysine content of either corn or soybean would reduce or eliminate the need to supplement mixed grain feeds with lysine produced via fermentation.

Furthermore, in corn the sulfur amino acids are the third most limiting amino acids, after lysine and tryptophan, for the dietary requirements of many animals. Legume plants, however, while rich in lysine and tryptophan, have low sulfur-containing amino acid content. Therefore, the use of soybean meal to supplement corn in animal feed is not satisfactory. An increase in the sulfur amino acid content of either corn or soybean would improve the nutritional quality of the mixtures and reduce the need for further supplementation through addition of more expensive methionine.

One approach to increasing the nutritional quality of human foods and animal feed is to increase the production and accumulation of specific free amino acids via genetic engineering of the biosynthetic pathway of the essential amino acids. Biosynthetically, lysine, threonine, methionine, cysteine and isoleucine are all derived from aspartate. Regulation of the biosynthesis of each member of this family is interconnected (see FIG. 1). The organization of the pathway leading to biosynthesis of lysine, threonine, methionine, cysteine and isoleucine indicates that over-expression or reduction of expression of genes encoding, inter alia, aspartic semialdehyde dehydrogenase, homoserine kinase, diaminopimelate decarboxylase, cysteine synthase and cystathionine β-lyase in corn and soybean could be used to alter levels of these amino acids in human food and animal feed. However, few of the genes encoding enzymes that regulate this pathway in plants, especially corn and soybeans, are available. Accordingly, availability of nucleic acid sequences encoding all or a portion of these enzymes would facilitate development of nutritionally improved crop plants.

SUMMARY OF THE INVENTION

The present invention relates to isolated polynucleotides selected from the group consisting of SEQ ID NOs:1, 3, 5, 42, 44, 46, 48, 50, 8, 10, 12, 14, 16, 18, 53, 55, 21, 23, 25, 27, 58, 30, 61, 63, 33, 35, 37, 39, 67, 69, and 71.

The present invention concerns isolated polynucleotides comprising a nucleotide sequence selected from the group consisting of: (a) a nucleotide sequence encoding a polypeptide of at least 60 amino acids having at least 80% identity based on the Clustal method of alignment when compared to a polypeptide selected from the group consisting of SEQ ID NOs:2, 4, 6, 43, 45, 47, 49, and 51; (b) a nucleotide sequence encoding a polypeptide of at least 60 amino acids having at least 95% identity based on the Clustal method of alignment when compared to a polypeptide selected from the group consisting of SEQ ID NOs:9, 11, 13, 15, 17, 19, 54 and 56; (c) a nucleotide sequence encoding a polypeptide of at least 60 amino acids having at least 80% identity based on the Clustal method of alignment when compared to a polypeptide selected from the group consisting of SEQ ID NOs:22, 24, 26, 28, and 59; (d) a nucleotide sequence encoding a polypeptide of at least 60 amino acids having at least 95% identity based on the Clustal method of alignment when compared to a polypeptide selected from the group consisting of SEQ ID NOs:31, 62, and 64; and (e) a nucleotide sequence encoding a polypeptide of at least 60 amino acids having at least 85% identity based on the Clustal method of alignment when compared to a polypeptide selected from the group consisting of SEQ ID NOs:34, 36, 38, 40, 68, 70, and 72. It is preferred that the identity be at least 85%, more preferably at least 90%, still more preferably at least 95%. This invention also relates to the isolated complement of such polynucleotides, wherein the complement and the polynucleotide consist of the same number of nucleotides, and the nucleotide sequences of the complement and the polynucleotide have 100% complementarity.

In a third embodiment nucleotide sequence of the isolated first polynucleotide is selected from SEQ ID NOs:1, 3, 5, 42, 44, 46, 48, 50, SEQ ID NOs:8, 10, 12, 14, 16, 18, 53 and 55, SEQ ID NOs:21, 23, 25, 27, and 58, SEQ ID NOs:30, 61, and 63, and SEQ ID NOs:33, 35, 37, 39, 67, 69, and 71.

In a fourth embodiment, this invention concerns an isolated polynucleotide encoding an aspartic semialdehyde dehydrogenase, a diaminopimelate decarboxylase, a homoserine kinase, a cysteine γ synthase or a cystathionine β-lyase.

In a fifth embodiment, this invention relates to a chimeric gene comprising the polynucleotide of the present invention.

In a sixth embodiment, the present invention concerns an isolated nucleic acid molecule that comprises at least 180 nucleotides and remains hybridized with the isolated polynucleotide of the present invention under a wash condition of 0.1×SSC, 0.1% SDS, and 65° C.

In a seventh embodiment, the invention also relates to a host cell comprising a chimeric gene of the present invention or an isolated polynucleotide of the present invention. The host cell may be eukaryotic, such as a yeast cell or a plant cell, or prokaryotic, such as a bacterial cell. The present invention may also relate to a virus comprising an isolated polynucleotide of the present invention or a chimeric gene of the present invention.

In an eighth embodiment, the invention concerns a transgenic plant comprising a polynucleotide of the present invention.

In a ninth embodiment, the invention relates to a method for transforming a cell by introducing into such cell the polynucleotide of the present invention, or a method of producing a transgenic plant by transforming a plant cell with the polynucleotide of the present invention and regenerating a plant from the transformed plant cell.

In a tenth embodiment, the invention concerns a method for producing a nucleotide fragment by selecting a nucleotide sequence comprised by a polynucleotide of the present invention and synthesizing a polynucleotide fragment containing the nucleotide sequence. It is understood that the nucleotide fragment may be produced in vitro or in vivo.

In an eleventh embodiment the invention concerns an isolated polypeptide comprising an amino acid sequence selected from the group consisting of: (a) a polypeptide of at least 60 amino acids and having a sequence identity of at least 80% based on the Clustal method of alignment when compared to an amino acid sequence selected from the group consisting of SEQ ID NOs:2, 4, 6, 43, 45, 47, 49, and 51; (b) a polypeptide of at least 60 amino acids having a sequence identity of at least 95% based on the Clustal method of alignment when compared to an amino acid sequence selected from the group consisting of SEQ ID NOs:9, 11, 13, 15, 17, 19, 54 and 56; (c) a polypeptide of at least 60 amino acids having a sequence identity of at least 80% based on the Clustal method of alignment when compared to an amino acid sequence selected from the group consisting of SEQ ID NOs:22, 24, 26, 28, and 59; (d) polypeptide of at least 60 amino acids having an identity of at least 95% based on the Clustal method of alignment when compared to an amino acid sequence selected from the group consisting of SEQ ID NOs:31, 62, and 64; and (e) a polypeptide of at least 60 amino acids having a sequence identity of at least 85% based on the Clustal method of alignment when compared to an amino acid sequence selected from the group consisting of SEQ ID NOs:34, 36, 38, 40, 68, 70, and 72. It is preferred that the identity be at least 85%, it is more preferred if the identity is at least 90%, it is preferable that the identity be at least 95%.

In a twelfth embodiment the invention relates to an isolated polypleptide selected from SEQ ID NOs:2, 4, 6, 43, 45, 47, 49, and 51, SEQ ID NOs:9, 11, 13, 15, 17, 19, 54 and 56, SEQ ID NOs:22, 24, 26, 28, and 59, SEQ ID NOs:31, 62, and 64, and SEQ ID NOs:34, 36, 38, 40, 68, 70, and 72.

In a thirteenth embodiment, this invention concerns an isolated polypeptide having aspartic semialdehyde dehydrogenase, diaminopimelate decarboxylase, homoserine kinase, cysteine γ synthase, or cystathionine β-lyase function.

In a fourteenth embodiment, this invention relates to a method of altering the level of expression of a plant biosynthetic enzyme in a host cell comprising: transforming a host cell with a chimeric gene of the present invention; and growing the transformed host cell under conditions that are suitable for expression of the chimeric gene.

A further embodiment of the instant invention is a method for evaluating a compound for its ability to inhibit the activity of a plant biosynthetic enzyme selected from the group consisting of aspartic semialdehyde dehydrogenase, diaminopimelate decarboxylase, homoserine kinase, cysteine γ synthase and cystathionine β-lyase, the method comprising the steps of: (a) transforming a host cell with a chimeric gene comprising a nucleic acid fragment encoding a plant biosynthetic enzyme selected from the group consisting of aspartic semialdehyde dehydrogenase, diaminopimelate decarboxylase, homoserine kinase, cysteine synthase and cystathionine β-lyase, operably linked to regulatory sequences; (b) growing the transformed host cell under conditions that are suitable for expression of the chimeric gene wherein expression of the chimeric gene results in production of the biosynthetic enzyme in the transformed host cell; (c) optionally purifying the biosynthetic enzyme expressed by the transformed host cell; (d) treating the biosynthetic enzyme with a compound to be tested; and (e) comparing the activity of the biosynthetic enzyme that has been treated with a test compound to the activity of an untreated biosynthetic enzyme.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 1 depicts the biosynthetic pathway for the aspartate family of amino acids. The following abbreviations are used: AK=aspartokinase; ASADH=aspartic semialdehyde dehydrogenase; DHDPS=dihydrodipicolinate synthase; DHDPR=dihydrodipicolinate reductase; DAPEP=diaminopimelate epimerase; DAPDC=diaminopimelate decarboxylase; HDH=homoserine dehydrogenase; HK=homoserine kinase; TS=threonine synthase; TD=threonine deaminase; CγS=cystathionine γ-synthase; CβL=cystathionine β-lyase; MS=methionine synthase; CS=cysteine synthase; and SAMS=S-adenosylmethionine synthase.

FIGS. 2 through 6 show the amino acid sequence alignments between the known art sequences for aspartic semialdehyde dehydrogenase, diaminopimelate decarboxylase, homoserine kinase, cysteine γ synthase, and cystathione β-lyase with the sequences included in this application. Alignments were performed using the Clustal alogarithm described in Higgins and Sharp (1989) (CABIOS 5:151-153). Amino acids conserved among all sequences are indicated by an asterisk (*) above the alignment. Dashes are used by the program to maximize the alignment. A description of FIGS. 2 through 6 follows:

FIG. 2 shows a comparison of the aspartic semialdehyde dehydrogenase amino acid sequences from corn contig assembled from clones p0003.cgpha22r:fis, cpe1c.pk009.b24, p0016.ctscp83r, and p0075.cslab16r (SEQ ID NO:43), rice clone rlr48.pk0003.d12 (SEQ ID NO:2), the contig of 5' RACE PCR and rice clone rlr48.pk0003.d12 (SEQ ID NO:45), soybean clones sfl1.pk0122.f9 (SEQ ID NO:6), ses9c.pk001.a15:fis (SEQ ID NO:47), and sfl1.pk0122.f9:fis (SEQ ID NO;49), wheat clones wr1.pk0004.c11 (SEQ ID NO:4) and wdk1c.pk014.n5:fis (SEQ ID NO:51) with the *Legionella pneumophila* (NCBI General Identifier No. 2645882; SEQ ID NO:7) and the *Aquifex aeolicus* sequences (NCBI General Identifier No. 6225258; SEQ ID NO:52). FIG. 2A: positions 1 through 120; FIG. 2B: positions 121 through 240; FIG. 2C: positions 241 through 360; FIG. 2D: positions 361 through 392.

FIG. 3 shows a comparison of the diaminopimelate decarboxylase amino acid sequences derived from corn clones cen3n.pk0067.a3 (SEQ ID NO:9) and cr1n.pk0103.d8 (SEQ ID NO:11), rice clone rl0n.pk0013.b9 (SEQ ID NO:13), soybean clones sr1.pk0132.c1 (SEQ ID NO:15), sdp3c.pk001.o15 (SEQ ID NO:19) and sdp3c.pk001.o15:fis (SEQ ID NO:54), wheat clones wlk1.pk0012.c2 (SEQ ID NO:17) and wlk1.pk0012.c2:fis (SEQ ID NO:56) with the *Pseudomonas aeruginosa* (NCBI General Identifier No. 118304; SEQ ID NO:20) and *Arabidopsis thaliana* sequences (NCBI General Identifier No. 9279586; SEQ ID NO:57). FIG. 3A: positions 1 through 120; FIG. 3B: positions 121 through 240; FIG. 3C: positions 241 through 360; FIG. 3D: positions 361 through 480; FIG. 3E: positions 481 through 535.

FIG. 4 shows a comparison of the homoserine kinase amino acid sequences derived from corn clone cr1n.pk0009.g4 (SEQ ID NO:22), rice clones rca1c.pk005.k3 (SEQ ID NO:24) and rca1c.pk005.k3:fis (SEQ ID NO:59), soybean clone ses8w.pk0020.b5 (SEQ ID NO:26), wheat clone w11n.pk0065.f2 (SEQ ID NO:28) with the *Methanococcus jannaschii* (NCBI General Identifier No. 1591748; SEQ ID NO:29) and the *Arabidopsis thaliana* sequences (NCBI General Identifier No. 4927412; SEQ ID NO:60). FIG. 4A: positions 1 through 180; FIG. 4B: positions 181 though 360; FIG. 4C: positions 361 through 396.

FIG. 5 shows a comparison of the cysteine γ synthase amino acid sequences derived from the corn contig assembled from clones cco1n.pk083.j4, chp2.pk0016.b1, cpd1c.pk004.b20, cr1n.pk0083.c5, csi1.pk0003.g6, and p0126.cnlcb49r (SEQ ID NO:62), rice clone rls6.pk0068.b7:fis (SEQ ID NO:64), soybean clone se3.05h06 (SEQ ID NO:31) with the *Citrullus lanatus* sequence (NCBI General Identifier No. 540497; SEQ ID NO:32), the *Spinacia oleracea* sequence (NCBI General Identifier No. 540497; SEQ ID NO:65), and the *Solanum tuberosum* sequence (NCBI General Identifier No. 11131628; SEQ ID NO:66). FIG. 5A: postions 1 through 180; FIG. 5B: positions 181 through 360; FIG. 5C: positions 361 through 424.

FIG. 6 shows a comparison of the amino acid sequences of the cystathionine β-lyase derived from corn clone cen1.pk0061.d4 (SEQ ID NO:34), corn contig assembled from clones p0005.cbmei71r, p0014.ctuui39r, p0109.cdadg47r, and p0125.czaay16r (SEQ ID NO:68), rice clone rlr12.pk0026.g1 (SEQ ID NO:36), the contig of 5' PCR and rice clone rlr12.pk0026.g1:fis (SEQ ID NO:70), soybean clone sfl1.pk0012.c4 (SEQ ID NO:38), and wheat clones wr1.pk0091.g6 (SEQ ID NO:40) and wr1.pk0091.g6:fis (SEQ ID NO:72) with the *Arabidopsis thaliana* sequence (NCBI General Identifier No. 1708993; SEQ ID NO:41). FIG. 6A: positions 1 through 120; FIG. 6B: positions 121 through 240; FIG. 6C: postions 241 through 360; FIG. 6D: positions 361 through 483.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Plant Biosynthetic Enzymes

| Polypeptide | Clone | SEQ ID NO: (Nucleotide) | SEQ ID NO: (Amino Acid) |
|---|---|---|---|
| rice ASADH | rlr48.pk0003.d12 | 1 | 2 |
| wheat ASADH | wr1.pk0004.c11 | 3 | 4 |
| soybean ASADH | sfl1.pk0122.f9 | 5 | 6 |
| *L. pneumophila* ASADH | NCBI GI 2645882 | | 7 |
| corn DAPEP | cen3n.pk0067.a3 | 8 | 9 |
| corn DAPEP | cr1n.pk0103.d8 | 10 | 11 |
| rice DAPEP | rl0n.pk0013.b9 | 12 | 13 |
| soybean DAPEP | sr1.pk0132.c1 | 14 | 15 |
| wheat DAPEP | wlk1.pk0012.c2 | 16 | 17 |
| soybean DAPEP | sdp3c.pk001.o15 | 18 | 19 |
| *P. aeruginosa* DAPEP | NCBI GI 118304 | | 20 |
| corn HK | cr1n.pk0009.g4 | 21 | 22 |
| rice HK | rca1c.pk005.k3 | 23 | 24 |
| soybean HK | ses8w.pk0020.b5 | 25 | 26 |
| wheat HK | wl1n.pk0065.f2 | 27 | 28 |
| *M. jannaschii* HK | NCBI GI 1591748 | | 29 |
| soybean CγS | se3.05h06 | 30 | 31 |
| *C. lanatus* CγS | NCBI GI 540497 | | 32 |
| corn CβL | cen1.pk0061.d4 | 33 | 34 |
| rice CβL | rlr12.pk0026.g1 | 35 | 36 |
| soybean CβL | sfl1.pk0012.c4 | 37 | 38 |
| wheat CβL | wr1.pk0091.g6 | 39 | 40 |
| *A. thaliana* CβL | NCBI GI 1708993 | | 41 |
| corn ASADH | Contig of:<br>p0003.cgpha22r:fis<br>cpe1c.pk009.b24<br>p0016.ctscp83r<br>p0075.cslab16r | 42 | 43 |
| rice ASADH | 5' RACE PCR + rlr48.pk0003.d12 | 44 | 45 |
| soybean ASADH | ses9c.pk001.a15:fis | 46 | 47 |
| soybean ASADH | sfl1.pk0122.f9:fis | 48 | 49 |
| wheat ASADH | wdk1c.pk014.n5:fis | 50 | 51 |
| *A. aeolicus* ASADH | NCBI GI 6225258 | | 52 |
| soybean DAPEP | sdp3c.pk001.o15:fis | 53 | 54 |
| wheat DAPEP | wlk1.pk0012.c2:fis | 55 | 56 |
| *A. thaliana* DAPEP | NCBI GI 9279586 | | 57 |
| rice HK | rca1c.pk005.k3:fis | 58 | 59 |
| *A. thaliana* HK | NCBI GI 4927412 | | 60 |
| corn CγS | Contig of:<br>cco1n.pk083.j4<br>chp2.pk0016.b1<br>cpd1c.pk004.b20 | 61 | 62 |

TABLE 1-continued

Plant Biosynthetic Enzymes

| Polypeptide | Clone | SEQ ID NO: (Nucleotide) | SEQ ID NO: (Amino Acid) |
|---|---|---|---|
| | cr1n.pk0083.c5 | | |
| | csi1.pk0003.g6 | | |
| | p0126.cnlcb49r | | |
| rice CγS | rls6.pk0068.b7:fis | 63 | 64 |
| *S. oleracea* CγS | NCBI GI 416869 | | 65 |
| *S. tuberosum* CγS | NCBI GI 11131628 | | 66 |
| corn CβL | Contig of: | 67 | 68 |
| | p0005.cbmei71r | | |
| | p0014.ctuui39r | | |
| | p0109.cdadg47r | | |
| | p0125.czaay16r | | |
| rice CβL | 5'RACE PCR + rlr12.pk0026.g1:fis | 69 | 70 |
| wheat CβL | wr1.pk0091.g6:fis | 71 | 72 |

The nucleotide and amino acid sequences shown in SEQ ID NOs:1 through 41 are found, with the same SEQ ID NO, in U.S. application Ser. No. 09/424,976. All or a portion of some of the sequences in the present application are found in the provisional applications for which the present application claims priority to. Table 1A indicates the SEQ ID NO: in the present application and the corresponding SEQ ID NO: in the previously-filed provisional application.

TABLE 1A

Sequence Priority

| Application No. 09/424,976 | Provisional Application No. 60/049406 | Provisional Application No. 60/065385 |
|---|---|---|
| SEQ ID NO: 1 | SEQ ID NO: 1 | |
| SEQ ID NO: 2 | SEQ ID NO: 2 | |
| SEQ ID NO: 3 | SEQ ID NO: 3* | |
| SEQ ID NO: 4 | SEQ ID NO: 4* | |
| SEQ ID NO: 8 | SEQ ID NO: 7 | SEQ ID NO: 8 |
| SEQ ID NO: 9 | SEQ ID NO: 8 | SEQ ID NO: 9 |
| SEQ ID NO: 12 | SEQ ID NO: 9 | |
| SEQ ID NO: 13 | SEQ ID NO: 10 | |
| SEQ ID NO: 14 | SEQ ID NO: 11 | SEQ ID NO: 5 |
| SEQ ID NO: 15 | SEQ ID NO: 12 | SEQ ID NO: 6 |
| SEQ ID NO: 21 | SEQ ID NO: 13 | SEQ ID NO: 10* |
| SEQ ID NO: 22 | SEQ ID NO: 14 | SEQ ID NO: 11* and 14* |
| SEQ ID NO: 23 | SEQ ID NO: 17* | SEQ ID NO: 15 |
| SEQ ID NO: 24 | SEQ ID NO: 18* | SEQ ID NO: 16 |
| SEQ ID NO: 25 | SEQ ID NO: 15 | SEQ ID NO: 13 |
| SEQ ID NO: 26 | SEQ ID NO: 16 | SEQ ID NO: 14 |
| SEQ ID NO: 30 | SEQ ID NO: 19 | SEQ ID NO: 17 |
| SEQ ID NO: 31 | SEQ ID NO: 20 | SEQ ID NO: 18 |
| SEQ ID NO: 33* | SEQ ID NO: 21 | SEQ ID NO: 19 |
| SEQ ID NO: 34 | SEQ ID NO: 22 | SEQ ID NO: 20 |
| SEQ ID NO: 37 | SEQ ID NO: 23 | SEQ ID NO: 21* |
| SEQ ID NO: 38 | SEQ ID NO: 24 | SEQ ID NO: 22* |

*Indicates that only a portion of the sequence was in the application.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms “polynucleotide,” “polynucleotide sequence,” “nucleic acid sequence,” and “nucleic acid fragment”/“isolated nucleic acid fragment” are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 42, 44, 46, 48, 50, SEQ ID NOs:8, 10, 12, 14, 16, 18, 53 and 55, SEQ ID NOs:21, 23, 25, 27, and 58, SEQ ID NOs:30, 61, and 63, and SEQ ID NOs:33, 35, 37, 39, 67, 69, and 71, or the complement of such sequences.

The term “isolated” polynucleotide refers to a polynucleotide that is substantially free from other nucleic acid sequences with which it is normally associated such as other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term “recombinant” means, for example, that a nucleic acid sequence is made by an artificial combination of two otherwise separated segments of sequence, e.g., by chemical synthesis or by the manipulation of isolated nucleic acids by genetic engineering techniques.

As used herein, “contig” refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from the group consisting of SEQ ID NOs:1, 3, 5, 42, 44, 46, 48, 50, SEQ ID NOs:8, 10, 12, 14, 16, 18, 53 and 55, SEQ ID NOs:21, 23, 25, 27, and 58, SEQ ID NOs:30, 61, and 63, and SEQ ID NOs:33, 35, 37, 39, 67, 69, and 71 and the complement of such nucleotide sequences may be used in methods of selecting an isolated polynucleotide that affects the expression of an aspartic-semialdehyde dehydrogenase, a diaminopimelate decarboxylase, a homoserine kinase, a cysteine γ synthase, or a cystathionine β-lyase polypeptide in a host cell. A method of selecting an isolated polynucleotide that affects the level of expression of a polypeptide in a host cell may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A “substantial portion” of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually, by one skilled in the art, or by using computer-based sequence comparison and identification tools that employ algorithms such as BLAST (Basic Local Alignment Search Tool; Altschul et al. (1993) *J. Mol. Biol.* 215:403-410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a “substantial portion” of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

“Codon degeneracy” refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the “codon-bias” exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

“Synthetic nucleic acid fragments” can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. “Chemically synthesized”, as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

“Gene” refers to a nucleic acid fragment that expresses a specific protein, including regulatory sequences preceding (5' non-coding sequences) and following (3' non-coding sequences) the coding sequence. “Native gene” refers to a gene as found in nature with its own regulatory sequences. “Chimeric gene” refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. “Endogenous gene” refers to a native gene in its natural location in the genome of an organism. A “foreign-gene” refers to a gene not normally found in the host organism, but that is introduced into the host organism by gene transfer. Foreign genes can comprise native genes inserted into a non-native organism, or chimeric genes. A “transgene” is a gene that has been introduced into the genome by a transformation procedure.

“Coding sequence” refers to a nucleotide sequence that codes for a specific amino acid sequence. “Regulatory sequences” refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

“Promoter” refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an “enhancer” is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as “constitutive promoters”. New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

“Translation leader sequence” refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (*London*) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns isolated polynucleotides comprising a nucleotide sequence selected from the group consisting of: (a) a nucleotide sequence encoding a polypeptide of at least 60 amino acids having at least 80% identity based on the Clustal method of alignment when compared to a polypeptide selected from the group consisting of SEQ ID NOs:2, 4, 6, 43, 45, 47, 49, and 51; (b) a nucleotide sequence encoding a polypeptide of at least 60 amino acids having at least 95% identity based on the Clustal method of alignment when compared to a polypeptide selected from the group consisting of SEQ ID NOs:9, 11, 13, 15, 17, 19, 54 and 56; (c) a nucleotide sequence encoding a polypeptide of at least 60 amino acids having at least 80% identity based on the Clustal method of alignment when compared to a polypeptide selected from the group consisting of SEQ ID NOs:22, 24, 26, 28, and 59; (d) a nucleotide sequence encoding a polypeptide of at least 60 amino acids having at least 95% identity based on the Clustal method of alignment when compared to a polypeptide selected from the group consisting of SEQ ID NOs:31, 62, and 64; and (e) a nucleotide sequence encoding a polypeptide of at least 60 amino acids having at least 85% identity based on the Clustal method of alignment when compared to a polypeptide selected from the group consisting of SEQ ID NOs:34, 36, 38, 40, 68, 70, and 72. It is preferred that the identity be at least 85%, it is preferable if the identity is at least 90%, it is more preferred that the identity be at least 95%. This invention also relates to the isolated complement of such polynucleotides, wherein the complement and the polynucleotide consist of the same number of nucleotides, and the nucleotide sequences of the complement and the polynucleotide have 100% complementarity.

Preferably, the isolated polynucleotide of the claimed invention comprises a nucleotide sequence selected from the group consisting of SEQ ID NOs:1, 3, 5, 42, 44, 46, 48, 50, 8, 10, 12, 14, 16, 18, 53, 55, 21, 23, 25, 27, 58, 30, 61, 63, 33, 35, 37, 39, 67, 69, and 71.

Nucleic acid fragments encoding at least a portion of several plant amino acid biosynthetic enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other aspartic semialdehyde dehydrogenases, diaminopimelate decarboxylases, homoserine kinases, cysteine γ synthases or cystathionine β-lyases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence selected from the group consisting of SEQ ID NOs:1, 3, 5, 42, 44, 46, 48, 50, 8, 10, 12, 14, 16, 18, 59, 61, 21, 23, 25, 27, 64, 30, 33, 35, 37, 39, 53, 55, and 57 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of an aspartic semialdehyde dehydrogenase, diaminopimelate decarboxylase, homoserine kinase, cysteine synthase, or cystathionine β-lyase polypeptide, preferably a substantial portion of a plant aspartic semialdehyde dehydrogenase, diaminopimelate decarboxylase, homoserine kinase, cysteine synthase, or cystathionine β-lyase polypeptide, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs:1, 3, 5, 42, 44, 46, 48, 50, 8, 10, 12, 14, 16, 18, 53, 55, 21, 23, 25, 27, 58, 30, 61, 63, 33, 35, 37, 39, 67, 69, and 71, and the complement of such nucleotide sequences; and amplifying a nucleic acid fragment (preferably a cDNA inserted in a cloning vector) using the oligonucleotide primer. The amplified nucleic acid fragment preferably will encode a portion of an aspartic semialdehyde dehydrogenase, diaminopimelate decarboxylase, homoserine kinase, cysteine synthase, or cystathionine β-lyase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of free amino acids in those cells. Specifically, the enzymes of the present invention form part of the pathway towards the biosynthesis of lysine, threonine, methionine, cysteine and isoleucine. In particular, altering the level and/or function of cystathionine beta-lyase will result in changes in the rate of methionine biosynthesis. Altering the level and/or function of diaminopimelate decarboxylase will result in changes in the rate of lysine biosynthesis. Altering the level and/or function of aspartate-semialdehyde dehydrogenase will result in changes in the lysine, methionine, or threonine content, especially in wheat. Altering the level of cysteine γ synthase will result in changes in the rate of cysteine and/or methionine biosynthesis; using this gene it will also be possible to control sulfur metabolism. Altering the level of homoserine kinase may be used to regulate threonine and methionine levels. Polypeptides encoding at least a portion of aspartic semialdehyde dehydrogenase, diaminopimelate decarboxylase, homoserine kinase, cysteine synthase, or cystathionine β-lyase may also be used in herbicide identification and design.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an aspartic-semialdehyde dehydrogenase polypeptide of at least 50 amino acids comprising at least 70% identity based on the Clustal method of alignment compared to a polypeptide selected from the group consisting of SEQ ID NOs:2, 4, 6, 43, 45, 47, 49, and 51, a diaminopimelate decarboxylase polypeptide of at least 60 amino acids comprising at least 95% identity based on the Clustal method of alignment compared to a polypeptide selected from the group consisting of SEQ ID NOs:9, 11, 13, 15, 17, 19, 60, and 62, a homoserine kinase polypeptide of at least 60 amino acids comprising at least 70% identity based on the Clustal method of alignment compared to a polypeptide selected from the group consisting of SEQ ID NOs:22, 24, 26, 28, and 65, a cysteine synthase polypeptide of at least 60 amino acids comprising at least 90% identity based on the Clustal method of alignment compared to a polypeptide of SEQ ID NO:31, or a cystathionine β-lyase polypeptide of at least 60 amino acids comprising at least 85% identity based on the Clustal method of alignment compared to a polypeptide selected from the group consisting of SEQ ID NOs:34, 36, 38, 40, 54, 56, and 58.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded plant biosynthetic enzymes. An example of a vector for high level expression of the instant polypeptides in a bacterial host is provided (Example 10).

Additionally, the instant polypeptides can be used as a target to facilitate design and/or identification of inhibitors of those enzymes that may be useful as herbicides. This is desirable because the polypeptides described herein catalyze various steps in a pathway leading to production of several essential amino acids. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries, Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cen1 | Corn Endosperm 12 Days After Pollination | cen1.pk0061.d4 |
| cen3n | Corn Endosperm 20 Days After Pollination* | cen3n.pk0067.a3 |
| cpe1c | Corn pooled BMS treated with chemicals related to phosphatase** | cpe1c.pk009.b24 |
| cr1n | Corn Root From 7 Day Seedlings* | cr1n.pk0009.g4 |
| cr1n | Corn Root From 7 Day Seedlings* | cr1n.pk0103.d8 |
| p0003 | Corn Premeiotic Ear Shoot, 0.2-4 cm | p0003.cgpha22r:fis |
| p0005 | Corn Immature Ear | p0005.cbmei71r |
| p0014 | Corn Leaves 7 and 8 from Plant Transformed with G-protein Gene, *C. heterostrophus* Resistant | p0014.ctuui39r |
| p0016 | Corn Tassel Shoots (0.1-1.4 cm), Pooled | p0016.ctscp83r |
| p0075 | Corn Shoot And Leaf Material From Dark-Grown 7 Day-Old Seedlings | p0075.cslab16r |
| p0109 | Corn Leaves From Les9 Transition Zone and Les9 Mature Lesions, Pooled*** | p0109.cdadg47r |
| p0125 | Corn Anther Prophase I* | p0125.czaay16r |
| rca1c | Rice Nipponbare Callus | rca1c.pk005.k3 |
| rl0n | Rice Leaf 15 Days After Germination* | rl0n.pk0013.b9 |
| rlr12 | Rice Leaf 15 Days After Germination, 12 Hours After Infection of Strain *Magaporthe grisea* 4360-R-62 (AVR2-YAMO) | rlr12.pk0026.g1 |
| rlr48 | Rice Leaf 15 Days After Germination 48 Hours After Infection of Strain *Magaporthe grisea* 4360-R-62 (AVR2-YAMO) | rlr48.pk0003.d12 |
| se3 | Soybean Embryo 13 Days After Flowering | sdp3c.pk001.o15 |
| sdp3c | Soybean Developing Pods 8-9 mm | se3.05h06 |
| ses8w | Mature Soybean Embryo 8 Weeks After Subculture | ses8w.pk0020.b5 |
| ses9c | Soybean Embryogenic Suspension | ses9c.pk001.a15:fis |
| sfl1 | Soybean Immature Flower | sfl1.pk0012.c4 |
| sfl1 | Soybean Immature Flower | sfl1.pk0122.f9 |
| sr1 | Soybean Root From 10 Day Old Seedlings | sr1.pk0132.c1 |
| wdk1c | Wheat Developing Kernel, 3 Days After Anthesis | wdk1c.pk014.n5:fis |

TABLE 2-continued cDNA Libraries from Corn, Rice, Soybean, and Wheat

| Library | Tissue | Clone |
|---|---|---|
| wl1n | Wheat Leaf from 7 Day Old Seedling* | wl1n.pk0065.f2 |
| wlk1 | Wheat Seedlings 1 hour After Fungicide Treatment**** | wlk1.pk0012.c2 |
| wr1 | Wheat Root From 7 Day Old Seedlings | wr1.pk0004.c11 |
| wr1 | Wheat Root From 7 Day Old Seedlings | wr1.pk0091.g6 |

*These libraries were normalized essentially as described in U.S. Pat. No. 5,482,845.
**Chemicals used included okadaic acid, cyclosporin A, calyculin A, and cypermethrin, all of which are commercially available from Molecular Biology supply sources including Calbiochem-Novabiochem Corp.
***L es9 mutants reviewed in "An update on lesion mutants" Hoisington (1986) Maize Genetic Coop. News Lett. 60: 50-51.
****Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765-3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147-5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding plant amino acid biosynthetic enzymes were identified by conducting BLAST (Basic Local Alignment Search Tool; Altschul et al. (1993) *J. Mol. Biol.* 215:403-410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389-3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Aspartate Semialdehyde Dehydrogenase The BLASTX search using the EST sequences from clones listed in Table 3 revealed similarity of the polypeptides encoded by the cDNAs to aspartate semialdehyde dehydrogenase from *Synechocystis* sp. (DDJB Accession No. D64006; NCBI General Identifier No. 1001379) or *Legionella pneumophila* (GenBank Accession No. AF034213; NCBI General Identifier No. 2645882). Shown in Table 3 are the BLAST results for individual ESTs ("EST"), or for the sequences of the entire cDNA inserts comprising the indicated cDNA clones ("FIS"):

TABLE 3

BLAST Results for Sequences Encoding Polypeptides Homologous to Aspartate Semialdehyde Dehydrogenase

| | | BLAST pLog Score | |
|---|---|---|---|
| Clone | Status | *Synechocystis* sp. GI 1001379 | *Legionella pneumophila* GI 2645882 |
| rlr48.pk0003.d12 | FIS | 51.00 | 36.00 |
| wr1.pk0004.c11 | EST | 67.96 | 44.74 |
| sfl1.pk0122.f9 | EST | | 6.60 |

The sequence of the entire cDNA insert in clone sfl1.pk0122.f9 was determined, RACE PCR was used to obtain the 5' portion of the rice aspartate semialdehyde dehydrogenase, and further sequencing and searching of the DuPont proprietary database allowed the identification of a corn and other a soybean, and wheat clones encoding aspartate semialdehyde dehydrogenase. The BLASTX search using the EST sequences from clones listed in Table 4 revealed similarity of the polypeptides encoded by the cDNAs to aspartate semialdehyde dehydrogenase from *Aquifex aeolicus* (NCBI General Identifier No. 6225258). Shown in Table 4 are the BLAST results for the sequences of contigs assembled from two or more ESTs ("Contig"), or the sequences encoding the entire protein derived from eithre the entire cDNA inserts comprising the indicated cDNA clones or contigs assembled from 5' RACE PCR and the sequence of the entire cDNA insert in the indicated cDNA clone ("CGS"):

TABLE 4

BLAST Results for Sequences Encoding Polypeptides Homologous to Aspartate Semialdehyde Dehydrogenase

| Clone | Status | BLAST pLog Score *Aquifex aeolicus* GI 6225258 |
|---|---|---|
| Contig of:<br>cpe1c.pk009.b24<br>p0003.cgpha22r:fis<br>p0016.ctscp83r<br>p0075.cslab16r | Contig | 78.70 |
| 5' RACE PCR +<br>rlr48.pk0003.d12:fis | CGS | 89.20 |
| ses9c.pk001.a15:fis | CGS | 87.40 |
| sfl1.pk0122.f9:fis | CGS | 88.10 |
| wdk1c.pk014.n5:fis | CGS | 91.50 |

FIG. 2 presents an alignment of the amino acid sequences set forth in SEQ ID NOs:2, 4, 6, 43, 45, 47, 49, and 51 with the *Legionella pneumophila* sequence (NCBI General Identifier No. 2645882; SEQ ID NO:7) and the *Aquifex aeolicus* sequence (NCBI General Identifier No. 6225258; SEQ ID NO:52). The data in Table 5 presents a calculation of the percent identity of the amino acid sequences set forth in SEQ ID NOs:2, 4, 6, 43, 45, 47, 49, and 51 with the *Legionella pneumophila* sequence (NCBI General Identifier No. 2645882; SEQ ID NO:7) and the *Aquifex aeolicus* sequence (NCBI General Identifier No. 6225258; SEQ ID NO:52).

TABLE 5

Percent Identity of Amino Acid Sequences Deduced From the Nucleotide Sequences of cDNA Clones Encoding Polypeptides Homologous to Aspartate Semialdehyde Dehydrogenase

| Clone | amino acid SEQ ID NO. | Percent Identity to 2645882 | 6225258 |
|---|---|---|---|
| rlr48.pk0003.d12 | 2 | 42.1 | 45.6 |
| wr1.pk0004.c11 | 4 | 42.3 | 44.8 |
| sfl1.pk0122.f9 | 6 | 29.1 | 25.6 |
| Contig of: cpe1c.pk009.b24 p0003.cgpha22r:fis p0016.ctscp83r p0075.cslab16r | 43 | 41.2 | 45.9 |
| 5' RACE PCR + rlr48.pk0003.d12:fis | 45 | 43.2 | 47.0 |
| ses9c.pk001.a15:fis | 47 | 43.5 | 49.1 |
| sfl1.pk0122.f9:fis | 49 | 41.2 | 45.6 |
| wdk1c.pk014.n5:fis | 51 | 43.2 | 49.4 |

As seen in FIG. 2, the amino acid sequence shown in SEQ ID NO:2 is identical to amino acids 181 through 375 of SEQ ID NO:45; the sequence shown in SEQ ID NO:4 is identical to amino acids 173 through 374 of the sequence shown in SEQ ID NO:51; the sequence shown in SEQ ID NO:6 is identical to amino acids 1 through 86 of the sequence shown in SEQ ID NO:49; there are 5 amino acid differences between the sequences shown in SEQ ID NO:47 and SEQ ID NO:49; there are 18 amino acid differences between amino acids 89 through 375 of the sequence shown in SEQ ID NO:43 and the sequence shown in SEQ ID NO:45; and there are 15 differences between the amino acid sequences shown in SEQ ID NO:45 and in SEQ ID NO:51.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn aspartate semialdehyde dehydrogenase, a substantial portion and an entire rice aspartate semialdehyde dehydrogenase, a portion and an entire wheat aspartate semialdehyde dehydrogenase, and a portion and an two entire soybean aspartate semialdehyde dehydrogenases.

Example 4

Characterization of cDNA Clones Encoding Diaminopimelate Decarboxylase

The BLASTX search using the EST sequences from clones listed in Table 6 revealed similarity of the polypeptides encoded by the cDNAs to diaminopimelate decarboxylase from *Aquifex aeolicus* (GenBank Accession No. AE000728 and NCBI General Identifier No. 2983642) and *Pseudomonas aeruginosa* (GenBank Accession No. M23174 and NCBI General Identifier No. 118304). Shown in Table 6 are the BLAST results for individual ESTs ("EST"), the sequences of the entire cDNA inserts comprising the indicated cDNA clones ("FIS"), or the sequences of FISs encoding an entire protein ("CGS"):

TABLE 6

BLAST Results for Sequences Encoding Polypeptides Homologous to Diaminopimelate Decarboxylase

| Clone | Status | BLAST pLog Score GI 2983642 (*A. aeolicus*) | GI 118304 (*P. aeruginosa*) |
|---|---|---|---|
| cen3n.pk0067.a3 | FIS | 58.22 | 56.00 |
| cr1n.pk0103.d8 | CGS | 75.25 | 79.12 |
| rl0n.pk0013.b9 | FIS | 46.40 | 44.00 |
| sr1.pk0132.c1 | FIS | 44.70 | 39.15 |
| wlk1.pk0012.c2 | EST | 20.48 | 19.05 |

An additional soybean clone, sdp3c.pk001.o15, was identified as sharing homology with sr1.pk0132.c1. BLASTX search using the nucleotide sequences from clone sdp3c.pk001.o15 revealed similarity of the proteins encoded by the cDNA to diaminopimelate decarboxylase from *Pseudomonas fluorescens* (EMBO Accession No. Y12268; NCBI General Identifier No. 1929095). This EST yields a pLog value of 8.66 versus the *Pseudomonas fluorescens* sequence.

The sequence of the entire cDNA insert in clones sdp3c.pk001.o15 and wlk1.pk0012.c2 was determined. The BLASTX search using the EST sequences from clones listed in Table 7 revealed similarity of the polypeptides encoded by the cDNAs to diaminopimelate decarboxylase from *Aquifex aeolicus* (NCBI General Identifier No. 6225241) or by the *Arabidopsis thaliana* contig containing similarity with diaminopimelate decarboxylases (NCBI General Identifier No. 9279586). Shown in Table 7 are the BLAST results for the sequences of the entire cDNA inserts comprising the indicated cDNA clones ("FIS"), or the sequences of FISs encoding the entire protein ("CGS"):

TABLE 7

BLAST Results for Sequences Encoding Polypeptides Homologous to Diaminopimelate Decarboxylase

| Clone | Status | Homolog | BLAST pLog Score |
|---|---|---|---|
| sdp3c.pk001.o15:fis | CGS | GI 6225241 (*A. aeolicus*) | 76.40 |
| wlk1.pk0012.c2:fis | FIS | GI 9279586 (*A. thaliana*) | 94.40 |

FIG. 3 presents an alignment of the amino acid sequences set forth in SEQ ID NOs:9, 11, 13, 15, 17, 19, 54, and 56 with the *Pseudomonas aeruginosa* sequence (NCBI General Identifier No. 118304; SEQ ID NO:20) and the *Arabidopsis thaliana* sequence (NCBI General Identifier No. 9279586, SEQ ID NO:57). The data in Table 8 presents a calculation of the percent identity of the amino acid sequences set forth in SEQ ID NOs:9, 11, 13, 15, 17, 19, 54, and 56 with the *Pseudomonas aeruginosa* sequence (NCBI General Identifier No. 118304; SEQ ID NO:20) and the *Arabidopsis thaliana* sequence (NCBI General Identifier No. 9279586; SEQ ID NO:57).

TABLE 8

Percent Identity of Amino Acid Sequences Deduced From the Nucleotide Sequences of cDNA Clones Encoding Polypeptides Homologous to Diaminopimelate Decarboxylase

| Clone | Amino acid SEQ ID NO. | Percent Identity to 118304 | 9279586 |
|---|---|---|---|
| cen3n.pk0067.a3 | 9 | 34.0 | 82.2 |
| cr1n.pk0103.d8 | 11 | 35.9 | 70.6 |
| rl0n.pk0013.b9 | 13 | 32.4 | 76.8 |
| sr1.pk0132.c1 | 15 | 29.7 | 86.1 |
| wlk1.pk0012.c2 | 17 | 42.5 | 93.2 |
| sdp3c.pk001.o15 | 19 | 41.9 | 87.1 |
| sdp3c.pk001.o15:fis | 54 | 32.5 | 74.9 |
| wlk1.pk0012.c2:fis | 56 | 32. | 84.9 |

The amino acid sequence set forth in SEQ ID NO:19 is identical to amino acids 112 through 173 of the amino acid sequence set forth in SEQ ID NO:54. The amino acid sequence set forth in SEQ ID NO:17 is identical to amino acids 24 through 96 of the amino acid sequence set forth in SEQ ID NO:56.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of one corn, one rice, two soybean and one wheat diaminopimelate decarboxylases and entire corn and soybean diaminopimelate decarboxylases.

Example 5

Characterization of cDNA Clones Encoding Homoserine Kinase

The BLASTX search using the EST sequences from clones listed in Table 9 revealed similarity of the polypeptides encoded by the cDNAs to homoserine kinase from *Methanococcus jannaschii* (GenBank Accession No. U67553 and NCBI General Identifier No. 1591748). Shown in Table 9 are the BLAST results for individual ESTs ("EST") or for the sequences of the entire cDNA inserts comprising the indicated cDNA clones ("FIS"):

TABLE 9

BLAST Results for Sequences Encoding Polypeptides Homologous to Homoserine Kinase

| Clone | Status | BLAST pLog Score GI 1591748 (*Methanococcus jannaschii*) |
|---|---|---|
| cr1n.pk0009.g4 | FIS | 19.30 |
| rca1c.pk005.k3 | EST | 15.21 |
| ses8w.pk0020.b5 | FIS | 35.30 |
| wl1n.pk0065.f2 | EST | 5.68 |

The sequence of the entire cDNA insert in clone rca1c.pk005.k3 was determined. The BLASTX search using the EST sequences from clones listed in Table 10 revealed similarity of the polypeptides encoded by the cDNAs to homoserine kinase from *Arabidopsis thaliana* (NCBI General Identifier No. 4927412). Shown in Table 10 are the BLAST results for the sequences of the entire cDNA inserts comprising the indicated cDNA clone ("FIS"):

TABLE 10

BLAST Results for Sequences Encoding Polypeptides Homologous to Homoserine Kinase

| Clone | Status | BLAST pLog Score 4927412 (*Arabidopsis thaliana*) |
|---|---|---|
| rca1c.pk005.k3:fis | FIS | 88.40 |

FIG. 4 presents an alignment of the amino acid sequences set forth in SEQ ID NOs:22, 24, 26, 28, and 59 with the *Methanococcus jannaschii* sequence (NCBI General Identifier No. 1591748; SEQ ID NO:29) and the *Arabidopsis thaliana* sequence (NCBI General Identifier No. 4927412; SEQ ID NO:60). The data in Table 11 presents a calculation of the percent identity of the amino acid sequences set forth in SEQ ID NOs:22, 24, 26, 28, and 59 with the *Methanococcus jannaschii* sequence (NCBI General Identifier No. 1591748; SEQ ID NO:29) and the *Arabidopsis thaliana* sequence (NCBI General Identifier No. 4927412; SEQ ID NO:60).

TABLE 11

Percent Identity of Amino Acid Sequences Deduced From the Nucleotide Sequences of cDNA Clones Encoding Polypeptides Homologous to Homoserine Kinase

| Clone | SEQ ID NO. | Percent Identity to NCBI GI 1591748 | NCBI GI 4927412 |
|---|---|---|---|
| cr1n.pk0009.g4 | 22 | 25.1 | 65.4 |
| rca1c.pk005.k3 | 24 | 48.8 | 67.1 |
| ses8w.pk0020.b5 | 26 | 28.0 | 65.7 |
| wl1n.pk0065.f2 | 28 | 29.8 | 67.9 |
| rca1c.pk005.k3:fis | 59 | 28.6 | 65.9 |

The amino acid sequence set forth in SEQ ID NO:24 is identical to amino acids 18 through 99 of the amino acid sequence set forth in SEQ ID NO:59.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn and a wheat homoserine kinase, a portion and an entire rice homoserine kinase, and an entire soybean homoserine kinase.

Example 6

Characterization of cDNA Clones Encoding Cysteine Synthase

The BLASTX search using the EST sequences from the clone listed in Table 12 revealed similarity of the polypeptides encoded by the cDNAs to cysteine synthase from Citrullus lanatus (DDJB Accession No. D28777, NCBI General Identifier No. 540497). Shown in Table 12 are the BLAST results for the sequences of the entire cDNA inserts comprising the indicated cDNA clones encoding the entire protein ("CGS"):

TABLE 12

BLAST Results for Sequences Encoding Polypeptides Homologous to Cysteine γ Synthase

| Clone | Status | BLAST pLog Score NCBI GI 540497 (*Citrullus lanatus*) |
|---|---|---|
| se3.05h06 | CGS | 182.64 |

Further sequencing and searching of the DuPont proprietary database allowed the identification of corn and rice clones encoding polypeptides with similarites to cysteine γ synthase. The BLAST search using the sequences from clones listed in Table 13 revealed similarity of the polypeptides encoded by the cDNAs to cysteine γ synthase from *Spinacia oleracea* (NCBI General Identifier No. 416869) and *Solanum tuberosum* (NCBI General Identifier No. 11131628). Shown in Table 13 are the BLAST results for the sequences of the entire cDNA inserts comprising the indicated cDNA clones encoding the entire protein ("CGS"):

TABLE 13

BLAST Results for Sequences Encoding Polypeptides Homologous to Cysteine γ Synthase

| | | BLAST pLog Score | |
|---|---|---|---|
| Clone | Status | NCBI GI 416869 (*Spinacia oleracea*) | NCBI GI 11131628 (*Solanum tuberosum*) |
| Contig of:<br>cco1n.pk083.j4<br>chp2.pk0016.b1<br>cpd1c.pk004.b20<br>cr1n.pk0083.c5<br>csi1.pk0003.g6<br>p0126.cnlcb49r | CGS | 158.00 | 157.00 |
| rls6.pk0068.b7:fis | CGS | 161.00 | 163.00 |

FIG. 5 presents an alignment of the amino acid sequences set forth in SEQ ID NOs:31, 62, and 64 with the *Citrullus lanatus* sequence (NCBI General Identifier No. 540497; SEQ ID NO:32), *Spinacia oleracea* (NCBI General Identifier No. 416869; SEQ ID NO:65), and the *Solanum tuberosum* sequence (NCBI General Identifier No. 11131628; SEQ ID NO:66). The data in Table 14 presents a calculation of the percent identity of the amino acid sequences set forth in SEQ ID NOs:31, 62, and 64 with the *Citrullus lanatus* sequence (NCBI General Identifier No. 540497; SEQ ID NO:32), *Spinacia oleracea* (NCBI General Identifier No. 416869; SEQ ID NO:65), and the *Solanum tuberosum* sequence (NCBI General Identifier No. 11131628; SEQ ID NO:66).

TABLE 14

Percent Identity of Amino Acid Sequences Deduced From the Nucleotide Sequences of cDNA Clones Encoding Polypeptides Homologous to Cysteine γ Synthase

| | | Percent Identity to | | |
|---|---|---|---|---|
| Clone | Amino acid SEQ ID NO. | NCBI GI 540497 | NCBI GI 416869 | NCBI GI 11131628 |
| se3.05h06 | 31 | 87.1 | 72.3 | 76.9 |
| Contig of:<br>cco1n.pk083.j4<br>chp2.pk0016.b1<br>cpd1c.pk004.b20<br>cr1n.pk0083.c5<br>csi1.pk0003.g6<br>p0126.cnlcb49r | 62 | 73.8 | 71.3 | 69.7 |
| rls6.pk0068.b7:fis | 64 | 73.2 | 72.6 | 72.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire corn, rice, and soybean cysteine γ synthases. These sequences represent the first corn, rice, and soybean sequences encoding cysteine γ synthase known to Applicant.

Example 7

Characterization of cDNA Clones Encoding Cystathione β-Lyase

The BLASTX search using the EST sequences from clones listed in Table 15 revealed similarity of the polypeptides encoded by the cDNAs to cystathionine β-lyase from *Arabidopsis thaliana* (GenBank Accession No. L40511; NCBI General Identifier No. 1708993). Shown in Table 15 are the BLAST results for individual ESTs ("EST"), the sequences of the entire cDNA inserts comprising the indicated cDNA clones ("FIS"), or the sequences of FISs encoding the entire protein ("CGS"):

TABLE 15

BLAST Results for Sequences Encoding Polypeptides Homologous to Cystathione β-Lyase

| Clone | Status | BLAST pLog Score 1708993 (*A. thaliana*) |
|---|---|---|
| cen1.pk0061.d4 | FIS | 50.41 |
| rlr12.pk0026.g1 | EST | 39.00 |
| sfl1.pk0012.c4 | CGS | 33.85 |
| wr1.pk0091.g6 | EST | 52.52 |

The sequence of the entire cDNA insert in the clone wr1.pk0091.g6 was determined, RACE PCR was used to obtain the 5' portion of the rice cystathionine β-lyase, and further sequencing and searching of the DuPont proprietary database allowed the identification of other corn and wheat clones encoding cystathionine β-lyase. The BLASTX search using the EST sequences from clones listed in Table 16 revealed similarity of the polypeptides encoded by the cDNAs to cystathionine β-lyase from *Arabidopsis thaliana* (GenBank Accession No. L40511; NCBI General Identifier No. 1708993). Shown in Table 16 are the BLAST results for the sequences of the entire cDNA inserts comprising the indicated cDNA clones ("FIS"), or the sequences encoding the entire protein derived from contigs assembled from the sequences of more than two ESTs, the sequence of contigs assembled from the entire cDNA inserts comprising the indicated cDNA clones and 5' RACE PCR or an EST ("Contig*"):

TABLE 16

BLAST Results for Sequences Encoding Polypeptides Homologous to Cystathione β-Lyase

| Clone | Status | BLAST pLog Score 1708993 |
|---|---|---|
| Contig of: cen1.pk0061.d4 p0005.cbmei71r p0014.ctuui39r p0109.cdadg47r p0125.czaay16r | Contig* | >180.00 |
| 5' RACE PCR + rlr12.pk0026.g1:fis | Contig* | 178.00 |
| wr1.pk0091.g6:fis | FIS | 177.00 |

FIG. 6 presents an alignment of the amino acid sequences set forth in SEQ ID NOs:34, 36, 38, 40, 68, 70, and 72 with the *Arabidopsis thaliana* sequence (NCBI General Identifier No. 1708993; SEQ ID NO:41). The data in Table 17 presents a calculation of the percent identity of the amino acid sequences set forth in SEQ ID NOs:34, 36, 38, 40, 68, 70, and 72 with the *Arabidopsis thaliana* sequence (NCBI General Identifier No. 1708993; SEQ ID NO:41).

TABLE 17

Percent Identity of Amino Acid Sequences Deduced From the Nucleotide Sequences of cDNA Clones Encoding Polypeptides Homologous to Cystathione β-Lyase

| Clone | SEQ ID NO. | Percent Identity to 1708993 (*Arabidopsis thaliana*) |
|---|---|---|
| cen1.pk0061.d4 | 34 | 83.0 |
| rlr12.pk0026.g1 | 36 | 76.0 |
| sfl1.pk0012.c4 | 38 | 72.2 |
| wr1.pk0091.g6 | 40 | 71.8 |
| Contig of: cen1.pk0061.d4 p0005.cbmei71r p0014.ctuui39r p0109.cdadg47r p0125.czaay16r | 68 | 66.8 |
| 5' RACE PCR + rlr12.pk0026.g1:fis | 70 | 66.2 |
| wr1.pk0091.g6:fis | 72 | 66.2 |

The amino acid sequence set forth in SEQ ID NO:34 is identical to amino acids 248 through 470 of the amino acid sequence set forth in SEQ ID NO:68. The amino acid sequence set forth in SEQ ID NO:36 is identical to amino acids 152 through 226 of the amino acid sequence set forth in SEQ ID NO:70. The amino acid sequence set forth in SEQ ID NO:40 is identical to amino acids 3 through 133 of the amino acid sequence set forth in SEQ ID NO:72.

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode an entire soybean cystathionine β-lyase, a substantial portion and an entire corn and rice cystathionine β-lyases, a portion and asubstantial portion of a wheat cystathionine β-lyase.

Example 8

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML103 as described below. Amplification is then performed in a standard PCR. The amplified DNA is then digested with restriction enzymes Nco I and Sma I and fractionated on an agarose gel. The appropriate band can be isolated from the gel and combined with a 4.9 kb Nco I-Sma I fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 9

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 10

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 11

Evaluating Compounds for Their Ability to Inhibit the Activity of Plant Biosynthetic Enzymes The polypeptides described herein may be produced using any number of methods known to those skilled in the art. Such methods include, but are not limited to, expression in bacteria as described in Example 10, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. Examples of assays for many of these enzymes can be found in *Methods in Enzymology* Vol. V, (Colowick and Kaplan eds.) Academic Press, New York or *Methods in Enzymology* Vol. XVII, (Tabor and Tabor eds.) Academic Press, New York. Specific examples may be found in the following references, each of which is incorporated herein by reference: aspartic semialdehyde dehydrogenase may be assayed as described in Black et al. (1955) *J. Biol. Chem.* 213:39-50, or Cremer et al. (1988) *J. Gen. Microbiol.* 134:3221-3229; diaminopimelate decarboxylase may be assayed as described in Work (1962) in *Methods in Enzymology* Vol. V, (Colowick and Kaplan eds.) 864-870, Academic Press, New York or Cremer et al. (1988) *J. Gen. Microbiol.* 134:3221-3229; homoserine kinase may be assayed as described in Aarnes (1976) *Plant Sci. Lett.* 7:187-194; cysteine synthase may be assayed as described in Thompson et al. (1968) *Biochem. Biophys. Res. Commun.* 31:281-286 or Bertagnolli et al. (1977) *Plant Physiol.* 60:115-121; and cystathionine β-lyase may be assayed as described in Giovanelli et al. (1971) *Biochim. Biophys. Acta* 227:654-670 or Droux et al. (1995) *Arch. Biochem Biophys.* 316:585-595.

What is claimed is:

1. An isolated polynucleotide that encodes a plant cysteine synthase having amino acid sequence identity of at least 95% based on the Clustal method of alignment when compared to a polypeptide selected from the group consisting of SEQ ID NOs:31, 62, and 64.

2. The polynucleotide of claim 1 wherein the polynucleotide encodes a polypeptide selected from the group consisting of SEQ ID NOs: NOs:31, 62, and 64.

3. The polynucleotide of claim 1, wherein the polynucleotide comprises a nucleotide sequence selected from the group consisting of SEQ ID NO:30, 61, and 63.

4. An isolated complement of the polynucleotide of claim 1, wherein (a) the complement and the polynucleotide consist of the same number of nucleotides, and (b) the nucleotide sequences of the complement and the polynucleotide have 100% complementarity.

5. An isolated nucleic acid molecule that (1) comprises at least 180 nucleotides (2) remains hybridized with a polynucleotide having a nucleotide sequence selected from the group consisting of SEQ ID NO:30, 61, and 63 under a wash condition of 0.1×SSC, 0.1% SDS, and 65° C., and encodes a plant cysteine synthase.

6. A cell comprising the polynucleotide of claim 1.

7. The cell of claim 6, wherein the cell is selected from the group consisting of a yeast cell, a bacterial cell and a plant cell.

8. A transgenic plant comprising the polynucleotide of claim 1.

9. A method for transforming a cell comprising introducing into a cell the polynucleotide of claim 1.

10. A method for producing a transgenic plant comprising (a) transforming a plant cell with the polynucleotide of claim 1, and (b) regenerating a plant from the transformed plant cell.

11. A method for producing a polynucleotide fragment comprising (a) selecting a nucleotide sequence comprised by the polynucleotide of claim 1, and (b) synthesizing a polynucleotide fragment containing the nucleotide sequence.

12. The method of claim 11, wherein the fragment is produced in vivo.

13. A chimeric gene comprising the polynucleotide of claim 1 operably linked to at least one regulatory sequence.

14. A method for altering the level of cysteine synthase expression in a host cell, the method comprising:

(a) Transforming a host cell with the chimeric gene of claim 13; and (b) growing the transformed cell from step (a) under conditions suitable for the expression of the chimeric gene.

* * * * *

```
                               SEQUENCE LISTING

<160> NUMBER OF SEQ ID NOS: 72

<210> SEQ ID NO 1
<211> LENGTH: 826
<212> TYPE: DNA
<213> ORGANISM: Oryza sativa

<400> SEQUENCE: 1

tggtaccgcc acgccaaggt ggtaaggatg gttgtcagca cttaccaagc agcaagtggt     60

gctggggctg cggccatgga agaactcaaa cttcaaactc aagaggtctt ggcggggaaa    120

gcaccaacat gcaacatttt cagtcagcag tatgctttta atatattttc acataatgca    180

ccaattgttg aaaatgggta caatgaggag gagatgaaga tggtgaagga gaccagaaaa    240

atctggaatg ataaagatgt gaaggtaact gcaacctgca tacgagttcc tgtgatgcgt    300

gcacatgctg aaagtgtgaa tctacagttt gaaaagccac ttgatgagga tactgcaagg    360

gaaatcttga gggcagctga aggtgttacc attattgatg accgtgcttc caatcgctt     420

cccacacctc ttgaggtatc ggataaagat gatgtagcag tgggtagaat tcgtcaggat    480

ttgtcgcaag atgataacaa agggctggac atatttgttt gtggagatca aatacgtaaa    540

ggtgctgcac tcaatgctgt gcagattgct gaaatgctac tcaagtgatt ttcttttctg    600

tacctttctc tccttgcccc tctttgctct agtcattgtt tgacggatgt actctggtta    660

gtatgagatc aattttgatc atcttttgta atctatattc ctagtgaaat aaatgtaaaa    720

cggttttgct ctatcttctg cacaagtgta gaagaaatct gaaattggga aattggagtg    780

tggcccttgt tcaaaaaaaa aaaaaaaaaa aaaaaaaaaa aaaaaa                   826


<210> SEQ ID NO 2
<211> LENGTH: 195
<212> TYPE: PRT
<213> ORGANISM: Oryza sativa

<400> SEQUENCE: 2

Trp Tyr Arg His Ala Lys Val Val Arg Met Val Val Ser Thr Tyr Gln
1               5                   10                  15

Ala Ala Ser Gly Ala Gly Ala Ala Ala Met Glu Glu Leu Lys Leu Gln
            20                  25                  30

Thr Gln Glu Val Leu Ala Gly Lys Ala Pro Thr Cys Asn Ile Phe Ser
        35                  40                  45

Gln Gln Tyr Ala Phe Asn Ile Phe Ser His Asn Ala Pro Ile Val Glu
```

```
    50                  55                  60

Asn Gly Tyr Asn Glu Glu Glu Met Lys Met Val Lys Glu Thr Arg Lys
65                  70                  75                  80

Ile Trp Asn Asp Lys Asp Val Lys Val Thr Ala Thr Cys Ile Arg Val
                85                  90                  95

Pro Val Met Arg Ala His Ala Glu Ser Val Asn Leu Gln Phe Glu Lys
            100                 105                 110

Pro Leu Asp Glu Asp Thr Ala Arg Glu Ile Leu Arg Ala Ala Glu Gly
        115                 120                 125

Val Thr Ile Ile Asp Asp Arg Ala Ser Asn Arg Phe Pro Thr Pro Leu
    130                 135                 140

Glu Val Ser Asp Lys Asp Asp Val Ala Val Gly Arg Ile Arg Gln Asp
145                 150                 155                 160

Leu Ser Gln Asp Asp Asn Lys Gly Leu Asp Ile Phe Val Cys Gly Asp
                165                 170                 175

Gln Ile Arg Lys Gly Ala Ala Leu Asn Ala Val Gln Ile Ala Glu Met
            180                 185                 190

Leu Leu Lys
        195


<210> SEQ ID NO 3
<211> LENGTH: 875
<212> TYPE: DNA
<213> ORGANISM: Triticum aestivum

<400> SEQUENCE: 3

cctcatggct gtcacgccgc tgcatcgcca cgccaaggtg aaaaggatgg ttgtcagcac      60

ataccaagca gcaagtggtg ctggtgctgc agccatggaa gaactcaaac ttcagactcg     120

agaggtcttg gaaggaaagc caccaacctg taacattttc agtcaacagt atgcttttaa     180

tatattttcg cataatgcac ctattgttga aaatggctat aatgaggaag agatgaaaat     240

ggtgaaggag accagaaaaa tctggaatga caaggatgta agagtaactg caacttgtat     300

acgggttcct acgatgcgcg cgcatgccga aagcgtgaat ctacagtttg aaaagccact     360

tgatgaggac actgccagag aaatcttgag ggcagctcct ggtgttacca ttagtgacga     420

ccgtgctgcc aaccgcttcc ctacaccact ggaggtatcg gataaagatg acgtatcagt     480

tggtaggatt cgccaggact tgtcacaaga tgataacaga gggttggagt tatttgtctg     540

tggagaccag atacgtaaag gcgccgcgct gaacgctgtg cagattgctg aaatgctact     600

gaagtgaccg cctttttacc attgtctcat gtgccacgtt gctctatcca ttgatggatt     660

gatgtactct agtcactttc aacccagttt tggtcgtcgt ctttttttgta atctgtcaac     720

ctagcagaag aagtgtaaga cgggctttag tcatctgttg cacacaaaag tgcagccaca     780

agtttagaaa aggagggttt tcacttgttc ggattttgcc ttaggttgga ctttgttgca     840

agttgtcgtt tgtttcttga aagctggtct gctgt                                875


<210> SEQ ID NO 4
<211> LENGTH: 201
<212> TYPE: PRT
<213> ORGANISM: Triticum aestivum

<400> SEQUENCE: 4

Leu Met Ala Val Thr Pro Leu His Arg His Ala Lys Val Lys Arg Met
1               5                   10                  15

Val Val Ser Thr Tyr Gln Ala Ala Ser Gly Ala Gly Ala Ala Ala Met
```

-continued

```
            20                  25                  30

Glu Glu Leu Lys Leu Gln Thr Arg Glu Val Leu Glu Gly Lys Pro Pro
        35                  40                  45

Thr Cys Asn Ile Phe Ser Gln Gln Tyr Ala Phe Asn Ile Phe Ser His
    50                  55                  60

Asn Ala Pro Ile Val Glu Asn Gly Tyr Asn Glu Glu Glu Met Lys Met
65                  70                  75                  80

Val Lys Glu Thr Arg Lys Ile Trp Asn Asp Lys Asp Val Arg Val Thr
                85                  90                  95

Ala Thr Cys Ile Arg Val Pro Thr Met Arg Ala His Ala Glu Ser Val
            100                 105                 110

Asn Leu Gln Phe Glu Lys Pro Leu Asp Glu Asp Thr Ala Arg Glu Ile
        115                 120                 125

Leu Arg Ala Ala Pro Gly Val Thr Ile Ser Asp Asp Arg Ala Ala Asn
    130                 135                 140

Arg Phe Pro Thr Pro Leu Glu Val Ser Asp Lys Asp Asp Val Ser Val
145                 150                 155                 160

Gly Arg Ile Arg Gln Asp Leu Ser Gln Asp Asp Asn Arg Gly Leu Glu
                165                 170                 175

Leu Phe Val Cys Gly Asp Gln Ile Arg Lys Gly Ala Ala Leu Asn Ala
            180                 185                 190

Val Gln Ile Ala Glu Met Leu Leu Lys
        195                 200


<210> SEQ ID NO 5
<211> LENGTH: 457
<212> TYPE: DNA
<213> ORGANISM: Glycine max
<220> FEATURE:
<221> NAME/KEY: unsure
<222> LOCATION: (211)
<223> OTHER INFORMATION: n = A, C, G or T
<220> FEATURE:
<221> NAME/KEY: unsure
<222> LOCATION: (320
<223> OTHER INFORMATION: n = A, C, G or T
<220> FEATURE:
<221> NAME/KEY: unsure
<222> LOCATION: (377)
<223> OTHER INFORMATION: n = A, C, G or T
<220> FEATURE:
<221> NAME/KEY: unsure
<222> LOCATION: (391)   (392)
<223> OTHER INFORMATION: n = A, C, G or T
<220> FEATURE:
<221> NAME/KEY: unsure
<222> LOCATION: (410
<223> OTHER INFORMATION: n = A, C, G or T
<220> FEATURE:
<221> NAME/KEY: unsure
<222> LOCATION: (420
<223> OTHER INFORMATION: n = A, C, G or T
<220> FEATURE:
<221> NAME/KEY: unsure
<222> LOCATION: (428
<223> OTHER INFORMATION: n = A, C, G or T
<220> FEATURE:
<221> NAME/KEY: unsure
<222> LOCATION: (432)
<223> OTHER INFORMATION: n = A, C, G or T
<220> FEATURE:
<221> NAME/KEY: unsure
<222> LOCATION: (434)
<223> OTHER INFORMATION: n = A, C, G or T
<220> FEATURE:
<221> NAME/KEY: unsure
<222> LOCATION: (438
```

-continued

<223> OTHER INFORMATION: n = A, C, G or T
<220> FEATURE:
<221> NAME/KEY: unsure
<222> LOCATION: (442
<223> OTHER INFORMATION: n = A, C, G or T
<220> FEATURE:
<221> NAME/KEY: unsure
<222> LOCATION: (451)
<223> OTHER INFORMATION: n = A, C, G or T

<400> SEQUENCE: 5

```
gtctgtttta aaatccaaca cttaatctct ctcttcgcag cctaaaatcc caatggcttc     60

actctctgtt ttgcgccaca accacctctt ctcgggcccc ctcccggccc gccccaagcc    120

cacctcctcc tcctcctcca ggatccgaat gtccctccgc gagaacggcc cctccatcgc    180

cgtcgtgggc gtcaccggcg ccgtcggcca ngagttcctc tccgtcctct ccgaccgcga    240

cttcccctac cgctccattc atatgctggc ttccaagcgc tccgctggac gccgcatcac    300

cttcgaggac agggactacn tcttcaggag ctcacgccgg agagttcgac ggtgtcgaca    360

tcgcgctctt cagcgcnggg ggtccatcaa nnaagcattc ggaccatcgn cgtaaatcgn    420

gggacggncg tngncaanat anctccggtt ncctttg                             457
```

<210> SEQ ID NO 6
<211> LENGTH: 86
<212> TYPE: PRT
<213> ORGANISM: Glycine max

<400> SEQUENCE: 6

```
Met Ala Ser Leu Ser Val Leu Arg His Asn His Leu Phe Ser Gly Pro
1               5                   10                  15

Leu Pro Ala Arg Pro Lys Pro Thr Ser Ser Ser Ser Ser Arg Ile Arg
            20                  25                  30

Met Ser Leu Arg Glu Asn Gly Pro Ser Ile Ala Val Val Gly Val Thr
        35                  40                  45

Gly Ala Val Gly Gln Glu Phe Leu Ser Val Leu Ser Asp Arg Asp Phe
    50                  55                  60

Pro Tyr Arg Ser Ile His Met Leu Ala Ser Lys Arg Ser Ala Gly Arg
65                  70                  75                  80

Arg Ile Thr Phe Glu Asp
                85
```

<210> SEQ ID NO 7
<211> LENGTH: 160
<212> TYPE: PRT
<213> ORGANISM: Legionella pneumophila

<400> SEQUENCE: 7

```
Met Ser Arg His Leu Asn Val Ala Ile Val Gly Ala Thr Gly Ala Val
1               5                   10                  15

Gly Glu Thr Phe Leu Thr Val Leu Glu Glu Arg Asn Phe Pro Ile Lys
            20                  25                  30

Ser Leu Tyr Pro Leu Ala Ser Ser Arg Ser Val Gly Lys Thr Val Thr
        35                  40                  45

Phe Arg Asp Gln Glu Leu Asp Val Leu Asp Leu Ala Glu Phe Asp Phe
    50                  55                  60

Ser Lys Val Asp Leu Ala Leu Phe Ser Ala Gly Gly Ala Val Ser Lys
65                  70                  75                  80

Glu Tyr Ala Pro Lys Ala Val Ala Ala Gly Cys Val Val Val Asp Asn
                85                  90                  95
```

-continued

```
Thr Ser Cys Phe Arg Tyr Glu Asp Asp Ile Pro Leu Val Val Pro Gly
            100                 105                 110

Ser Glu Ser Ser Ser Asn Arg Asp Tyr Thr Lys Arg Gly Ile Ile Ala
        115                 120                 125

Asn Pro Asn Cys Ser Thr Ile Gln Met Val Val Ala Leu Lys Pro Ile
    130                 135                 140

Tyr Asp Ala Val Gly Ile Ser Arg Ile Asn Val Ala Thr Tyr Gln Ser
145                 150                 155                 160


<210> SEQ ID NO 8
<211> LENGTH: 1054
<212> TYPE: DNA
<213> ORGANISM: Zea mays

<400> SEQUENCE: 8

atttaacgga aatgggaaga cactcgaaca tcttaaatta gctgctgaga gtggagtatt      60

tgtaaatgtg gatagcgaat ttgatttgga gaatattgtc agagctgcaa gagctactgg     120

aaagaaagtg cctgttttgc ttcgaataaa tccagatgtg gatccgcagg tacatcctta     180

tgttgccacg ggaaataaaa cgtctaaatt tgggatccgc aatgagaaat tgcaatggtt     240

tttggactct atcaagtcat acccgaatga aatcaaactc gttggtgttc attgccatct     300

gggatctact attacaaagg ttgatatatt cagagatgct gcagttctta tgctgaatta     360

tgtcgatgaa attcgagcac aaggttttaa gttggagtac ctgaatatcg gaggtggttt     420

gggaatagat taccatcata ccgatgcagt cttacctaca cctatggatc tcatcaacac     480

tgtgcgagaa ttagttctct ctcaagatct cactcttatt attgaacccg gaagatcctt     540

gattgctaat acttgctgct tcgtcaatag agtaactggt gttaaatcta atggtacaaa     600

gaatttcatt gttgttgatg gcagcatggc agaactcatc agacctagtc tgtatggagc     660

ataccagcat atcgaactgg tctctccccc cactcctggt gctgaagcag cgaccttcga     720

tattgttgga ccagtttgtg agtctgcaga tttccttgga aaagataggg aacttccaac     780

acctgatgag ggagctggac tggttgttca tgatgcaggt gcctactgca tgagcatggc     840

ttccacctac aacctgaagt tgaggccacc ggaatactgg gtggaagcgg acggttcgat     900

cgttaagatc aggcatggag agaagcttga tgactacatg aagttctttg atggtcttcc     960

tgcttagatg tttattatct gcgactgcta cggacgatgt tttcttgggg ataattggat    1020

tttctttgtc aaaaaaaaaa aaaaaaaaaa aaaa                                1054


<210> SEQ ID NO 9
<211> LENGTH: 321
<212> TYPE: PRT
<213> ORGANISM: Zea mays

<400> SEQUENCE: 9

Phe Asn Gly Asn Gly Lys Thr Leu Glu His Leu Lys Leu Ala Ala Glu
1               5                   10                  15

Ser Gly Val Phe Val Asn Val Asp Ser Glu Phe Asp Leu Glu Asn Ile
            20                  25                  30

Val Arg Ala Ala Arg Ala Thr Gly Lys Lys Val Pro Val Leu Leu Arg
        35                  40                  45

Ile Asn Pro Asp Val Asp Pro Gln Val His Pro Tyr Val Ala Thr Gly
    50                  55                  60

Asn Lys Thr Ser Lys Phe Gly Ile Arg Asn Glu Lys Leu Gln Trp Phe
65                  70                  75                  80
```

-continued

```
Leu Asp Ser Ile Lys Ser Tyr Pro Asn Glu Ile Lys Leu Val Gly Val
                85                  90                  95

His Cys His Leu Gly Ser Thr Ile Thr Lys Val Asp Ile Phe Arg Asp
            100                 105                 110

Ala Ala Val Leu Met Leu Asn Tyr Val Asp Glu Ile Arg Ala Gln Gly
        115                 120                 125

Phe Lys Leu Glu Tyr Leu Asn Ile Gly Gly Gly Leu Gly Ile Asp Tyr
    130                 135                 140

His His Thr Asp Ala Val Leu Pro Thr Pro Met Asp Leu Ile Asn Thr
145                 150                 155                 160

Val Arg Glu Leu Val Leu Ser Gln Asp Leu Thr Leu Ile Ile Glu Pro
                165                 170                 175

Gly Arg Ser Leu Ile Ala Asn Thr Cys Cys Phe Val Asn Arg Val Thr
            180                 185                 190

Gly Val Lys Ser Asn Gly Thr Lys Asn Phe Ile Val Val Asp Gly Ser
        195                 200                 205

Met Ala Glu Leu Ile Arg Pro Ser Leu Tyr Gly Ala Tyr Gln His Ile
    210                 215                 220

Glu Leu Val Ser Pro Pro Thr Pro Gly Ala Glu Ala Ala Thr Phe Asp
225                 230                 235                 240

Ile Val Gly Pro Val Cys Glu Ser Ala Asp Phe Leu Gly Lys Asp Arg
                245                 250                 255

Glu Leu Pro Thr Pro Asp Glu Gly Ala Gly Leu Val Val His Asp Ala
            260                 265                 270

Gly Ala Tyr Cys Met Ser Met Ala Ser Thr Tyr Asn Leu Lys Leu Arg
        275                 280                 285

Pro Pro Glu Tyr Trp Val Glu Ala Asp Gly Ser Ile Val Lys Ile Arg
    290                 295                 300

His Gly Glu Lys Leu Asp Asp Tyr Met Lys Phe Phe Asp Gly Leu Pro
305                 310                 315                 320

Ala


<210> SEQ ID NO 10
<211> LENGTH: 1813
<212> TYPE: DNA
<213> ORGANISM: Zea mays

<400> SEQUENCE: 10

cgcttcctgg aaggctggaa cagaaagaac cctaaaccct agcaatggcg gcggcgaacc     60

tgctgtcgcg ctcccttctc cccaccccaa acactatccg aacgagccac cccaccccgc    120

ggagcccagc cgtcgtctcc ttcccccgcc gccgtgcccg cctgtccgtg tgcgcctccg    180

tctccatggc ctccccgtcc ccaccgccac agcccgcggc ggccggcgtg ccgaagcact    240

gcttccggcg cggcgccgac ggctacctgt actgcgaggg agtgagggtg gaagacgcga    300

tggcggctgc cgagcgcagc cccttctatc tctacagcaa gcttcagatc ctccgcaact    360

tcgccgctta ccgcgacgct ctccaggggc tccgctccat cgtcgggtat gccgtgaagg    420

ccaacaataa cctccccgtg ctacgcgtcc tgcgtgagct tggctgcggc gccgtcctcg    480

tcagcggcaa cgagctccga ctcgccctcc aggcgggatt cgaccccgcc aggtgtatat    540

ttaacggaaa tgggaagaca ctcgaagatc ttaaattggc tgctgagagt ggagtatttg    600

taaatgtgga tagtgaattt gatttagaga atattgtcag agctgcaaga gctactggaa    660

agaaagtgcc tgttttactt agaataaatc cagatgtgga tccacaggta catccatatg    720
```

```
ttgccacggg aaataaaaca tccaaattcg ggatccgcaa tgagaaattg caatggtttt    780

tgaactctat caagtcatac tcgaatgaaa tcaaactcgt tggtgttcat tgccatctgg    840

gatctactat tacaaaggtt gatatattca gagatgctgc agtgcttatg gtgaattatg    900

tcgatgaaat tcgagcacaa ggttttaagt tggagtacct gaatattgga ggtggtttgg    960

gaatagatta ccatcatacc gatgcagtct tacctacacc tatggatctc atcaacactg   1020

tacgagaatt agttctctct caagatctta ctcttattat tgaacctgga agatccttga   1080

ttgctaatac ttgctgcttc gtcaatagag taactggtgt taaatctaat ggtacaaaga   1140

atttcattgt tgttgatggc agcatggcag aactcatcag acctagcctg tatggagcat   1200

atcagcatat cgaattggtc tctcccccca ctcctggtgc tgaagtagcg accttcgata   1260

ttgttgggcc agtttgtgag tctgcagatt tccttggaaa agatagggaa cttccaacac   1320

ctgatgaggg agctggactg gttgttcatg atgcaggtgc ctactgcatg agcatggctt   1380

ccacctacaa cctgaagttg aggccgccag agtactgggt tgaagaggat ggttcgattg   1440

ttaagatcag gcatgaagag aagctcgatg actacatgaa gttctttgat ggtcttcctg   1500

cttagatgtt tatttgtgac tgctaggggc gatgttttct tggagataat tgaatttttc   1560

tttgtcaagc tcattttgct ttcttgtggt tgttatggaa tgttactgga tactggatag   1620

ttagttcggc ctgtaggcgt atcctcctga acttacctct cattgctgtt agttttggca   1680

ccaagtttgt tcccaattgc tatttacgga agttattgca taaagggctg tttggttgta   1740

atcttcccgt aagaataaga tgcatgtttt tgagttaaaa aaggggggc ccggtaccca    1800

attcgcccta tag                                                      1813
```

```
<210> SEQ ID NO 11
<211> LENGTH: 486
<212> TYPE: PRT
<213> ORGANISM: Zea mays

<400> SEQUENCE: 11

Met Ala Ala Ala Asn Leu Leu Ser Arg Ser Leu Leu Pro Thr Pro Asn
1               5                   10                  15

Thr Ile Arg Thr Ser His Pro Thr Pro Arg Ser Pro Ala Val Val Ser
            20                  25                  30

Phe Pro Arg Arg Arg Ala Arg Leu Ser Val Cys Ala Ser Val Ser Met
        35                  40                  45

Ala Ser Pro Ser Pro Pro Pro Gln Pro Ala Ala Ala Gly Val Pro Lys
    50                  55                  60

His Cys Phe Arg Arg Gly Ala Asp Gly Tyr Leu Tyr Cys Glu Gly Val
65                  70                  75                  80

Arg Val Glu Asp Ala Met Ala Ala Ala Glu Arg Ser Pro Phe Tyr Leu
                85                  90                  95

Tyr Ser Lys Leu Gln Ile Leu Arg Asn Phe Ala Ala Tyr Arg Asp Ala
            100                 105                 110

Leu Gln Gly Leu Arg Ser Ile Val Gly Tyr Ala Val Lys Ala Asn Asn
        115                 120                 125

Asn Leu Pro Val Leu Arg Val Leu Arg Glu Leu Gly Cys Gly Ala Val
    130                 135                 140

Leu Val Ser Gly Asn Glu Leu Arg Leu Ala Leu Gln Ala Gly Phe Asp
145                 150                 155                 160

Pro Ala Arg Cys Ile Phe Asn Gly Asn Gly Lys Thr Leu Glu Asp Leu
                165                 170                 175
```

```
Lys Leu Ala Ala Glu Ser Gly Val Phe Val Asn Val Asp Ser Glu Phe
            180                 185                 190

Asp Leu Glu Asn Ile Val Arg Ala Ala Arg Ala Thr Gly Lys Lys Val
        195                 200                 205

Pro Val Leu Leu Arg Ile Asn Pro Asp Val Asp Pro Gln Val His Pro
    210                 215                 220

Tyr Val Ala Thr Gly Asn Lys Thr Ser Lys Phe Gly Ile Arg Asn Glu
225                 230                 235                 240

Lys Leu Gln Trp Phe Leu Asn Ser Ile Lys Ser Tyr Ser Asn Glu Ile
                245                 250                 255

Lys Leu Val Gly Val His Cys His Leu Gly Ser Thr Ile Thr Lys Val
            260                 265                 270

Asp Ile Phe Arg Asp Ala Ala Val Leu Met Val Asn Tyr Val Asp Glu
        275                 280                 285

Ile Arg Ala Gln Gly Phe Lys Leu Glu Tyr Leu Asn Ile Gly Gly Gly
    290                 295                 300

Leu Gly Ile Asp Tyr His His Thr Asp Ala Val Leu Pro Thr Pro Met
305                 310                 315                 320

Asp Leu Ile Asn Thr Val Arg Glu Leu Val Leu Ser Gln Asp Leu Thr
                325                 330                 335

Leu Ile Ile Glu Pro Gly Arg Ser Leu Ile Ala Asn Thr Cys Cys Phe
            340                 345                 350

Val Asn Arg Val Thr Gly Val Lys Ser Asn Gly Thr Lys Asn Phe Ile
        355                 360                 365

Val Val Asp Gly Ser Met Ala Glu Leu Ile Arg Pro Ser Leu Tyr Gly
    370                 375                 380

Ala Tyr Gln His Ile Glu Leu Val Ser Pro Pro Thr Pro Gly Ala Glu
385                 390                 395                 400

Val Ala Thr Phe Asp Ile Val Gly Pro Val Cys Glu Ser Ala Asp Phe
                405                 410                 415

Leu Gly Lys Asp Arg Glu Leu Pro Thr Pro Asp Glu Gly Ala Gly Leu
            420                 425                 430

Val Val His Asp Ala Gly Ala Tyr Cys Met Ser Met Ala Ser Thr Tyr
        435                 440                 445

Asn Leu Lys Leu Arg Pro Pro Glu Tyr Trp Val Glu Glu Asp Gly Ser
    450                 455                 460

Ile Val Lys Ile Arg His Glu Glu Lys Leu Asp Asp Tyr Met Lys Phe
465                 470                 475                 480

Phe Asp Gly Leu Pro Ala
                485
```

<210> SEQ ID NO 12
<211> LENGTH: 1116
<212> TYPE: DNA
<213> ORGANISM: Oryza sativa

<400> SEQUENCE: 12

```
cttacacgga gtgtttgtaa acatagacag tgaatttgat ttggagaata ttgtcactgc      60

tgcgagagtt gctgggaaga aagtccctgt tttgctcagg ataaacccag atgtggatcc     120

acaggtccat ccttatgttg cgactggaaa caaaacctcc aaatttggta tccgtaatga     180

gaaactacaa tggttcttag actctatcaa gtcatactca aatgatatca cactggtggg     240

tgttcattgt catctgggat ctaccattac aaaggtcgat atatttagag atgcggcagg     300
```

-continued

```
tcttatggtg aattatgttg atgaaattcg agcacaaggt tttgaactgg aatatctcaa    360

tattggcggt ggcctgggca tagwttatca ccacacggat gcagtcttgc ctacacctat    420

gggacctcat caacactgtg ccgaagaatt agttctgtca cgagatctta cactcatcat    480

tgaacctggg agatccctca tagctaacac ttgctgcttc gtcaataggg tcactggtgt    540

taaatctaat ggtacaaaga atttcattgt agttgatggc agcatggcag agcttatcag    600

accaagtcta tatggagcat accagcatat cgaactggtt tctccttccc cagatgcaga    660

agtagcaaca ttcgatattg ttggaccagt ttgtgaatct gcagatttcc ttggcaaaga    720

cagggaactt ccaacacctg ataagggagc tggtttggtg gttcatgacg caggagccta    780

ctgcatgagc atggcttcaa cctacaactt gaagttgcga ccacctgaat attgggtaga    840

agatgatggg tccattgcta agattcggcg tggagagtca tttgatgact acatgaagtt    900

ctttgataat ctctctgcct aactcgtttt cctgcaattg taataagatt tttctcttgt    960

tatgtgtggc tgtatcagga ttcggattga tagcgcagta cagtttgctg tagaatcggt   1020

attttttttt attgtactgt gatgtcggta ccttatttta tccaaagatt tttggcaaat   1080

tttgctacag gacacttaaa aaaaaaaaaa aaaaaa                              1116
```

```
<210> SEQ ID NO 13
<211> LENGTH: 306
<212> TYPE: PRT
<213> ORGANISM: Oryza sativa
<220> FEATURE:
<221> NAME/KEY: UNSURE
<222> LOCATION: (128)
<223> OTHER INFORMATION: Xaa = ANY AMINO ACID

<400> SEQUENCE: 13

Leu His Gly Val Phe Val Asn Ile Asp Ser Glu Phe Asp Leu Glu Asn
1               5                   10                  15

Ile Val Thr Ala Ala Arg Val Ala Gly Lys Lys Val Pro Val Leu Leu
            20                  25                  30

Arg Ile Asn Pro Asp Val Asp Pro Gln Val His Pro Tyr Val Ala Thr
        35                  40                  45

Gly Asn Lys Thr Ser Lys Phe Gly Ile Arg Asn Glu Lys Leu Gln Trp
    50                  55                  60

Phe Leu Asp Ser Ile Lys Ser Tyr Ser Asn Asp Ile Thr Leu Val Gly
65                  70                  75                  80

Val His Cys His Leu Gly Ser Thr Ile Thr Lys Val Asp Ile Phe Arg
                85                  90                  95

Asp Ala Ala Gly Leu Met Val Asn Tyr Val Asp Glu Ile Arg Ala Gln
            100                 105                 110

Gly Phe Glu Leu Glu Tyr Leu Asn Ile Gly Gly Gly Leu Gly Ile Xaa
        115                 120                 125

Tyr His His Thr Asp Ala Val Leu Pro Thr Pro Met Gly Pro His Gln
    130                 135                 140

His Cys Ala Glu Glu Leu Val Leu Ser Arg Asp Leu Thr Leu Ile Ile
145                 150                 155                 160

Glu Pro Gly Arg Ser Leu Ile Ala Asn Thr Cys Cys Phe Val Asn Arg
                165                 170                 175

Val Thr Gly Val Lys Ser Asn Gly Thr Lys Asn Phe Ile Val Val Asp
            180                 185                 190

Gly Ser Met Ala Glu Leu Ile Arg Pro Ser Leu Tyr Gly Ala Tyr Gln
        195                 200                 205
```

-continued

```
His Ile Glu Leu Val Ser Pro Ser Pro Asp Ala Glu Val Ala Thr Phe
    210                 215                 220

Asp Ile Val Gly Pro Val Cys Glu Ser Ala Asp Phe Leu Gly Lys Asp
225                 230                 235                 240

Arg Glu Leu Pro Thr Pro Asp Lys Gly Ala Gly Leu Val Val His Asp
                245                 250                 255

Ala Gly Ala Tyr Cys Met Ser Met Ala Ser Thr Tyr Asn Leu Lys Leu
            260                 265                 270

Arg Pro Pro Glu Tyr Trp Val Glu Asp Asp Gly Ser Ile Ala Lys Ile
        275                 280                 285

Arg Arg Gly Glu Ser Phe Asp Asp Tyr Met Lys Phe Phe Asp Asn Leu
    290                 295                 300

Ser Ala
305


<210> SEQ ID NO 14
<211> LENGTH: 968
<212> TYPE: DNA
<213> ORGANISM: Glycine max

<400> SEQUENCE: 14

gttgccactg ggaataagaa ctctaaattt ggcattagaa atgagaagct gcagtgcttt      60

ttagatgcag tgaaggaaca tcctaatgag ctcaaacttg taggggccca ctgccatctt     120

ggttcaacaa ttaccaaggt tgacattttc agggatgcag ccaccattat gatcaactac     180

attgaccaaa tccgagatca gggttttgaa gttgattact taaatattgg tggaggactt     240

gggatagatt attatcattc tggtgccatc cttcctacac ctagagatct cattgacact     300

gtacgagatc ttgttatttc acgtggtctt aatctcatca ttgaaccagg aagatcactc     360

attgcaaaca cgtgttgctt agttaaccgg gtgacaggtg ttaaaactaa tggatctaaa     420

aacttcattg taattgatgg aagtatggct gaacttatcc gccctagtct ttatgatgct     480

taccagcata tagagctggt ttcccctgcc ccgtcaaatg ctgaaacaga aacttttgat     540

gtggttggcc ctgtctgtga gtctgcagat ttcttaggaa aaggaagaga acttcctact     600

ccagccaagg gtactggttt ggttgttcat gatgctggtg cttattgcat gagcatggca     660

tcaacctaca atctaaagat gcggcctcct gagtattggg ttgaagatga tggatcagtg     720

agcaaaataa gacatggaga gacttttgaa gaccacattc ggtttttga ggggctttga      780

gctaataatt tatcttgtag gaaagaaggc tggagaattg ttatgtactt ggagtttgaa     840

tctttcctcg tcaatgaatg catgactctt gtagttctgt ttcttccgtt ctaattgaat     900

gttgactccc atgacaggaa cagagaataa agttgatttc agttagattt aaaaaaaaaa     960

aaaaaaaa                                                              968


<210> SEQ ID NO 15
<211> LENGTH: 259
<212> TYPE: PRT
<213> ORGANISM: Glycine max

<400> SEQUENCE: 15

Val Ala Thr Gly Asn Lys Asn Ser Lys Phe Gly Ile Arg Asn Glu Lys
1               5                   10                  15

Leu Gln Cys Phe Leu Asp Ala Val Lys Glu His Pro Asn Glu Leu Lys
            20                  25                  30

Leu Val Gly Ala His Cys His Leu Gly Ser Thr Ile Thr Lys Val Asp
        35                  40                  45
```

```
Ile Phe Arg Asp Ala Ala Thr Ile Met Ile Asn Tyr Ile Asp Gln Ile
    50                  55                  60

Arg Asp Gln Gly Phe Glu Val Asp Tyr Leu Asn Ile Gly Gly Gly Leu
65                  70                  75                  80

Gly Ile Asp Tyr Tyr His Ser Gly Ala Ile Leu Pro Thr Pro Arg Asp
                85                  90                  95

Leu Ile Asp Thr Val Arg Asp Leu Val Ile Ser Arg Gly Leu Asn Leu
            100                 105                 110

Ile Ile Glu Pro Gly Arg Ser Leu Ile Ala Asn Thr Cys Cys Leu Val
        115                 120                 125

Asn Arg Val Thr Gly Val Lys Thr Asn Gly Ser Lys Asn Phe Ile Val
    130                 135                 140

Ile Asp Gly Ser Met Ala Glu Leu Ile Arg Pro Ser Leu Tyr Asp Ala
145                 150                 155                 160

Tyr Gln His Ile Glu Leu Val Ser Pro Ala Pro Ser Asn Ala Glu Thr
                165                 170                 175

Glu Thr Phe Asp Val Val Gly Pro Val Cys Glu Ser Ala Asp Phe Leu
            180                 185                 190

Gly Lys Gly Arg Glu Leu Pro Thr Pro Ala Lys Gly Thr Gly Leu Val
        195                 200                 205

Val His Asp Ala Gly Ala Tyr Cys Met Ser Met Ala Ser Thr Tyr Asn
    210                 215                 220

Leu Lys Met Arg Pro Pro Glu Tyr Trp Val Glu Asp Asp Gly Ser Val
225                 230                 235                 240

Ser Lys Ile Arg His Gly Glu Thr Phe Glu Asp His Ile Arg Phe Phe
                245                 250                 255

Glu Gly Leu
```

```
<210> SEQ ID NO 16
<211> LENGTH: 676
<212> TYPE: DNA
<213> ORGANISM: Triticum aestivum
<220> FEATURE:
<221> NAME/KEY: unsure
<222> LOCATION: (373)
<223> OTHER INFORMATION: n = A, C, G or T
<220> FEATURE:
<221> NAME/KEY: unsure
<222> LOCATION: (406)
<223> OTHER INFORMATION: n = A, C, G or T
<220> FEATURE:
<221> NAME/KEY: unsure
<222> LOCATION: (430)
<223> OTHER INFORMATION: n = A, C, G or T
<220> FEATURE:
<221> NAME/KEY: unsure
<222> LOCATION: (433)
<223> OTHER INFORMATION: n = A, C, G or T
<220> FEATURE:
<221> NAME/KEY: unsure
<222> LOCATION: (455)
<223> OTHER INFORMATION: n = A, C, G or T
<220> FEATURE:
<221> NAME/KEY: unsure
<222> LOCATION: (494)
<223> OTHER INFORMATION: n = A, C, G or T
<220> FEATURE:
<221> NAME/KEY: unsure
<222> LOCATION: (504)
<223> OTHER INFORMATION: n = A, C, G or T
<220> FEATURE:
<221> NAME/KEY: unsure
<222> LOCATION: (553)
<223> OTHER INFORMATION: n = A, C, G or T
```

<220> FEATURE:
<221> NAME/KEY: unsure
<222> LOCATION: (579)
<223> OTHER INFORMATION: n = A, C, G or T
<220> FEATURE:
<221> NAME/KEY: unsure
<222> LOCATION: (583)
<223> OTHER INFORMATION: n = A, C, G or T
<220> FEATURE:
<221> NAME/KEY: unsure
<222> LOCATION: (595)..(596)
<223> OTHER INFORMATION: n = A, C, G or T
<220> FEATURE:
<221> NAME/KEY: unsure
<222> LOCATION: (620)
<223> OTHER INFORMATION: n = A, C, G or T
<220> FEATURE:
<221> NAME/KEY: unsure
<222> LOCATION: (639)
<223> OTHER INFORMATION: n = A, C, G or T
<220> FEATURE:
<221> NAME/KEY: unsure
<222> LOCATION: (644)
<223> OTHER INFORMATION: n = A, C, G or T
<220> FEATURE:
<221> NAME/KEY: unsure
<222> LOCATION: (650)
<223> OTHER INFORMATION: n = A, C, G or T
<220> FEATURE:
<221> NAME/KEY: unsure
<222> LOCATION: (661)
<223> OTHER INFORMATION: n = A, C, G or T
<220> FEATURE:
<221> NAME/KEY: unsure
<222> LOCATION: (673)
<223> OTHER INFORMATION: n = A, C, G or T

<400> SEQUENCE: 16

```
tttgagttgg agtacctgaa tattggaggt ggtttgggga tagactacca ccacactggt     60

gcagtcttgc ctacacctat ggatcttatc aacactgtcc gggaattggt cctctcacgg    120

gatcttactc tcattattga acctggaaga tccctgatcg ccaatacttg ctgcttcgtc    180

aataaggtca ctggtgtaaa atcgaatggc acgaagaatt tcattgtagt tgatggcagc    240

atggccgagc tcatcaggcc tagtctatat ggagcatatc agcatataga actagttctc    300

cctctccaag gtgcagaagt agcaaccttc cgatattgtt ggggccagtc tgcgaatctg    360

cagattcctt ggnaaagaca aggagttcca acacctgaca aggganctgg tttgggtgtc    420

cacgacgcan ganctactgc atgagcatgg cttcnaccta caacctgaag atgaggcaac    480

cgagtattgg gtanaggaca tggnccatgt aagataagca cggggaaaca ttgacgacac    540

atgagtcttg atngctccgc caggccttta ctggttggna acnagcttca ttgtnnccac    600

cgtggaatct gggaacatcn tgttgtagtg gcaccacana gggnttttgn gacaatcaca    660

ntagatgaga ttntgg                                                    676
```

<210> SEQ ID NO 17
<211> LENGTH: 73
<212> TYPE: PRT
<213> ORGANISM: Triticum aestivum

<400> SEQUENCE: 17

```
Pro Thr Pro Met Asp Leu Ile Asn Thr Val Arg Glu Leu Val Leu Ser
1               5                   10                  15

Arg Asp Leu Thr Leu Ile Ile Glu Pro Gly Arg Ser Leu Ile Ala Asn
            20                  25                  30

Thr Cys Cys Phe Val Asn Lys Val Thr Gly Val Lys Ser Asn Gly Thr
        35                  40                  45
```

```
Lys Asn Phe Ile Val Val Asp Gly Ser Met Ala Glu Leu Ile Arg Pro
    50                  55                  60

Ser Leu Tyr Gly Ala Tyr Gln His Ile
65                  70


<210> SEQ ID NO 18
<211> LENGTH: 544
<212> TYPE: DNA
<213> ORGANISM: Glycine max
<220> FEATURE:
<221> NAME/KEY: unsure
<222> LOCATION: (465)
<223> OTHER INFORMATION: n = A, C, G or T
<220> FEATURE:
<221> NAME/KEY: unsure
<222> LOCATION: (524)
<223> OTHER INFORMATION: n = A, C, G or T
<220> FEATURE:
<221> NAME/KEY: unsure
<222> LOCATION: (537)
<223> OTHER INFORMATION: n = A, C, G or T

<400> SEQUENCE: 18

ttgcaacaca cattgtcttg tcggcaaaat cttccaccaa caacacacag ccatggcagg     60

ctcaaacatt ctttctcact ctccttccct tcccaaaacc tacagccact ccttaaacca    120

aaacgcgtta tcccaaaagc tttttttttct gcccctcaaa ttcaaagcca ccacaaaacc    180

acgtgctctc agagcggttc tctcgcagaa cgctgtcaaa acctcggtgg aggacacaaa    240

gaacgctcat tttcagcact gtttcaccaa atccgaagat gggtatctgt actgtgaggg    300

cctcaaggtg catgacatca tggaatctgt tgagagaaga cctttctatt tgtacagcaa    360

gccccagata actaggaatg ttgaagccta caaggatgca ttggaagggt tgaactccat    420

aattggttat gccattaagg ccaataataa cttgaagatt ttggnacatt tgaggcactt    480

gggttgtggt gctgtgcttg ttagtgggaa tgagctgaag ttgntcttcg agctggnttt    540

gttc                                                                 544


<210> SEQ ID NO 19
<211> LENGTH: 62
<212> TYPE: PRT
<213> ORGANISM: Glycine max
<220> FEATURE:
<221> NAME/KEY: UNSURE
<222> LOCATION: (44)
<223> OTHER INFORMATION: Xaa = ANY AMINO ACID

<400> SEQUENCE: 19

Arg Arg Pro Phe Tyr Leu Tyr Ser Lys Pro Gln Ile Thr Arg Asn Val
1               5                   10                  15

Glu Ala Tyr Lys Asp Ala Leu Glu Gly Leu Asn Ser Ile Ile Gly Tyr
            20                  25                  30

Ala Ile Lys Ala Asn Asn Asn Leu Lys Ile Leu Xaa His Leu Arg His
        35                  40                  45

Leu Gly Cys Gly Ala Val Leu Val Ser Gly Asn Glu Leu Lys
    50                  55                  60


<210> SEQ ID NO 20
<211> LENGTH: 371
<212> TYPE: PRT
<213> ORGANISM: Pseudomonas aeruginosa

<400> SEQUENCE: 20
```

-continued

```
Met Lys Arg Val Gly Leu Ile Gly Trp Arg Gly Met Val Gly Ser Val
1               5                   10                  15

Leu Ile Gln Arg Met Leu Glu Glu Arg Asp Phe Asp Leu Ile Glu Pro
            20                  25                  30

Val Phe Phe Thr Thr Ser Asn Val Gly Ala Gln Ala Pro Glu Val Asp
        35                  40                  45

Lys Asp Ile Ala Pro Leu Lys Asp Ala Tyr Ser Ile Asp Glu Leu Lys
    50                  55                  60

Thr Leu Asp Val Ile Leu Thr Cys Gln Gly Gly Asp Tyr Thr Ser Glu
65                  70                  75                  80

Val Phe Pro Lys Leu Arg Glu Ala Gly Trp Gln Gly Tyr Trp Ile Asp
                85                  90                  95

Ala Ala Ser Ser Leu Arg Met Glu Asp Asp Ala Val Ile Val Leu Asp
            100                 105                 110

Pro Val Asn Arg Lys Val Ile Asp Gln Ala Leu Asp Ala Gly Thr Arg
        115                 120                 125

Asn Tyr Ile Gly Gly Asn Cys Thr Val Ser Leu Met Leu Met Ala Leu
    130                 135                 140

Gly Gly Leu Phe Asp Ala Gly Leu Val Glu Trp Met Ser Ala Met Thr
145                 150                 155                 160

Tyr Gln Ala Ala Ser Gly Ala Gly Ala Gln Asn Met Arg Asp Leu Leu
                165                 170                 175

Lys Gln Met Gly Ala Ala His Ala Ser Val Ala Asp Asp Leu Ala Asn
            180                 185                 190

Pro Ala Ser Ala Ile Leu Asp Ile Asp Arg Lys Val Ala Glu Thr Leu
        195                 200                 205

Arg Ser Glu Ala Phe Pro Thr Glu His Phe Gly Ala Pro Leu Gly Gly
    210                 215                 220

Ser Leu Ile Pro Trp Ile Asp Lys Glu Leu Ser Gln Arg Arg Gln Ser
225                 230                 235                 240

Arg Glu Glu Trp Lys Ala Gln Ala Glu Thr Asn Lys Ile Leu Ala Arg
                245                 250                 255

Phe Lys Asn Pro Ile Pro Val Asp Gly Ile Cys Val Arg Val Gly Ala
            260                 265                 270

Met Arg Cys His Ser Gln Ala Leu Thr Ile Lys Leu Asn Lys Asp Val
        275                 280                 285

Pro Leu Thr Asp Ile Glu Gly Leu Ile Arg Gln His Asn Pro Trp Val
    290                 295                 300

Lys Leu Val Pro Asn His Arg Glu Val Ser Val Arg Glu Leu Thr Pro
305                 310                 315                 320

Ala Ala Val Thr Gly Thr Leu Ser Val Pro Val Gly Arg Leu Arg Lys
                325                 330                 335

Leu Asn Met Val Ser Gln Tyr Leu Gly Ala Phe Thr Val Gly Asp Gln
            340                 345                 350

Leu Leu Trp Gly Ala Ala Glu Pro Leu Arg Arg Met Leu Arg Ile Leu
        355                 360                 365

Leu Glu Arg
    370
```

<210> SEQ ID NO 21
<211> LENGTH: 788
<212> TYPE: DNA
<213> ORGANISM: Zea mays

<400> SEQUENCE: 21

-continued

```
cgacaacatc gcccccgcca tcctcggcgg cttcgtcctc gtccgcagct acgacccctt     60

tcacctcgtc ccgctttcct tcccgccagc gctccgcctc cacttcgtcc tggtcacccc    120

cgacttcgag gcgcccacga gcaagatgcg cgccgcgctg cccaggcagg tcgacgtcca    180

gcagcacgtg cgcaactcca gccaggcagc ggcgctcgtg gcggcggtgc tgcaggggga    240

cgcgggcctc atcggctccg cgatgtcgtc cgacggcatc gtggagccca ccagggcacc    300

cctcatacct ggcatggcgg ccgtaaaggc ggcggccctg caagctggag cgctgggctg    360

cacaattagc ggcgcgggcc ccacagtggt ggccgtcatc caaggggagg aaaggggga     420

ggaggttgcc cgcaagatgg tggacgcgtt ctggagcgca ggcaagctca aggcgacagc    480

aaccgtcgcg cagctcgata cccttggtgc cagggtcatc gccacgtcat ccttgaacta    540

gcaaaagatt cggaaagtgg tactgcaatt gtatcaccaa acaaggaaga atgaagggga    600

accccatgga tttgtatgtt ttctcttctt tcttgcatct ttaggtggtt aattggcttt    660

ggaataaatg agatggagga catcgctaga acaattctgt tccgtgggct gtaatttcaa    720

tttgggctgg tttctttatc atgccatgga taattatgaa taaatttgag gtagtttgtt    780

aaaaaaaa                                                             788
```

<210> SEQ ID NO 22
<211> LENGTH: 179
<212> TYPE: PRT
<213> ORGANISM: Zea mays

<400> SEQUENCE: 22

```
Asp Asn Ile Ala Pro Ala Ile Leu Gly Gly Phe Val Leu Val Arg Ser
1               5                   10                  15

Tyr Asp Pro Phe His Leu Val Pro Leu Ser Phe Pro Pro Ala Leu Arg
            20                  25                  30

Leu His Phe Val Leu Val Thr Pro Asp Phe Glu Ala Pro Thr Ser Lys
        35                  40                  45

Met Arg Ala Ala Leu Pro Arg Gln Val Asp Val Gln Gln His Val Arg
    50                  55                  60

Asn Ser Ser Gln Ala Ala Ala Leu Val Ala Ala Val Leu Gln Gly Asp
65                  70                  75                  80

Ala Gly Leu Ile Gly Ser Ala Met Ser Ser Asp Gly Ile Val Glu Pro
                85                  90                  95

Thr Arg Ala Pro Leu Ile Pro Gly Met Ala Ala Val Lys Ala Ala Ala
            100                 105                 110

Leu Gln Ala Gly Ala Leu Gly Cys Thr Ile Ser Gly Ala Gly Pro Thr
        115                 120                 125

Val Val Ala Val Ile Gln Gly Glu Glu Arg Gly Glu Glu Val Ala Arg
    130                 135                 140

Lys Met Val Asp Ala Phe Trp Ser Ala Gly Lys Leu Lys Ala Thr Ala
145                 150                 155                 160

Thr Val Ala Gln Leu Asp Thr Leu Gly Ala Arg Val Ile Ala Thr Ser
                165                 170                 175

Ser Leu Asn
```

<210> SEQ ID NO 23
<211> LENGTH: 601
<212> TYPE: DNA
<213> ORGANISM: Oryza sativa
<220> FEATURE:
<221> NAME/KEY: unsure

```
<222> LOCATION: (433)
<223> OTHER INFORMATION: n = A, C, G or T
<220> FEATURE:
<221> NAME/KEY: unsure
<222> LOCATION: (600)
<223> OTHER INFORMATION: n = A, C, G or T

<400> SEQUENCE: 23

gtcgccgcca tcgctgccct tcgcgccctc gatgtcaagt cccacgccgt ctccatccac     60

ctcaccaagg gcctccccct cggctccggc ctcggctcct ccgccgcctc cgccgccgcc    120

gctgccaagg ccgttgacgc cctcttcggc tccctcctac accaagatga cctcgtcctc    180

gcgggcctcg agtccgagaa agccgtcagt ggcttccacg ccgacaacat cgccccggcc    240

atcctcggcg gcttcgtcct cgtccgcagc tacgacccct tccacctcat cccgctctcc    300

tccccacctg ccctccgcct ccacttcgtc ctcgtcacgc ccgacttcga ggcgcccacc    360

aagcaagatg cgtgccgcgc tgcccaaaca ggtggccgtc caccaagcac gtccgcaact    420

ccagccaagc ggncgcgctt gtcgccgctg tgctgcaagg ggacgccacc ctcatcggct    480

ccgcaatgtc ctccgacggc atcgtggagc caacaaggcg ccgctgattc tggatggctg    540

cggtcaaagg cgccggcttg gaactggggg aattggctgc acatcagtgg agaaggcaan    600

t                                                                    601


<210> SEQ ID NO 24
<211> LENGTH: 82
<212> TYPE: PRT
<213> ORGANISM: Oryza sativa
<220> FEATURE:
<221> NAME/KEY: UNSURE
<222> LOCATION: (56) (57)
<223> OTHER INFORMATION: Xaa = ANY AMINO ACID

<400> SEQUENCE: 24

Val Ser Ile His Leu Thr Lys Gly Leu Pro Leu Gly Ser Gly Leu Gly
1               5                   10                  15

Ser Ser Ala Ala Ser Ala Ala Ala Ala Ala Lys Ala Val Asp Ala Leu
            20                  25                  30

Phe Gly Ser Leu Leu His Gln Asp Asp Leu Val Leu Ala Gly Leu Glu
        35                  40                  45

Ser Glu Lys Ala Val Ser Gly Xaa Xaa His Ala Asp Asn Ile Ala Pro
    50                  55                  60

Ala Ile Leu Gly Gly Phe Val Leu Val Arg Ser Tyr Asp Pro Phe His
65                  70                  75                  80

Leu Ile


<210> SEQ ID NO 25
<211> LENGTH: 1543
<212> TYPE: DNA
<213> ORGANISM: Glycine max

<400> SEQUENCE: 25

gaagagagac aaaccagcaa gagtggagat ggcgacgtcg acgtgcttcc tgtgtccgtc     60

tacggcgagt ttgaaaggca gggccagatt cagaatcaga atcagatgca gcagcagcgt    120

gtcggtcaat attcgaaggg agcccgaacc tgtaacgacg ctggtgaaag cgtttgctcc    180

cgccacggtg gcgaatctag gtccaggctt cgacttccta ggctgcgccg tggacggact    240

cggagacatt gtgtcggtga aggttgaccc acaggttcac cctggcgaga tatgcatatc    300

cgacatcagc ggccacgccc caaacaagct cagcaaaaac cctctctgga actgcgccgg    360
```

```
catcgccgcc attgaagtca tgaaaatgct ctccattcga tccgtcggcc tctccctctc    420
cctggagaag ggcctgcctt tgggaagcgg tctgggatcc agcgccgcca gcgccgccgc    480
ggccgccgtg gcggtgaacg agctgtttgg gaagaaatta agcgtggagg agctggttct    540
ggcatcactg aaatcggaag agaaggtgtc ggggtatcac gcggacaacg tggcgccatc    600
gataatgggg ggttttgtgc tgatcgggag ctactcgccg ctggagttga tgccgttgaa    660
gtttccggca gagaaggagc tgtatttcgt gctggtgacg cctgagttcg aggccccgac    720
gaagaagatg cgggcagcgc tgcctacgga gatcgggatg ccgcaccacg tgtggaactg    780
cagccaggca ggtgctctgg tggcgtcggt gctgcagggc gacgtggttg ggttggggaa    840
ggcattgtcc tctgacaaga tcgttgagcc aaggcgtgcc cccttgattc ctggcatgga    900
ggctgtcaag agggctgcca ttcaggccgg tgcttttggc tgtaccatca gcggcgccgg    960
ccctaccgcc gtcgccgtca ttgacgacga gcaaactgga cacctcattg ccaaacacat   1020
gattgacgct tttctccatg ttggcaattt gaaggcttct gcaaatgtca agcagcttga   1080
tcgccttggt gctagacgca ttccaaattg aaccttctct tctctatctc tatgagaggc   1140
ttgtagattt caagaaccgg atttcttcca acttgctcgt aacactctaa gtgctgaccg   1200
gtcacatgta tttgaaattt gatctgatca atgaagcagc attctagtgt ggaggtctga   1260
ataacaagag aaacattaaa cccaagctgg gagctctgtt tgggtggtgg aaatttaaat   1320
agatgaataa ttatgaaaga cctagatcag gtcagtgtta tggtgaactc tgaagcatgt   1380
tttagatttt ctttgctttg tttttatcat atttttatct tgctacttga gttgacaaag   1440
ctcaaaaaga agtcattttt agtattttct tgtttcatta tgctagttaa tcttagcttt   1500
tgaatagcat gtattgttcc ttaaaaaaaa aaaaaaaaaa aaa                      1543

<210> SEQ ID NO 26
<211> LENGTH: 483
<212> TYPE: PRT
<213> ORGANISM: Glycine max

<400> SEQUENCE: 26

Met Ala Thr Ser Thr Cys Phe Leu Cys Pro Ser Thr Ala Ser Leu Lys
1               5                   10                  15

Gly Arg Ala Arg Phe Arg Ile Arg Ile Arg Cys Ser Ser Ser Val Ser
            20                  25                  30

Val Asn Ile Arg Arg Glu Pro Glu Pro Val Thr Thr Leu Val Lys Ala
        35                  40                  45

Phe Ala Pro Ala Thr Val Ala Asn Leu Gly Pro Gly Phe Asp Phe Leu
    50                  55                  60

Gly Cys Ala Val Asp Gly Leu Gly Asp Ile Val Ser Val Lys Val Asp
65                  70                  75                  80

Pro Gln Val His Pro Gly Glu Ile Cys Ile Ser Asp Ile Ser Gly His
                85                  90                  95

Ala Pro Asn Lys Leu Ser Lys Asn Pro Leu Trp Asn Cys Ala Gly Ile
            100                 105                 110

Ala Ala Ile Glu Val Met Lys Met Leu Ser Ile Arg Ser Val Gly Leu
        115                 120                 125

Ser Leu Ser Leu Glu Lys Gly Leu Pro Leu Gly Ser Gly Leu Gly Ser
    130                 135                 140

Ser Ala Ala Ser Ala Ala Ala Ala Ala Val Ala Val Asn Glu Leu Phe
145                 150                 155                 160
```

-continued

```
Gly Lys Lys Leu Ser Val Glu Glu Leu Val Leu Ala Ser Leu Lys Ser
                165                 170                 175

Glu Glu Lys Val Ser Gly Tyr His Ala Asp Asn Val Ala Pro Ser Ile
            180                 185                 190

Met Gly Gly Phe Val Leu Ile Gly Ser Tyr Ser Pro Leu Glu Leu Met
        195                 200                 205

Pro Leu Lys Phe Pro Ala Glu Lys Glu Leu Tyr Phe Val Leu Val Thr
    210                 215                 220

Pro Glu Phe Glu Ala Pro Thr Lys Lys Met Arg Ala Ala Leu Pro Thr
225                 230                 235                 240

Glu Ile Gly Met Pro His His Val Trp Asn Cys Ser Gln Ala Gly Ala
                245                 250                 255

Leu Val Ala Ser Val Leu Gln Gly Asp Val Val Gly Leu Gly Lys Ala
            260                 265                 270

Leu Ser Ser Asp Lys Ile Val Glu Pro Arg Arg Ala Pro Leu Ile Pro
        275                 280                 285

Gly Met Glu Ala Val Lys Arg Ala Ala Ile Gln Ala Gly Ala Phe Gly
    290                 295                 300

Cys Thr Ile Ser Gly Ala Gly Pro Thr Ala Val Ala Val Ile Asp Asp
305                 310                 315                 320

Glu Gln Thr Gly His Leu Ile Ala Lys His Met Ile Asp Ala Phe Leu
                325                 330                 335

His Val Gly Asn Leu Lys Ala Ser Ala Asn Val Lys Gln Leu Asp Arg
            340                 345                 350

Leu Gly Ala Arg Arg Ile Pro Asn Thr Phe Ser Ser Leu Ser Leu Glu
        355                 360                 365

Ala Cys Arg Phe Gln Glu Pro Asp Phe Phe Gln Leu Ala Arg Asn Thr
    370                 375                 380

Leu Ser Ala Asp Arg Ser His Val Phe Glu Ile Ser Asp Gln Ser Ser
385                 390                 395                 400

Ile Leu Val Trp Arg Ser Glu Gln Glu Lys His Thr Gln Ala Gly Ser
                405                 410                 415

Ser Val Trp Val Val Glu Ile Ile Asp Glu Leu Lys Thr Ile Arg Ser
            420                 425                 430

Val Leu Trp Thr Leu Lys His Val Leu Asp Phe Leu Cys Phe Val Phe
        435                 440                 445

Ile Ile Phe Leu Ser Cys Tyr Leu Ser Gln Ser Ser Lys Arg Ser His
    450                 455                 460

Phe Tyr Phe Leu Val Ser Leu Cys Leu Ile Leu Ala Phe Glu His Val
465                 470                 475                 480

Leu Phe Leu
```

<210> SEQ ID NO 27
<211> LENGTH: 438
<212> TYPE: DNA
<213> ORGANISM: Triticum aestivum
<220> FEATURE:
<221> NAME/KEY: unsure
<222> LOCATION: (271)
<223> OTHER INFORMATION: n = A, C, G or T
<220> FEATURE:
<221> NAME/KEY: unsure
<222> LOCATION: (421)
<223> OTHER INFORMATION: n = A, C, G or T
<220> FEATURE:
<221> NAME/KEY: unsure
<222> LOCATION: (425)
<223> OTHER INFORMATION: n = A, C, G or T

<400> SEQUENCE: 27

```
ctcgagtcgg agaaggccgt cagcggcttc cacgccgaca acatcgcccc cgccatcctc      60

ggcggcttcg tcctcgtccg cagctacgac ccctttcacc tcgtcccgct ttccttcccg     120

ccagcgctcc gcctccactt cgtcctggtc acccccgact tcgaggcgcc cacgagcaag     180

atgcgcgccg cgctgcccag gcaggtcgac gtccagcagc acgtgcgcaa ctccagccag     240

gcagcggcgc tccgtggcgg cggtgctgca nggggacgcc gggctcatcg gtccgcgatt     300

tctccgacgg gcatcgtgga cccaccaagg aaccctcata cctggcatgg cggccgtaaa     360

ggcggcggcc tgcaactgga cgctgggtgc acattaacgg gcgggcccac atggtggctc     420

ncagngaaga gaggggag                                                   438
```

<210> SEQ ID NO 28
<211> LENGTH: 84
<212> TYPE: PRT
<213> ORGANISM: Triticum aestivum

<400> SEQUENCE: 28

```
Leu Glu Ser Glu Lys Ala Val Ser Gly Phe His Ala Asp Asn Ile Ala
1               5                   10                  15

Pro Ala Ile Leu Gly Gly Phe Val Leu Val Arg Ser Tyr Asp Pro Phe
            20                  25                  30

His Leu Val Pro Leu Ser Phe Pro Pro Ala Leu Arg Leu His Phe Val
        35                  40                  45

Leu Val Thr Pro Asp Phe Glu Ala Pro Thr Ser Lys Met Arg Ala Ala
    50                  55                  60

Leu Pro Arg Gln Val Asp Val Gln Gln His Val Arg Asn Ser Ser Gln
65                  70                  75                  80

Ala Ala Ala Leu
```

<210> SEQ ID NO 29
<211> LENGTH: 300
<212> TYPE: PRT
<213> ORGANISM: Methanococcus jannashii

<400> SEQUENCE: 29

```
Met Arg Glu Ile Met Lys Val Arg Val Lys Ala Pro Cys Thr Ser Ala
1               5                   10                  15

Asn Leu Gly Val Gly Phe Asp Val Phe Gly Leu Cys Leu Lys Glu Pro
            20                  25                  30

Tyr Asp Val Ile Glu Val Glu Ala Ile Asp Asp Lys Glu Ile Ile Ile
        35                  40                  45

Glu Val Asp Asp Lys Asn Ile Pro Thr Asp Pro Asp Lys Asn Val Ala
    50                  55                  60

Gly Ile Val Ala Lys Lys Met Ile Asp Asp Phe Asn Ile Gly Lys Gly
65                  70                  75                  80

Val Lys Ile Thr Ile Lys Lys Gly Val Lys Ala Gly Ser Gly Leu Gly
                85                  90                  95

Ser Ser Ala Ala Ser Ser Ala Gly Thr Ala Tyr Ala Ile Asn Glu Leu
            100                 105                 110

Phe Lys Leu Asn Leu Asp Lys Leu Lys Leu Val Asp Tyr Ala Ser Tyr
        115                 120                 125

Gly Glu Leu Ala Ser Ser Gly Ala Lys His Ala Asp Asn Val Ala Pro
    130                 135                 140
```

-continued

```
Ala Ile Phe Gly Gly Phe Thr Met Val Thr Asn Tyr Glu Pro Leu Glu
145                 150                 155                 160

Val Leu His Ile Pro Ile Asp Phe Lys Leu Asp Ile Leu Ile Ala Ile
                165                 170                 175

Pro Asn Ile Ser Ile Asn Thr Lys Glu Ala Arg Glu Ile Leu Pro Lys
            180                 185                 190

Ala Val Gly Leu Lys Asp Leu Val Asn Asn Val Gly Lys Ala Cys Gly
        195                 200                 205

Met Val Tyr Ala Leu Tyr Asn Lys Asp Lys Ser Leu Phe Gly Arg Tyr
    210                 215                 220

Met Met Ser Asp Lys Val Ile Glu Pro Val Arg Gly Lys Leu Ile Pro
225                 230                 235                 240

Asn Tyr Phe Lys Ile Lys Glu Glu Val Lys Asp Lys Val Tyr Gly Ile
                245                 250                 255

Thr Ile Ser Gly Ser Gly Pro Ser Ile Ile Ala Phe Pro Lys Glu Glu
            260                 265                 270

Phe Ile Asp Glu Val Glu Asn Ile Leu Arg Asp Tyr Tyr Glu Asn Thr
        275                 280                 285

Ile Arg Thr Glu Val Gly Lys Gly Val Glu Val Val
    290                 295                 300
```

<210> SEQ ID NO 30
<211> LENGTH: 1362
<212> TYPE: DNA
<213> ORGANISM: Glycine max

<400> SEQUENCE: 30

```
actttgtagt tcgtagatag ccgatgtgct tgtcttagtg tgtcagtcat tcctgttcct      60

caagtcaagc tttgtagtga gcagatataa tggctgttga aaggtccgga attgccaaag     120

atgttacgga attgattggt aaaaccccat tagtatatct aaataaactt gcggatggtt     180

gtgttgcccg ggttgctgct aaactggagt tgatggagcc atgctctagt gtgaaggaca     240

ggattgggta tagtatgatt gctgatgcag aagagaaggg acttatcaca cctggaaaga     300

gtgtcctcat tgagccaaca agtggtaata ctggcattgg attagccttc atggcagcag     360

ccaggggtta caagctcata attacaatgc ctgcttctat gagtcttgag agaagaatca     420

ttctattagc ttttggagct gagttggttc tgacagatcc tgctaaggga atgaaaggtg     480

ctgttcagaa ggctgaagag atattggcta agacgcccaa tgcctacata cttcaacaat     540

ttgaaaaccc tgccaatccc aaggttcatt atgaaaccac tggtccagag atatggaaag     600

gctccgatgg gaaaattgat gcatttgttt ctgggatagg cactggtggt acaataacag     660

gtgctggaaa atatcttaaa gagcagaatc cgaatataaa gctgattggt gtggaaccag     720

ttgaaagtcc agtgctctca ggaggaaagc ctggtccaca caagattcaa gggattggtg     780

ctggttttat ccctggtgtc ttggaagtca atcttcttga tgaagttgtt caaatatcaa     840

gtgatgaagc aatagaaact gcaaagcttc ttgcgcttaa agaaggccta tttgtgggaa     900

tatcttccgg agctgcagct gctgctgctt ttcagattgc aaaaagacca gaaaatgccg     960

ggaagcttat tgttgccgtt tttcccagct tcggggagag gtacctgtcc tccgtgctat    1020

ttgagtcagt gagacgcgaa gctgaaagca tgacttttga gccctgaatt cccgtttaag    1080

gctctcacta ctgaattttc ttgttacttg taccaggctt taactagatt gttagagtac    1140

tactgtttgt gactctgact ctaaaataaa acttgctcca aaagactagt ttttcttgat    1200

gcccctggag cgataatttt gtgcctgcaa cattaaaaag tattcaaagt tgcttataag    1260
```

-continued

```
taacatgttt catcttttgt tgttgttgag acgaacacgg atgaggtcat aatactatgt   1320

ttctgatttc ctttggtagg gaaaaaaaaa aaaaaaaaaa aa                      1362


<210> SEQ ID NO 31
<211> LENGTH: 325
<212> TYPE: PRT
<213> ORGANISM: Glycine max

<400> SEQUENCE: 31

Met Ala Val Glu Arg Ser Gly Ile Ala Lys Asp Val Thr Glu Leu Ile
1               5                   10                  15

Gly Lys Thr Pro Leu Val Tyr Leu Asn Lys Leu Ala Asp Gly Cys Val
            20                  25                  30

Ala Arg Val Ala Ala Lys Leu Glu Leu Met Glu Pro Cys Ser Ser Val
        35                  40                  45

Lys Asp Arg Ile Gly Tyr Ser Met Ile Ala Asp Ala Glu Glu Lys Gly
    50                  55                  60

Leu Ile Thr Pro Gly Lys Ser Val Leu Ile Glu Pro Thr Ser Gly Asn
65                  70                  75                  80

Thr Gly Ile Gly Leu Ala Phe Met Ala Ala Arg Gly Tyr Lys Leu
                85                  90                  95

Ile Ile Thr Met Pro Ala Ser Met Ser Leu Glu Arg Arg Ile Ile Leu
            100                 105                 110

Leu Ala Phe Gly Ala Glu Leu Val Leu Thr Asp Pro Ala Lys Gly Met
        115                 120                 125

Lys Gly Ala Val Gln Lys Ala Glu Glu Ile Leu Ala Lys Thr Pro Asn
    130                 135                 140

Ala Tyr Ile Leu Gln Gln Phe Glu Asn Pro Ala Asn Pro Lys Val His
145                 150                 155                 160

Tyr Glu Thr Thr Gly Pro Glu Ile Trp Lys Gly Ser Asp Gly Lys Ile
                165                 170                 175

Asp Ala Phe Val Ser Gly Ile Gly Thr Gly Gly Thr Ile Thr Gly Ala
            180                 185                 190

Gly Lys Tyr Leu Lys Glu Gln Asn Pro Asn Ile Lys Leu Ile Gly Val
        195                 200                 205

Glu Pro Val Glu Ser Pro Val Leu Ser Gly Gly Lys Pro Gly Pro His
    210                 215                 220

Lys Ile Gln Gly Ile Gly Ala Gly Phe Ile Pro Gly Val Leu Glu Val
225                 230                 235                 240

Asn Leu Leu Asp Glu Val Val Gln Ile Ser Ser Asp Glu Ala Ile Glu
                245                 250                 255

Thr Ala Lys Leu Leu Ala Leu Lys Glu Gly Leu Phe Val Gly Ile Ser
            260                 265                 270

Ser Gly Ala Ala Ala Ala Ala Ala Phe Gln Ile Ala Lys Arg Pro Glu
        275                 280                 285

Asn Ala Gly Lys Leu Ile Val Ala Val Phe Pro Ser Phe Gly Glu Arg
    290                 295                 300

Tyr Leu Ser Ser Val Leu Phe Glu Ser Val Arg Arg Glu Ala Glu Ser
305                 310                 315                 320

Met Thr Phe Glu Pro
                325


<210> SEQ ID NO 32
<211> LENGTH: 325
```

<212> TYPE: PRT
<213> ORGANISM: Citrullus lanatus

<400> SEQUENCE: 32

```
Met Ala Asp Ala Lys Ser Thr Ile Ala Lys Asp Val Thr Glu Leu Ile
1               5                   10                  15

Gly Asn Thr Pro Leu Val Tyr Leu Asn Arg Val Val Asp Gly Cys Val
            20                  25                  30

Ala Arg Val Ala Ala Lys Leu Glu Met Met Glu Pro Cys Ser Ser Val
        35                  40                  45

Lys Asp Arg Ile Gly Tyr Ser Met Ile Ser Asp Ala Glu Asn Lys Gly
    50                  55                  60

Leu Ile Thr Pro Gly Glu Ser Val Leu Ile Glu Pro Thr Ser Gly Asn
65                  70                  75                  80

Thr Gly Ile Gly Leu Ala Phe Ile Ala Ala Ala Lys Gly Tyr Arg Leu
                85                  90                  95

Ile Ile Cys Met Pro Ala Ser Met Ser Leu Glu Arg Arg Thr Ile Leu
            100                 105                 110

Arg Ala Phe Gly Ala Glu Leu Val Leu Thr Asp Pro Ala Arg Gly Met
        115                 120                 125

Lys Gly Ala Val Gln Lys Ala Glu Glu Ile Lys Ala Lys Thr Pro Asn
    130                 135                 140

Ser Tyr Ile Leu Gln Gln Phe Glu Asn Pro Ala Asn Pro Lys Ile His
145                 150                 155                 160

Tyr Glu Thr Thr Gly Pro Glu Ile Trp Arg Gly Ser Gly Gly Lys Ile
                165                 170                 175

Asp Ala Leu Val Ser Gly Ile Gly Thr Gly Gly Thr Val Thr Gly Ala
            180                 185                 190

Gly Lys Tyr Leu Lys Glu Gln Asn Pro Asn Ile Lys Leu Tyr Gly Val
        195                 200                 205

Glu Pro Val Glu Ser Ala Ile Leu Ser Gly Gly Lys Pro Gly Pro His
    210                 215                 220

Lys Ile Gln Gly Ile Gly Ala Gly Phe Ile Pro Gly Val Leu Asp Val
225                 230                 235                 240

Asn Leu Leu Asp Glu Val Ile Gln Val Ser Ser Glu Glu Ser Ile Glu
                245                 250                 255

Thr Ala Lys Leu Leu Ala Leu Lys Glu Gly Leu Leu Val Gly Ile Ser
            260                 265                 270

Ser Gly Ala Ala Ala Ala Ala Ala Ile Arg Ile Ala Lys Arg Pro Glu
        275                 280                 285

Asn Ala Gly Lys Leu Ile Val Ala Val Phe Pro Ser Phe Gly Glu Arg
    290                 295                 300

Tyr Leu Ser Thr Val Leu Phe Glu Ser Val Lys Arg Glu Thr Glu Asn
305                 310                 315                 320

Met Val Phe Glu Pro
                325
```

<210> SEQ ID NO 33
<211> LENGTH: 789
<212> TYPE: DNA
<213> ORGANISM: Zea mays

<400> SEQUENCE: 33

```
atagcgcatt ctcatggtgc tcttgttttg gttgacaaca gcatcatgtc tccagtgctc      60

tcccgtccta tagaactggg agctgatatc gtgatgcact cggctaccaa atttatagcg     120
```

-continued

```
ggacatagtg atcttatggc tggaattctt gcagtgaagg gtgagagttt ggctaaagag    180

gtagggtttc tgcaaaatgc tgaagggtcg ggtctggcac cttttgactg ctggctttgc    240

ttgaggggaa tcaaaaccat ggctctgcgg gtggagaaac aacaggctaa tgcccagaag    300

attgctgaat tcctggcgtc tcacccgagg gtcaagcaag taaactacgc tgggcttcct    360

gaccatcctg ggcgagcttt acactattcc caggcaaagg gagcgggctc tgttctcagt    420

tttctcaccg gctcactggc cctctcaaag cacgtcgtgg agaccaccaa gtacttcagc    480

gtaacagtca gcttcgggag cgtgaagtcc ctcatcagcc tgccgtgctt catgtcccac    540

gcatcaatcc ctgcctcggt ccgcgaggag cgtggcctaa ccgacgacct cgtccggata    600

tcggtcggca tcgaggatgt cgaggacctc atcgccgatc tggaccgcgc gctcagaact    660

ggcccggtgt agacatcgcc gatccttagg tcatgtcaag ctatcttttg atgattcatt    720

ggttgactgc ttgcgtgatg ataataatgg gaatgttgct tggataaaaa aaaaaaaaaa    780

aaaactcga                                                            789
```

<210> SEQ ID NO 34
<211> LENGTH: 223
<212> TYPE: PRT
<213> ORGANISM: Zea mays

<400> SEQUENCE: 34

```
Ile Ala His Ser His Gly Ala Leu Val Leu Val Asp Asn Ser Ile Met
1               5                   10                  15

Ser Pro Val Leu Ser Arg Pro Ile Glu Leu Gly Ala Asp Ile Val Met
            20                  25                  30

His Ser Ala Thr Lys Phe Ile Ala Gly His Ser Asp Leu Met Ala Gly
        35                  40                  45

Ile Leu Ala Val Lys Gly Glu Ser Leu Ala Lys Glu Val Gly Phe Leu
    50                  55                  60

Gln Asn Ala Glu Gly Ser Gly Leu Ala Pro Phe Asp Cys Trp Leu Cys
65                  70                  75                  80

Leu Arg Gly Ile Lys Thr Met Ala Leu Arg Val Glu Lys Gln Gln Ala
                85                  90                  95

Asn Ala Gln Lys Ile Ala Glu Phe Leu Ala Ser His Pro Arg Val Lys
            100                 105                 110

Gln Val Asn Tyr Ala Gly Leu Pro Asp His Pro Gly Arg Ala Leu His
        115                 120                 125

Tyr Ser Gln Ala Lys Gly Ala Gly Ser Val Leu Ser Phe Leu Thr Gly
    130                 135                 140

Ser Leu Ala Leu Ser Lys His Val Val Glu Thr Thr Lys Tyr Phe Ser
145                 150                 155                 160

Val Thr Val Ser Phe Gly Ser Val Lys Ser Leu Ile Ser Leu Pro Cys
                165                 170                 175

Phe Met Ser His Ala Ser Ile Pro Ala Ser Val Arg Glu Glu Arg Gly
            180                 185                 190

Leu Thr Asp Asp Leu Val Arg Ile Ser Val Gly Ile Glu Asp Val Glu
        195                 200                 205

Asp Leu Ile Ala Asp Leu Asp Arg Ala Leu Arg Thr Gly Pro Val
    210                 215                 220
```

<210> SEQ ID NO 35
<211> LENGTH: 547
<212> TYPE: DNA

<213> ORGANISM: Oryza sativa
<220> FEATURE:
<221> NAME/KEY: unsure
<222> LOCATION: (260)
<223> OTHER INFORMATION: n = A, C, G or T
<220> FEATURE:
<221> NAME/KEY: unsure
<222> LOCATION: (306)
<223> OTHER INFORMATION: n = A, C, G or T
<220> FEATURE:
<221> NAME/KEY: unsure
<222> LOCATION: (376)
<223> OTHER INFORMATION: n = A, C, G or T
<220> FEATURE:
<221> NAME/KEY: unsure
<222> LOCATION: (383)
<223> OTHER INFORMATION: n = A, C, G or T
<220> FEATURE:
<221> NAME/KEY: unsure
<222> LOCATION: (404)
<223> OTHER INFORMATION: n = A, C, G or T
<220> FEATURE:
<221> NAME/KEY: unsure
<222> LOCATION: (432)
<223> OTHER INFORMATION: n = A, C, G or T
<220> FEATURE:
<221> NAME/KEY: unsure
<222> LOCATION: (446)
<223> OTHER INFORMATION: n = A, C, G or T
<220> FEATURE:
<221> NAME/KEY: unsure
<222> LOCATION: (455) (456)
<223> OTHER INFORMATION: n = A, C, G or T
<220> FEATURE:
<221> NAME/KEY: unsure
<222> LOCATION: (509)
<223> OTHER INFORMATION: n = A, C, G or T
<220> FEATURE:
<221> NAME/KEY: unsure
<222> LOCATION: (514)
<223> OTHER INFORMATION: n = A, C, G or T
<220> FEATURE:
<221> NAME/KEY: unsure
<222> LOCATION: (522
<223> OTHER INFORMATION: n = A, C, G or T
<220> FEATURE:
<221> NAME/KEY: unsure
<222> LOCATION: (537)
<223> OTHER INFORMATION: n = A, C, G or T

<400> SEQUENCE: 35

```
gccttatggc taagcttgag aaggcggatc aggcattctg cttcaccagt gggatggcag     60

cactagctgc agtaacacac ctccttaagt ctggacaaga aatagttgct ggagaggaca    120

tatatggtgg ctcagaccgt ctgctctcac aagttgcccc gagacatggg attgtagtaa    180

aacgaattga tacaaccaaa attagtgagg taacttctgc aattggggcc ttggactaaa    240

ctaagtatgg ctttgaaaan cccaccatcc ccgtcctaca aattactgga tataaagaaa    300

atagcnagag atagtcatta caatggggct ccttgtttta agtagacaac agcacatgtc    360

tccctgtgct ctcccngtcc tcntaaaact ttgggccaaa tatnggtttg caccccaagc    420

aaccaattta tnctgggcat agcgtnctta tggcnnggat ccttgccggg aaggggtgaa    480

agcacttggc taaagagatg cattcctcna aaanctgaag gntaagtttg gacattngat    540

gccggtt                                                               547
```

<210> SEQ ID NO 36
<211> LENGTH: 75
<212> TYPE: PRT
<213> ORGANISM: Oryza sativa

<400> SEQUENCE: 36

-continued

```
Leu Met Ala Lys Leu Glu Lys Ala Asp Gln Ala Phe Cys Phe Thr Ser
1               5                   10                  15

Gly Met Ala Ala Leu Ala Ala Val Thr His Leu Leu Lys Ser Gly Gln
            20                  25                  30

Glu Ile Val Ala Gly Glu Asp Ile Tyr Gly Gly Ser Asp Arg Leu Leu
        35                  40                  45

Ser Gln Val Ala Pro Arg His Gly Ile Val Val Lys Arg Ile Asp Thr
    50                  55                  60

Thr Lys Ile Ser Glu Val Thr Ser Ala Ile Gly
65                  70                  75


<210> SEQ ID NO 37
<211> LENGTH: 1733
<212> TYPE: DNA
<213> ORGANISM: Glycine max

<400> SEQUENCE: 37

caaagacggc attgaagttg aacaatccat cactaacaca agcgcagaca acaacataac     60

cctgctccaa acacatcaat ttcaataatg ttttcttctg caatttctca gaagcccttc    120

cttcagtccc tcgtcattga tcgttacgct cagagcacaa ctgctgcaac caggtgggag    180

tgcttggggt ttaacaagtc agaaaatttc agtaccaaga gagtgttgcg tgcagagggg    240

ttcaagttga attgcttggt tgaaaataga gagatggaag tggagtcatc atcatcatct    300

ttggtggatg atgctgccat gagcttaagt gaagaggatt taggggagcc tagtatttca    360

acaatggtga tgaatttcga gagtaagttt gatccttttg gagcaattag taccccgctt    420

taccaaacgg ctacttttaa gcagccttct gcaatagaaa atggtcccta tgactatacc    480

agaagtggaa atcctactcg tgatgcttta gaaagtttac tagcaaagct tgataaagca    540

gatagagccc tgtgcttcac cagtggaatg gctgctttga gtgctgttgt tcgtcttgtt    600

ggaactggtg aggaaattgt caccggagat gatgtatatg gtggctcaga taggttgctg    660

tctcaagtag ttccaaggac tggaattgtg gtgaaacggg taaatacatg tgatctagat    720

gaggttgctg ctgccattgg actcaggact aagcttgtgt ggcttgagag tccaaccaat    780

cctcggcttc aaatttctga tattcgaaaa atatcagaga tggctcattc acatggtgct    840

cttgtgttag tggacaatag tataatgtca cctgtgttgt ctcagccatt ggaacttgga    900

gcagatattg tcatgcactc agctacaaaa tttattgctg gacatagtga cattatggct    960

ggtgtgcttg ctgtgaaggg tgaaaagttg ggaaaggaaa tgtatttctt gcaaaatgca   1020

gagggttcag gcttagcacc atttgactgt tggctttgtt tgcgaggaat caagacaatg   1080

gccctgcgaa ttgaaaagca acaggataac gcacagaaga ttgcagagtt ccttgcctcc   1140

catcctcgag tgaaggaagt gaattatgct ggcttgcctg gtcatcctgg tcgtgattta   1200

cactattctc aggcaaaggg tgcaggatct gtgcttagct tcttgactgg ttcattggca   1260

ctttcaaagc atattgttga aactaccaaa tacttcagta taaccgtcag ctttgggagt   1320

gtgaagtccc tcattagcat gccatgcttt atgtcacatg caagcatacc tgctgcagtt   1380

cgcgaggcca gaggtttaac tgaagatctt gtacgaatat ctgtgggaat tgaggatgtg   1440

aatgatctca ttgctgatct tggcaatgca cttagaactg gacctcttta atgtcttctc   1500

caccccccca cccaaaaaga aaaaaattca tccttaagaa gttggattag catgttgagg   1560

atttgggagc attgctatcc tgtctttgga ttcttgagag tggaaacttg aagtgttgct   1620

tatgtgcatg taataaaatc aatatttcct gtaattttgt tgtaacaatt gttatcctta   1680
```

```
ccttgcaata tcatgtcata caagttacta ttgaaaaaaa aaaaaaaaaa aaa         1733


<210> SEQ ID NO 38
<211> LENGTH: 467
<212> TYPE: PRT
<213> ORGANISM: Glycine max

<400> SEQUENCE: 38

Met Phe Ser Ser Ala Ile Ser Gln Lys Pro Phe Leu Gln Ser Leu Val
1               5                   10                  15

Ile Asp Arg Tyr Ala Gln Ser Thr Thr Ala Ala Thr Arg Trp Glu Cys
            20                  25                  30

Leu Gly Phe Asn Lys Ser Glu Asn Phe Ser Thr Lys Arg Val Leu Arg
        35                  40                  45

Ala Glu Gly Phe Lys Leu Asn Cys Leu Val Glu Asn Arg Glu Met Glu
    50                  55                  60

Val Glu Ser Ser Ser Ser Ser Leu Val Asp Asp Ala Ala Met Ser Leu
65                  70                  75                  80

Ser Glu Glu Asp Leu Gly Glu Pro Ser Ile Ser Thr Met Val Met Asn
                85                  90                  95

Phe Glu Ser Lys Phe Asp Pro Phe Gly Ala Ile Ser Thr Pro Leu Tyr
            100                 105                 110

Gln Thr Ala Thr Phe Lys Gln Pro Ser Ala Ile Glu Asn Gly Pro Tyr
        115                 120                 125

Asp Tyr Thr Arg Ser Gly Asn Pro Thr Arg Asp Ala Leu Glu Ser Leu
    130                 135                 140

Leu Ala Lys Leu Asp Lys Ala Asp Arg Ala Leu Cys Phe Thr Ser Gly
145                 150                 155                 160

Met Ala Ala Leu Ser Ala Val Val Arg Leu Val Gly Thr Gly Glu Glu
                165                 170                 175

Ile Val Thr Gly Asp Asp Val Tyr Gly Gly Ser Asp Arg Leu Leu Ser
            180                 185                 190

Gln Val Val Pro Arg Thr Gly Ile Val Val Lys Arg Val Asn Thr Cys
        195                 200                 205

Asp Leu Asp Glu Val Ala Ala Ala Ile Gly Leu Arg Thr Lys Leu Val
    210                 215                 220

Trp Leu Glu Ser Pro Thr Asn Pro Arg Leu Gln Ile Ser Asp Ile Arg
225                 230                 235                 240

Lys Ile Ser Glu Met Ala His Ser His Gly Ala Leu Val Leu Val Asp
                245                 250                 255

Asn Ser Ile Met Ser Pro Val Leu Ser Gln Pro Leu Glu Leu Gly Ala
            260                 265                 270

Asp Ile Val Met His Ser Ala Thr Lys Phe Ile Ala Gly His Ser Asp
        275                 280                 285

Ile Met Ala Gly Val Leu Ala Val Lys Gly Glu Lys Leu Gly Lys Glu
    290                 295                 300

Met Tyr Phe Leu Gln Asn Ala Glu Gly Ser Gly Leu Ala Pro Phe Asp
305                 310                 315                 320

Cys Trp Leu Cys Leu Arg Gly Ile Lys Thr Met Ala Leu Arg Ile Glu
                325                 330                 335

Lys Gln Gln Asp Asn Ala Gln Lys Ile Ala Glu Phe Leu Ala Ser His
            340                 345                 350

Pro Arg Val Lys Glu Val Asn Tyr Ala Gly Leu Pro Gly His Pro Gly
        355                 360                 365
```

```
Arg Asp Leu His Tyr Ser Gln Ala Lys Gly Ala Gly Ser Val Leu Ser
    370                 375                 380

Phe Leu Thr Gly Ser Leu Ala Leu Ser Lys His Ile Val Glu Thr Thr
385                 390                 395                 400

Lys Tyr Phe Ser Ile Thr Val Ser Phe Gly Ser Val Lys Ser Leu Ile
                405                 410                 415

Ser Met Pro Cys Phe Met Ser His Ala Ser Ile Pro Ala Ala Val Arg
            420                 425                 430

Glu Ala Arg Gly Leu Thr Glu Asp Leu Val Arg Ile Ser Val Gly Ile
        435                 440                 445

Glu Asp Val Asn Asp Leu Ile Ala Asp Leu Gly Asn Ala Leu Arg Thr
    450                 455                 460

Gly Pro Leu
465
```

<210> SEQ ID NO 39
<211> LENGTH: 637
<212> TYPE: DNA
<213> ORGANISM: Triticum aestivum
<220> FEATURE:
<221> NAME/KEY: unsure
<222> LOCATION: (400)
<223> OTHER INFORMATION: n = A, C, G or T
<220> FEATURE:
<221> NAME/KEY: unsure
<222> LOCATION: (417)
<223> OTHER INFORMATION: n = A, C, G or T
<220> FEATURE:
<221> NAME/KEY: unsure
<222> LOCATION: (486)
<223> OTHER INFORMATION: n = A, C, G or T
<220> FEATURE:
<221> NAME/KEY: unsure
<222> LOCATION: (492) (493)
<223> OTHER INFORMATION: n = A, C, G or T
<220> FEATURE:
<221> NAME/KEY: unsure
<222> LOCATION: (505)
<223> OTHER INFORMATION: n = A, C, G or T
<220> FEATURE:
<221> NAME/KEY: unsure
<222> LOCATION: (518)
<223> OTHER INFORMATION: n = A, C, G or T
<220> FEATURE:
<221> NAME/KEY: unsure
<222> LOCATION: (524)
<223> OTHER INFORMATION: n = A, C, G or T
<220> FEATURE:
<221> NAME/KEY: unsure
<222> LOCATION: (530)
<223> OTHER INFORMATION: n = A, C, G or T
<220> FEATURE:
<221> NAME/KEY: unsure
<222> LOCATION: (532)
<223> OTHER INFORMATION: n = A, C, G or T
<220> FEATURE:
<221> NAME/KEY: unsure
<222> LOCATION: (557)
<223> OTHER INFORMATION: n = A, C, G or T
<220> FEATURE:
<221> NAME/KEY: unsure
<222> LOCATION: (563)
<223> OTHER INFORMATION: n = A, C, G or T
<220> FEATURE:
<221> NAME/KEY: unsure
<222> LOCATION: (581)
<223> OTHER INFORMATION: n = A, C, G or T
<220> FEATURE:
<221> NAME/KEY: unsure
<222> LOCATION: (591)
<223> OTHER INFORMATION: n = A, C, G or T -continued
<220> FEATURE:
<221> NAME/KEY: unsure
<222> LOCATION: (596)
<223> OTHER INFORMATION: n = A, C, G or T
<220> FEATURE:
<221> NAME/KEY: unsure
<222> LOCATION: (617)
<223> OTHER INFORMATION: n = A, C, G or T

<400> SEQUENCE: 39

```
agcgtggcca cgatactgac cagcttcgag aactcgttcg acaagtatgg ggctctcagc     60

acgccgctgt accagacggc caccttcaag cagccttcag caaccgttaa tggagcttat    120

gattatacta gaagtggcaa ccctactcgt gatgttctcc agagccttat ggctaagctc    180

gagaaggcag accaagcatt ctgcttcact agtgggatgg catcactggg ctgcagtaac    240

acacctcctt caggctggac aagaaatagt tgctggagag gacatatatg gtggtctgat    300

cgtctgctct cacaagttgt cccaagaaat ggaattgtag taaaacgggt cgatacaact    360

aaaattaacg acgtgactgc tgcatcggac ccttgactan actagtttgg ttgaaancca    420

caatcctcgt caacaattac tgtataagaa atctcaggga tactcatcca tggggactgg    480

tttggnggca annttcatgt cccanggcta cctggccnat aaantggggn antatgggag    540

catcagtaca aattatnctg gcnatgtcta ggtggatctc ntaaggggaa nttggnagga    600

ttcttcaaaa cctagtnggt tgacttatgt ggttgtt                             637
```

<210> SEQ ID NO 40
<211> LENGTH: 131
<212> TYPE: PRT
<213> ORGANISM: Triticum aestivum
<220> FEATURE:
<221> NAME/KEY: UNSURE
<222> LOCATION: (77)
<223> OTHER INFORMATION: Xaa = ANY AMINO ACID
<220> FEATURE:
<221> NAME/KEY: UNSURE
<222> LOCATION: (99)
<223> OTHER INFORMATION: Xaa = ANY AMINO ACID

<400> SEQUENCE: 40

```
Ser Val Ala Thr Ile Leu Thr Ser Phe Glu Asn Ser Phe Asp Lys Tyr
1               5                   10                  15

Gly Ala Leu Ser Thr Pro Leu Tyr Gln Thr Ala Thr Phe Lys Gln Pro
            20                  25                  30

Ser Ala Thr Val Asn Gly Ala Tyr Asp Tyr Thr Arg Ser Gly Asn Pro
        35                  40                  45

Thr Arg Asp Val Leu Gln Ser Leu Met Ala Lys Leu Glu Lys Ala Asp
    50                  55                  60

Gln Ala Phe Cys Phe Thr Ser Gly Met Ala Ser Leu Xaa Ala Val Thr
65                  70                  75                  80

His Leu Leu Gln Ala Gly Gln Glu Ile Val Ala Gly Glu Asp Ile Tyr
                85                  90                  95

Gly Gly Xaa Asp Arg Leu Leu Ser Gln Val Val Pro Arg Asn Gly Ile
            100                 105                 110

Val Val Lys Arg Val Asp Thr Thr Lys Ile Asn Asp Val Thr Ala Ala
        115                 120                 125

Ser Asp Pro
    130
```

<210> SEQ ID NO 41
<211> LENGTH: 464

```
<212> TYPE: PRT
<213> ORGANISM: Arabidopsis thaliana

<400> SEQUENCE: 41

Met Thr Ser Ser Leu Ser Leu His Ser Ser Phe Val Pro Ser Phe Ala
1               5                   10                  15

Asp Leu Ser Asp Arg Gly Leu Ile Ser Lys Asn Ser Pro Thr Ser Val
            20                  25                  30

Ser Ile Ser Lys Val Pro Thr Trp Glu Lys Lys Gln Ile Ser Asn Arg
        35                  40                  45

Asn Ser Phe Lys Leu Asn Cys Val Met Glu Lys Ser Val Asp Gly Gln
    50                  55                  60

Thr His Ser Thr Val Asn Asn Thr Thr Asp Ser Leu Asn Thr Met Asn
65                  70                  75                  80

Ile Lys Glu Glu Ala Ser Val Ser Thr Leu Leu Val Asn Leu Asp Asn
                85                  90                  95

Lys Phe Asp Pro Phe Asp Ala Met Ser Thr Pro Leu Tyr Gln Thr Ala
            100                 105                 110

Thr Phe Lys Gln Pro Ser Ala Ile Glu Asn Gly Pro Tyr Asp Tyr Thr
        115                 120                 125

Arg Ser Gly Asn Pro Thr Arg Asp Ala Leu Glu Ser Leu Leu Ala Lys
    130                 135                 140

Leu Asp Lys Ala Asp Arg Ala Phe Cys Phe Thr Ser Gly Met Ala Ala
145                 150                 155                 160

Leu Ser Ala Val Thr His Leu Ile Lys Asn Gly Glu Glu Ile Val Ala
                165                 170                 175

Gly Asp Asp Val Tyr Gly Gly Ser Asp Arg Leu Leu Ser Gln Val Val
            180                 185                 190

Pro Arg Ser Gly Val Val Val Lys Arg Val Asn Thr Thr Lys Leu Asp
        195                 200                 205

Glu Val Ala Ala Ala Ile Gly Pro Gln Thr Lys Leu Val Trp Leu Glu
    210                 215                 220

Ser Pro Thr Asn Pro Arg Gln Gln Ile Ser Asp Ile Arg Lys Ile Ser
225                 230                 235                 240

Glu Met Ala His Ala Gln Gly Ala Leu Val Leu Val Asp Asn Ser Ile
                245                 250                 255

Met Ser Pro Val Leu Ser Arg Pro Leu Glu Leu Gly Ala Asp Ile Val
            260                 265                 270

Met His Ser Ala Thr Lys Phe Ile Ala Gly His Ser Asp Val Met Ala
        275                 280                 285

Gly Val Leu Ala Val Lys Gly Glu Lys Leu Ala Lys Glu Val Tyr Phe
    290                 295                 300

Leu Gln Asn Ser Glu Gly Ser Gly Leu Ala Pro Phe Asp Cys Trp Leu
305                 310                 315                 320

Cys Leu Arg Gly Ile Lys Thr Met Ala Leu Arg Ile Glu Lys Gln Gln
                325                 330                 335

Glu Asn Ala Arg Lys Ile Ala Met Tyr Leu Ser Ser His Pro Arg Val
            340                 345                 350

Lys Lys Val Tyr Tyr Ala Gly Leu Pro Asp His Pro Gly His His Leu
        355                 360                 365

His Phe Ser Gln Ala Lys Gly Ala Gly Ser Val Phe Ser Phe Ile Thr
    370                 375                 380

Gly Ser Val Ala Leu Ser Lys His Leu Val Glu Thr Thr Lys Tyr Phe
385                 390                 395                 400
```

```
Ser Ile Ala Val Ser Phe Gly Ser Val Lys Ser Leu Ile Ser Met Pro
                405                 410                 415

Cys Phe Met Ser His Ala Ser Ile Pro Ala Glu Val Arg Glu Ala Arg
            420                 425                 430

Gly Leu Thr Glu Asp Leu Val Arg Ile Ser Ala Gly Ile Glu Asp Val
        435                 440                 445

Asp Asp Leu Ile Ser Asp Leu Asp Ile Ala Phe Lys Thr Phe Pro Leu
    450                 455                 460


<210> SEQ ID NO 42
<211> LENGTH: 1113
<212> TYPE: DNA
<213> ORGANISM: Zea mays

<400> SEQUENCE: 42

gccgtccagg acctcgcggc ccctggggcg ttcgacggcg tcgacatcgc gctattcagc     60

gccggcggga gcgtcagccg gaagtatggg cccgcggccg tcgccagcgg cgccgtagtt    120

gtcgacaaca gctccgcgtt ccggatggag cccgaggtgc cgctcgtcat ccccgaggtc    180

aaccccgagg ccatggcgaa cgtccgcctc gggcaggggg cgattgtggc aaatccgaat    240

tgctcgacca tcatctgcct catggctgcc acgccgctcc atcgccacgc taaggtgtta    300

aggatggttg tcagcacata ccaagcagca agtggtgcgg gtgctgcggc aatggaagaa    360

ctcaagctgc agactcagga ggtcttggaa gggaaggcgc caacatgcaa cattttcaaa    420

cagcagtatg cttttaatat attctcacac aatgcaccag ttcttgagaa tgggtataac    480

gaggaggaaa tgaaaatggt gaaggagacc aggaaaattt ggaatgacaa ggaggtgaaa    540

gtaactgcga cttgcatacg ggttcctgtg atgcgcgcac atgctgaaag tgtcaatcta    600

cagtttgaaa agccacttga tgaggatact gcaagagaaa ttttgagagc agctcctggt    660

gttaccatta ttgatgaccg agcttccaat cgctttccta cacctctgga ggtatcagac    720

aaagatgacg tagcagtggg taggattcgt caggacttgt ccctggatgg taaccgaggg    780

ttggacatat ttgtgtgtgg tgatcagata cgtaaaggcg ccgcactcaa tgccgttcag    840

attgctgaaa tgctgctgaa gtgaatgtga cctaaccctc ttgtccctcc ctccctgtcc    900

ctaattgctc tgatcaaatg ctggactgta ctctgattag tttgtcctca attttggtcg    960

cctgttctgt attctgccgt gctagtgcaa taattgtgtt atgggcttga gttatctgct   1020

gtacgcataa gtgggctcct aaactgggaa ataatgggcc gtccttattc agcattccgg   1080

tttatatctt gttcaaaaaa aaaaaaaaaa ata                                1113


<210> SEQ ID NO 43
<211> LENGTH: 287
<212> TYPE: PRT
<213> ORGANISM: Zea mays

<400> SEQUENCE: 43

Ala Val Gln Asp Leu Ala Ala Pro Gly Ala Phe Asp Gly Val Asp Ile
  1               5                  10                  15

Ala Leu Phe Ser Ala Gly Gly Ser Val Ser Arg Lys Tyr Gly Pro Ala
             20                  25                  30

Ala Val Ala Ser Gly Ala Val Val Val Asp Asn Ser Ser Ala Phe Arg
         35                  40                  45

Met Glu Pro Glu Val Pro Leu Val Ile Pro Glu Val Asn Pro Glu Ala
     50                  55                  60
```

-continued

```
Met Ala Asn Val Arg Leu Gly Gln Gly Ala Ile Val Ala Asn Pro Asn
 65                  70                  75                  80

Cys Ser Thr Ile Ile Cys Leu Met Ala Ala Thr Pro Leu His Arg His
                 85                  90                  95

Ala Lys Val Leu Arg Met Val Val Ser Thr Tyr Gln Ala Ala Ser Gly
            100                 105                 110

Ala Gly Ala Ala Ala Met Glu Glu Leu Lys Leu Gln Thr Gln Glu Val
        115                 120                 125

Leu Glu Gly Lys Ala Pro Thr Cys Asn Ile Phe Lys Gln Gln Tyr Ala
    130                 135                 140

Phe Asn Ile Phe Ser His Asn Ala Pro Val Leu Glu Asn Gly Tyr Asn
145                 150                 155                 160

Glu Glu Glu Met Lys Met Val Lys Glu Thr Arg Lys Ile Trp Asn Asp
                165                 170                 175

Lys Glu Val Lys Val Thr Ala Thr Cys Ile Arg Val Pro Val Met Arg
            180                 185                 190

Ala His Ala Glu Ser Val Asn Leu Gln Phe Glu Lys Pro Leu Asp Glu
        195                 200                 205

Asp Thr Ala Arg Glu Ile Leu Arg Ala Ala Pro Gly Val Thr Ile Ile
    210                 215                 220

Asp Asp Arg Ala Ser Asn Arg Phe Pro Thr Pro Leu Glu Val Ser Asp
225                 230                 235                 240

Lys Asp Asp Val Ala Val Gly Arg Ile Arg Gln Asp Leu Ser Leu Asp
                245                 250                 255

Gly Asn Arg Gly Leu Asp Ile Phe Val Cys Gly Asp Gln Ile Arg Lys
            260                 265                 270

Gly Ala Ala Leu Asn Ala Val Gln Ile Ala Glu Met Leu Leu Lys
        275                 280                 285


<210> SEQ ID NO 44
<211> LENGTH: 1402
<212> TYPE: DNA
<213> ORGANISM: Oryza sativa

<400> SEQUENCE: 44

gcccaactcc caaaacccta gaaccgcgcc gccacaatgc aggccgccgc cgccgccgtc     60

caccgcccgc acctcctcgg cgcctacccc ggcggtggcc gcgcgcgccg cccgtcgtcc    120

accgtgcgga tggcgcttcg ggaggacggg ccgtcggtgg cgatcgtggg cgcgacgggc    180

gccgtcggcc aggagttcct ccgcgtcatc tcctcccggg gcttccccta ccggagcctc    240

cgcctcctcg ccagcgagcg ctccgcgggg aagcgcctcc cgttcgaggg ccaggagtac    300

accgtccagg acctcgccgc gccgggcgcg ttcgacgggg tggacatcgc gctcttcagc    360

gccggcggcg gggtcagccg cgcccacgct cccgcggccg tcgccagcgg cgccgtcgtc    420

gtggacaaca gctccgcctt ccggatggac cccgaggtgc cgctcgtcat ccccgaggtc    480

aatcccgagg ccatggcgca cgtccggctg ggaaaggggg ctattgtggc caacccgaac    540

tgttccacca tcatctgcct catggctgcc acacctctgc accgccacgc caaggtggta    600

aggatggttg tcagcactta ccaagcagca agtggtgctg gggctgcggc catggaagaa    660

ctcaaacttc aaactcaaga ggtcttggcg gggaaagcac caacatgcaa cattttcagt    720

cagcagtatg cttttaatat attttcacat aatgcaccaa ttgttgaaaa tgggtacaat    780

gaggaggaga tgaagatggt gaaggagacc agaaaaatct ggaatgataa agatgtgaag    840

gtaactgcaa cctgcatacg agttcctgtg atgcgtgcac atgctgaaag tgtgaatcta    900
```

-continued

```
cagtttgaaa agccacttga tgaggatact gcaagggaaa tcttgagggc agctgaaggt    960

gttaccatta ttgatgaccg tgcttccaat cgcttcccca cacctcttga ggtatcggat   1020

aaagatgatg tagcagtggg tagaattcgt caggatttgt cgcaagatga taacaaaggg   1080

ctggacatat ttgtttgtgg agatcaaata cgtaaaggtg ctgcactcaa tgctgtgcag   1140

attgctgaaa tgctactcaa gtgattttct tttctgtacc tttctctcct tgcccctctt   1200

tgctctagtc attgtttgac ggatgtactc tggttagtat gagatcaatt ttgatcatct   1260

tttgtaatct atattcctag tgaaataaat gtaaaacggt tttgctctat cttctgcaca   1320

agtgtagaag aaatctgaaa ttgggaaatt ggagtgtggc ccttgttcaa aaaaaaaaaa   1380

aaaaaaaaaa aaaaaaaaaa aa                                            1402


<210> SEQ ID NO 45
<211> LENGTH: 375
<212> TYPE: PRT
<213> ORGANISM: Oryza sativa

<400> SEQUENCE: 45

Met Gln Ala Ala Ala Ala Ala Val His Arg Pro His Leu Leu Gly Ala
  1               5                  10                  15

Tyr Pro Gly Gly Gly Arg Ala Arg Arg Pro Ser Ser Thr Val Arg Met
             20                  25                  30

Ala Leu Arg Glu Asp Gly Pro Ser Val Ala Ile Val Gly Ala Thr Gly
         35                  40                  45

Ala Val Gly Gln Glu Phe Leu Arg Val Ile Ser Ser Arg Gly Phe Pro
     50                  55                  60

Tyr Arg Ser Leu Arg Leu Leu Ala Ser Glu Arg Ser Ala Gly Lys Arg
 65                  70                  75                  80

Leu Pro Phe Glu Gly Gln Glu Tyr Thr Val Gln Asp Leu Ala Ala Pro
                 85                  90                  95

Gly Ala Phe Asp Gly Val Asp Ile Ala Leu Phe Ser Ala Gly Gly Gly
            100                 105                 110

Val Ser Arg Ala His Ala Pro Ala Ala Val Ala Ser Gly Ala Val Val
        115                 120                 125

Val Asp Asn Ser Ser Ala Phe Arg Met Asp Pro Glu Val Pro Leu Val
    130                 135                 140

Ile Pro Glu Val Asn Pro Glu Ala Met Ala His Val Arg Leu Gly Lys
145                 150                 155                 160

Gly Ala Ile Val Ala Asn Pro Asn Cys Ser Thr Ile Ile Cys Leu Met
                165                 170                 175

Ala Ala Thr Pro Leu His Arg His Ala Lys Val Val Arg Met Val Val
            180                 185                 190

Ser Thr Tyr Gln Ala Ala Ser Gly Ala Gly Ala Ala Ala Met Glu Glu
        195                 200                 205

Leu Lys Leu Gln Thr Gln Glu Val Leu Ala Gly Lys Ala Pro Thr Cys
    210                 215                 220

Asn Ile Phe Ser Gln Gln Tyr Ala Phe Asn Ile Phe Ser His Asn Ala
225                 230                 235                 240

Pro Ile Val Glu Asn Gly Tyr Asn Glu Glu Glu Met Lys Met Val Lys
                245                 250                 255

Glu Thr Arg Lys Ile Trp Asn Asp Lys Asp Val Lys Val Thr Ala Thr
            260                 265                 270

Cys Ile Arg Val Pro Val Met Arg Ala His Ala Glu Ser Val Asn Leu
```

-continued

```
        275                 280                 285

Gln Phe Glu Lys Pro Leu Asp Glu Asp Thr Ala Arg Glu Ile Leu Arg
    290                 295                 300

Ala Ala Glu Gly Val Thr Ile Ile Asp Asp Arg Ala Ser Asn Arg Phe
305                 310                 315                 320

Pro Thr Pro Leu Glu Val Ser Asp Lys Asp Asp Val Ala Val Gly Arg
                325                 330                 335

Ile Arg Gln Asp Leu Ser Gln Asp Asp Asn Lys Gly Leu Asp Ile Phe
            340                 345                 350

Val Cys Gly Asp Gln Ile Arg Lys Gly Ala Ala Leu Asn Ala Val Gln
        355                 360                 365

Ile Ala Glu Met Leu Leu Lys
    370                 375


<210> SEQ ID NO 46
<211> LENGTH: 1391
<212> TYPE: DNA
<213> ORGANISM: Glycine max

<400> SEQUENCE: 46

gcacgagctt cactctctgt tttgcgccac aaccacctct tctcgggccc cctcccggcc     60

cgccccaagc ccacctcctc ctcctcctcc aggatccgaa tgtccctccg cgagaacggc    120

ccctccatcg ccgtcgtggg cgtcaccggc gccgtcggcc aggagttcct ctccgtcctc    180

tccgaccgcg acttccccta ccgctccatt catatgctgg cttccaagcg ctccgctggc    240

cgccgcatca ccttcgagga cagggactac gtcgtccagg agctcacgcc ggagagcttc    300

gacggtgtcg acatcgcgct cttcagcgcc ggcggctcca tcagcaagca cttcggcccc    360

atcgccgtca atcgtggaac ggtcgtggtc gacaacagct ccgcgtttcg gatgaacgag    420

aaggtgcctt tggtaattcc cgaagtgaac cccgaagcaa tgcaaaacat caaagccgga    480

acgggaaagg gcgcactcat tgctaaccct aattgctcca ccattatatg cttgatggct    540

gctacccctc ttcatcgacg tgccaaggtg ttacgtatgg ttgttagtac ctatcaggct    600

gcgagtggtg ctggtgctgc tgcaatggaa gagcttgagc tgcaaactcg tgaggtgttg    660

gaaggaaaac cacccacttg taaaatattt aaccgacagt atgcttttaa tctattctca    720

cataatgcgt ctgttctttc aaatggatat aatgaagaag aaatgaaaat ggtcaaggag    780

accaggaaaa tctggaatga caaggatgtt aaagtaactg ccacatgcat acgagttccc    840

atcatgcgag ctcatgctga gagtgtgaat cttcaatttg aaagacccct tgatgaggac    900

actgcaagag atattctgaa aaatgctcca ggtgtagtgg ttattgatga tcgtgaatcc    960

aatcattttc ctactccact ggaagtgtca aacaaggatg atgttgctgt tggtaggatt   1020

cggcaggacc tgtctcagga tgggaatcaa gggttggaca tctttgtatg tggggatcaa   1080

attcgcaagg gagctgcact taacgcaatc cagattgctg agatgttgct atgagttctg   1140

gtttttcaag gatctggtac ttaaagatta tgcttctttt gaaacagttt tgtatgtgct   1200

agttgtatgt ggttattcat ttcttttgtg atgtttaact agtccaagta tcttttcaac   1260

gatgtggtag cacactagct ggaaacagtt tttttaaggt cttggtgcgt aatatctgca   1320

atccttttca ccgggaataa caagcactgg ttatggcaaa aaaaaaaaaa aaaaaaaaaa   1380

aaaaaaaaaa a                                                         1391


<210> SEQ ID NO 47
<211> LENGTH: 377
```

```
<212> TYPE: PRT
<213> ORGANISM: Glycine max

<400> SEQUENCE: 47

Ala Arg Ala Ser Leu Ser Val Leu Arg His Asn His Leu Phe Ser Gly
  1               5                  10                  15

Pro Leu Pro Ala Arg Pro Lys Pro Thr Ser Ser Ser Ser Ser Arg Ile
             20                  25                  30

Arg Met Ser Leu Arg Glu Asn Gly Pro Ser Ile Ala Val Val Gly Val
         35                  40                  45

Thr Gly Ala Val Gly Gln Glu Phe Leu Ser Val Leu Ser Asp Arg Asp
     50                  55                  60

Phe Pro Tyr Arg Ser Ile His Met Leu Ala Ser Lys Arg Ser Ala Gly
 65                  70                  75                  80

Arg Arg Ile Thr Phe Glu Asp Arg Asp Tyr Val Val Gln Glu Leu Thr
                 85                  90                  95

Pro Glu Ser Phe Asp Gly Val Asp Ile Ala Leu Phe Ser Ala Gly Gly
            100                 105                 110

Ser Ile Ser Lys His Phe Gly Pro Ile Ala Val Asn Arg Gly Thr Val
        115                 120                 125

Val Val Asp Asn Ser Ser Ala Phe Arg Met Asn Glu Lys Val Pro Leu
    130                 135                 140

Val Ile Pro Glu Val Asn Pro Glu Ala Met Gln Asn Ile Lys Ala Gly
145                 150                 155                 160

Thr Gly Lys Gly Ala Leu Ile Ala Asn Pro Asn Cys Ser Thr Ile Ile
                165                 170                 175

Cys Leu Met Ala Ala Thr Pro Leu His Arg Arg Ala Lys Val Leu Arg
            180                 185                 190

Met Val Val Ser Thr Tyr Gln Ala Ala Ser Gly Ala Gly Ala Ala Ala
        195                 200                 205

Met Glu Glu Leu Glu Leu Gln Thr Arg Glu Val Leu Glu Gly Lys Pro
    210                 215                 220

Pro Thr Cys Lys Ile Phe Asn Arg Gln Tyr Ala Phe Asn Leu Phe Ser
225                 230                 235                 240

His Asn Ala Ser Val Leu Ser Asn Gly Tyr Asn Glu Glu Glu Met Lys
                245                 250                 255

Met Val Lys Glu Thr Arg Lys Ile Trp Asn Asp Lys Asp Val Lys Val
            260                 265                 270

Thr Ala Thr Cys Ile Arg Val Pro Ile Met Arg Ala His Ala Glu Ser
        275                 280                 285

Val Asn Leu Gln Phe Glu Arg Pro Leu Asp Glu Asp Thr Ala Arg Asp
    290                 295                 300

Ile Leu Lys Asn Ala Pro Gly Val Val Val Ile Asp Asp Arg Glu Ser
305                 310                 315                 320

Asn His Phe Pro Thr Pro Leu Glu Val Ser Asn Lys Asp Asp Val Ala
                325                 330                 335

Val Gly Arg Ile Arg Gln Asp Leu Ser Gln Asp Gly Asn Gln Gly Leu
            340                 345                 350

Asp Ile Phe Val Cys Gly Asp Gln Ile Arg Lys Gly Ala Ala Leu Asn
        355                 360                 365

Ala Ile Gln Ile Ala Glu Met Leu Leu
    370                 375

<210> SEQ ID NO 48
```

<211> LENGTH: 1470
<212> TYPE: DNA
<213> ORGANISM: Glycine max

<400> SEQUENCE: 48

```
gcacgaggtc tgttttaaaa tccaacactt aatctctctc ttcgcagcct aaaatcccaa     60
tggcttcact ctctgttttg cgccacaacc acctcttctc gggccccctc ccggcccgcc    120
ccaagcccac ctcctcctcc tcctccagga tccgaatgtc cctccgcgag aacggcccct    180
ccatcgccgt cgtgggcgtc accggcgccg tcggccagga gttcctctcc gtcctctccg    240
accgcgactt cccctaccgc tccattcata tgctggcttc caagcgctcc gctggccgcc    300
gcatcacctt cgaggacagg gactacgtcg tccaggagct cacgccggag agcttcgacg    360
gtgtcgacat cgcgctcttc agcgccggcg gctccatcag caagcacttc ggccccatcg    420
ccgtcaatcg tggaacggtc gtggtcgaca acagctccgc gtttcggatg gacgagaagg    480
tgcctttggt aattcccgaa gtgaaccccg aagcaatgca aaacatcaaa gccggaacgg    540
gaaagggcgc actcattgct aaccctaatt gctccaccat tagatgcttg aaggctgcta    600
cccctcttca tcgacgtgcc aaggtgttac gtatggttgt tagtacctat caggctgcga    660
gtggtgctgg tgctgctgca atggaagagc ttgagctgca aactcgtgag gtgttggaag    720
gaaaaccacc cacttgtaaa atatttaacc gacagtatgc ttttaatcta ttctcacata    780
atgcgtctgt tctttcaaat ggatataatg aagaagaaat gaaaatggtc aaggagacca    840
ggaaaatctg gaatgacaag gatgttaaag taactgccac atgcatacga gttcccatca    900
tgcgagctca tgctgagagt gtgaatcttc aatttgaaag accccttgat gaggacactg    960
caagagatat tctgaaaaat gctccaggtg tagtggttat tgatgatcgt gaatccaatc   1020
attttcctac tccactggaa gtgtcaaaca aggatgatgt tgctgttggt aggattcggc   1080
aggacctgtc tcaggatggg aatcaagggt tggacatctt tgtatgtggg gatcaaattc   1140
gcaagggagc tgcacttaac gcaatccaga ttgctgagat gttgctatga gttctggttt   1200
ttcaaggatc tggtacttaa agattatgct tcttttgaaa cagttttgta tgtgctagtt   1260
gtatgtggtt attcatttct tttgtgatgt ttaactagtc caagtatctt ttcaacgatg   1320
tggtagcaca ctagctggaa acagtttttt taaggtcttg gtgcgtaata tctgcaatcc   1380
ttttcaccgg gaataacaag cactggtttt ggcaaaaaaa aaaaaaaaaa aaaaaaaaaa   1440
aaaaaaaaaa aaaaaaaaaa aaaaaaaaaa                                    1470
```

<210> SEQ ID NO 49
<211> LENGTH: 376
<212> TYPE: PRT
<213> ORGANISM: Glycine max

<400> SEQUENCE: 49

```
Met Ala Ser Leu Ser Val Leu Arg His Asn His Leu Phe Ser Gly Pro
  1               5                  10                  15

Leu Pro Ala Arg Pro Lys Pro Thr Ser Ser Ser Ser Ser Arg Ile Arg
             20                  25                  30

Met Ser Leu Arg Glu Asn Gly Pro Ser Ile Ala Val Val Gly Val Thr
         35                  40                  45

Gly Ala Val Gly Gln Glu Phe Leu Ser Val Leu Ser Asp Arg Asp Phe
     50                  55                  60

Pro Tyr Arg Ser Ile His Met Leu Ala Ser Lys Arg Ser Ala Gly Arg
 65                  70                  75                  80
```

-continued

```
Arg Ile Thr Phe Glu Asp Arg Asp Tyr Val Val Gln Glu Leu Thr Pro
                85                  90                  95

Glu Ser Phe Asp Gly Val Asp Ile Ala Leu Phe Ser Ala Gly Gly Ser
            100                 105                 110

Ile Ser Lys His Phe Gly Pro Ile Ala Val Asn Arg Gly Thr Val Val
        115                 120                 125

Val Asp Asn Ser Ser Ala Phe Arg Met Asp Glu Lys Val Pro Leu Val
    130                 135                 140

Ile Pro Glu Val Asn Pro Glu Ala Met Gln Asn Ile Lys Ala Gly Thr
145                 150                 155                 160

Gly Lys Gly Ala Leu Ile Ala Asn Pro Asn Cys Ser Thr Ile Arg Cys
                165                 170                 175

Leu Lys Ala Ala Thr Pro Leu His Arg Arg Ala Lys Val Leu Arg Met
            180                 185                 190

Val Val Ser Thr Tyr Gln Ala Ala Ser Gly Ala Gly Ala Ala Ala Met
        195                 200                 205

Glu Glu Leu Glu Leu Gln Thr Arg Glu Val Leu Glu Gly Lys Pro Pro
    210                 215                 220

Thr Cys Lys Ile Phe Asn Arg Gln Tyr Ala Phe Asn Leu Phe Ser His
225                 230                 235                 240

Asn Ala Ser Val Leu Ser Asn Gly Tyr Asn Glu Glu Glu Met Lys Met
                245                 250                 255

Val Lys Glu Thr Arg Lys Ile Trp Asn Asp Lys Asp Val Lys Val Thr
            260                 265                 270

Ala Thr Cys Ile Arg Val Pro Ile Met Arg Ala His Ala Glu Ser Val
        275                 280                 285

Asn Leu Gln Phe Glu Arg Pro Leu Asp Glu Asp Thr Ala Arg Asp Ile
    290                 295                 300

Leu Lys Asn Ala Pro Gly Val Val Val Ile Asp Asp Arg Glu Ser Asn
305                 310                 315                 320

His Phe Pro Thr Pro Leu Glu Val Ser Asn Lys Asp Asp Val Ala Val
                325                 330                 335

Gly Arg Ile Arg Gln Asp Leu Ser Gln Asp Gly Asn Gln Gly Leu Asp
            340                 345                 350

Ile Phe Val Cys Gly Asp Gln Ile Arg Lys Gly Ala Ala Leu Asn Ala
        355                 360                 365

Ile Gln Ile Ala Glu Met Leu Leu
    370                 375
```

<210> SEQ ID NO 50
<211> LENGTH: 1609
<212> TYPE: DNA
<213> ORGANISM: Triticum aestivum

<400> SEQUENCE: 50

```
caccaccacc cacctaccca aatcccagcc gccctaaaac cctaggccgc caaacccgcc     60

gccgccgccg ccgcaatgca ggccgccgca gccgtccacc ggccacacct cctcgcggcg    120

tccccgctcg gggccgcgc cagccgccgg ccctccacgg tccgcatggc gctccgcgag    180

gacgggccct ccgtggccat cgtgggcgcc accggcgcgg tggggcagga gttcctccgc    240

gtcatcaccg cccgcgactt cccctaccgc agcctgcgcc tcctcgccag cgagcgctcc    300

gcgggcaagc gcatcgactt cgagggccgg gactacaccg tccaggacct cgcggcgccg    360

ggggccttcg acggggtcga catcgcgctc ttcagcgccg gcgggagcat cagccgcgcc    420
```

-continued

```
cacgcgcccg ccgccgtcgc cagcggcgcc gtcgtcgtgg ataacagctc cgcctaccgg    480

atggaccccg acgtgccgct cgtcatcccg gaggttaacc ccgaggccat ggccgacgtc    540

cggctcggga aggggctat tgtggccaac cccaactgtt ccaccatcat ctgcctcatg    600

gctgtcacgc cgctgcatcg ccacgccaag gtgaaaagga tggttgtcag cacataccaa    660

gcagcaagtg gtgctggtgc tgcagccatg gaagaactca aacttcagac tcgagaggtc    720

ttggaaggaa agccaccaac ctgtaacatt ttcagtcaac agtatgcttt taatatattt    780

tcgcataatg cacctattgt tgaaaatggc tataatgagg aagagatgaa aatggtgaag    840

gagaccagaa aaatctggaa tgacaaggat gtaagagtaa ctgcaacttg tatacgggtt    900

cctacgatgc gcgcgcatgc cgaaagcgtg aatctacagt ttgaaaagcc acttgatgag    960

gacactgcca gagaaatctt gagggcagct cctggtgtta ccattagtga cgaccgtgct   1020

gccaaccgct tccctacacc actggaggta tcggataaag atgacgtatc agttggtagg   1080

attcgccagg acttgtcaca agatgataac agagggttgg agttatttgt ctgtggagac   1140

cagatacgta aaggcgccgc gctgaacgct gtgcagattg ctgaaatgct actgaagtga   1200

ccgccttttt accattgtct catgtgccac gttgctctat ccattgatgg attgatgtac   1260

tctagtcact ttcaacccag ttttggtcgt cgtctttttt gtaatctgtc aacctagcag   1320

aagaagtgta agacgggctt tagtcatctg ttgcacacaa aagtgcagcc acaagtttag   1380

aaaaggaggg ttttcacttg ttcggatttt gccttaggtt ggactttgtt gcaagtttgt   1440

cgtttgtttc ttgaaagctg gtctgctgta actttacccc caaagccctc gagataacga   1500

ggcgtcctgt ggggacctaa aaaaaaaaaa aaaaaaaaaa aaaaaacccc aaaaaaaaaa   1560

aaaaaaaaaa aaaaaaaaaa aaaaaaaaaa aaaaaaaaaa aaaaaaaaa               1609
```

```
<210> SEQ ID NO 51
<211> LENGTH: 374
<212> TYPE: PRT
<213> ORGANISM: Triticum aestivum

<400> SEQUENCE: 51

Met Gln Ala Ala Ala Ala Val His Arg Pro His Leu Leu Ala Ala Ser
  1               5                  10                  15

Pro Leu Gly Gly Arg Ala Ser Arg Arg Pro Ser Thr Val Arg Met Ala
             20                  25                  30

Leu Arg Glu Asp Gly Pro Ser Val Ala Ile Val Gly Ala Thr Gly Ala
         35                  40                  45

Val Gly Gln Glu Phe Leu Arg Val Ile Thr Ala Arg Asp Phe Pro Tyr
     50                  55                  60

Arg Ser Leu Arg Leu Leu Ala Ser Glu Arg Ser Ala Gly Lys Arg Ile
 65                  70                  75                  80

Asp Phe Glu Gly Arg Asp Tyr Thr Val Gln Asp Leu Ala Ala Pro Gly
                 85                  90                  95

Ala Phe Asp Gly Val Asp Ile Ala Leu Phe Ser Ala Gly Gly Ser Ile
            100                 105                 110

Ser Arg Ala His Ala Pro Ala Ala Val Ala Ser Gly Ala Val Val Val
        115                 120                 125

Asp Asn Ser Ser Ala Tyr Arg Met Asp Pro Asp Val Pro Leu Val Ile
    130                 135                 140

Pro Glu Val Asn Pro Glu Ala Met Ala Asp Val Arg Leu Gly Lys Gly
145                 150                 155                 160

Ala Ile Val Ala Asn Pro Asn Cys Ser Thr Ile Ile Cys Leu Met Ala
```

-continued

```
                165                 170                 175

Val Thr Pro Leu His Arg His Ala Lys Val Lys Arg Met Val Val Ser
            180                 185                 190

Thr Tyr Gln Ala Ala Ser Gly Ala Gly Ala Ala Ala Met Glu Glu Leu
        195                 200                 205

Lys Leu Gln Thr Arg Glu Val Leu Glu Gly Lys Pro Pro Thr Cys Asn
    210                 215                 220

Ile Phe Ser Gln Gln Tyr Ala Phe Asn Ile Phe Ser His Asn Ala Pro
225                 230                 235                 240

Ile Val Glu Asn Gly Tyr Asn Glu Glu Glu Met Lys Met Val Lys Glu
                245                 250                 255

Thr Arg Lys Ile Trp Asn Asp Lys Asp Val Arg Val Thr Ala Thr Cys
            260                 265                 270

Ile Arg Val Pro Thr Met Arg Ala His Ala Glu Ser Val Asn Leu Gln
        275                 280                 285

Phe Glu Lys Pro Leu Asp Glu Asp Thr Ala Arg Glu Ile Leu Arg Ala
    290                 295                 300

Ala Pro Gly Val Thr Ile Ser Asp Asp Arg Ala Ala Asn Arg Phe Pro
305                 310                 315                 320

Thr Pro Leu Glu Val Ser Asp Lys Asp Asp Val Ser Val Gly Arg Ile
                325                 330                 335

Arg Gln Asp Leu Ser Gln Asp Asp Asn Arg Gly Leu Glu Leu Phe Val
            340                 345                 350

Cys Gly Asp Gln Ile Arg Lys Gly Ala Ala Leu Asn Ala Val Gln Ile
        355                 360                 365

Ala Glu Met Leu Leu Lys
    370


<210> SEQ ID NO 52
<211> LENGTH: 340
<212> TYPE: PRT
<213> ORGANISM: Aquifex aeolicus

<400> SEQUENCE: 52

Met Gly Tyr Arg Val Ala Ile Val Gly Ala Thr Gly Glu Val Gly Arg
  1               5                  10                  15

Thr Phe Leu Lys Val Leu Glu Glu Arg Asn Phe Pro Val Asp Glu Leu
             20                  25                  30

Val Leu Tyr Ala Ser Glu Arg Ser Glu Gly Lys Val Leu Thr Phe Lys
         35                  40                  45

Gly Lys Glu Tyr Thr Val Lys Ala Leu Asn Lys Glu Asn Ser Phe Lys
     50                  55                  60

Gly Ile Asp Ile Ala Leu Phe Ser Ala Gly Gly Ser Thr Ser Lys Glu
 65                  70                  75                  80

Trp Ala Pro Lys Phe Ala Lys Asp Gly Val Val Val Ile Asp Asn Ser
                 85                  90                  95

Ser Ala Trp Arg Met Asp Pro Asp Val Pro Leu Val Val Pro Glu Val
            100                 105                 110

Asn Pro Glu Asp Val Lys Asp Phe Lys Lys Lys Gly Ile Ile Ala Asn
        115                 120                 125

Pro Asn Cys Ser Thr Ile Gln Met Val Val Ala Leu Lys Pro Ile Tyr
    130                 135                 140

Asp Lys Ala Gly Ile Lys Arg Val Val Val Ser Thr Tyr Gln Ala Val
145                 150                 155                 160
```

-continued

```
Ser Gly Ala Gly Ala Lys Ala Ile Glu Asp Leu Lys Asn Gln Thr Lys
                165                 170                 175

Ala Trp Cys Glu Gly Lys Glu Met Pro Lys Ala Gln Lys Phe Pro His
            180                 185                 190

Gln Ile Ala Phe Asn Ala Leu Pro His Ile Asp Val Phe Phe Glu Asp
        195                 200                 205

Gly Tyr Thr Lys Glu Glu Asn Lys Met Leu Tyr Glu Thr Arg Lys Ile
    210                 215                 220

Met His Asp Glu Asn Ile Lys Val Ser Ala Thr Cys Val Arg Ile Pro
225                 230                 235                 240

Val Phe Tyr Gly His Ser Glu Ser Ile Ser Met Glu Thr Glu Lys Glu
                245                 250                 255

Ile Ser Pro Glu Glu Ala Arg Glu Val Leu Lys Asn Ala Pro Gly Val
            260                 265                 270

Ile Val Ile Asp Asn Pro Gln Asn Asn Glu Tyr Pro Met Pro Ile Met
        275                 280                 285

Ala Glu Gly Arg Asp Glu Val Phe Val Gly Arg Ile Arg Lys Asp Arg
    290                 295                 300

Val Phe Glu Pro Gly Leu Ser Met Trp Val Val Ala Asp Asn Ile Arg
305                 310                 315                 320

Lys Gly Ala Ala Thr Asn Ala Val Gln Ile Ala Glu Leu Leu Val Lys
                325                 330                 335

Glu Gly Leu Ile
            340
```

<210> SEQ ID NO 53
<211> LENGTH: 1727
<212> TYPE: DNA
<213> ORGANISM: Glycine max

<400> SEQUENCE: 53

```
ttgcaacaca cattgtcttg tcggcaaaat cttccaccaa caacacacag ccatggcagg      60

ctcaaacatt ctttctcact ctccttccct tcccaaaacc tacagccact ccttaaacca     120

aaacgcgtta tcccaaaagc tttttttct gcccctcaaa ttcaaagcca ccacaaaacc     180

acgtgctctc agagcggttc tctcgcagaa cgctgtcaaa acctcggtgg aggacacaaa     240

gaacgctcat tttcagcact gtttcaccaa atccgaagat gggtatctgt actgtgaggg     300

cctcaaggtg catgacatca tggaatctgt tgagagaaga cctttctatt tgtacagcaa     360

gccccagata actaggaatg ttgaagccta caaggatgca ttggaagggt tgaactccat     420

aattggttat gccattaagg ccaataataa cttgaagatt ttggaacatt tgaggcactt     480

gggttgtggt gctgtgcttg ttagtgggaa tgagctgaag ttggctcttc gagctggctt     540

tgatcccaca aggtgtatct ttaatgggaa tgggaaaatc ttggaggatt tggtcttggc     600

tgctcaggaa ggtgtgtttg tcaacattga tagtgagttt gacttggaaa acattgtaga     660

ggctgcaaaa agggctggga agaaggtcaa tgttttactt cggattaatc ctgatgtgga     720

tccacaggtt catccttatg ttgccactgg gaataagaac tctaaatttg gcattagaaa     780

tgagaagctg cagtgctttt tagatgcagt gaaggaacat cctaatgagc tcaaacttgt     840

aggggcccac tgccatcttg gttcaacaat taccaaggtt gacattttca gggatgcagc     900

caccattatg atcaactaca ttgaccaaat ccgagatcag ggttttgaag ttgattactt     960

aaatattggt ggaggacttg ggatagatta ttatcattct ggtgccatcc ttcctacacc    1020

tagagatctc attgacactg tacgagatct tgttatttca cgtggtctta atctcatcat    1080
```

-continued

```
tgaaccagga agatcactca ttgcaaacac gtgttgctta gttaaccggg tgacaggtgt   1140

taaaactaat ggatctaaaa acttcattgt aattgatgga agtatggctg aacttatccg   1200

ccctagtctt tatgatgctt accagcatat agagctggtt tcccctgccc cgtcaaatgc   1260

tgaaacagaa acttttgatg tggttggccc tgtctgtgag tctgcagatt tcttaggaaa   1320

aggaagagaa cttcctactc cagccaaggg tactggtttg gttgttcatg atgctggtgc   1380

ttattgcatg agcatggcat caacctacaa tctaaagatg cggcctcctg agtattgggt   1440

tgaagatgat ggatcagtga gcaaaataag acatggagag acttttgaag accacattcg   1500

gtttttgag gggctttgag ctaataattt atcttgtagg aaagaaggct ggagaattgt   1560

tatgtacttg gagtttgaat ctttcctcgt caatgaatgc atgactcttg tagttctgtt   1620

tcttccgttc taattgaatg ttgactccca tgacaggaac agagaataaa gttgatttca   1680

gttaaaaaaa aaaaaaaaaa aaaaaaaaaa aaaaaaaaaa aaaaaaa                 1727
```

<210> SEQ ID NO 54
<211> LENGTH: 505
<212> TYPE: PRT
<213> ORGANISM: Glycine max

<400> SEQUENCE: 54

```
Cys Asn Thr His Cys Leu Val Gly Lys Ile Phe His Gln Gln His Thr
  1               5                  10                  15

Ala Met Ala Gly Ser Asn Ile Leu Ser His Ser Pro Ser Leu Pro Lys
             20                  25                  30

Thr Tyr Ser His Ser Leu Asn Gln Asn Ala Leu Ser Gln Lys Leu Phe
         35                  40                  45

Phe Leu Pro Leu Lys Phe Lys Ala Thr Thr Lys Pro Arg Ala Leu Arg
     50                  55                  60

Ala Val Leu Ser Gln Asn Ala Val Lys Thr Ser Val Glu Asp Thr Lys
 65                  70                  75                  80

Asn Ala His Phe Gln His Cys Phe Thr Lys Ser Glu Asp Gly Tyr Leu
                 85                  90                  95

Tyr Cys Glu Gly Leu Lys Val His Asp Ile Met Glu Ser Val Glu Arg
            100                 105                 110

Arg Pro Phe Tyr Leu Tyr Ser Lys Pro Gln Ile Thr Arg Asn Val Glu
        115                 120                 125

Ala Tyr Lys Asp Ala Leu Glu Gly Leu Asn Ser Ile Ile Gly Tyr Ala
    130                 135                 140

Ile Lys Ala Asn Asn Asn Leu Lys Ile Leu Glu His Leu Arg His Leu
145                 150                 155                 160

Gly Cys Gly Ala Val Leu Val Ser Gly Asn Glu Leu Lys Leu Ala Leu
                165                 170                 175

Arg Ala Gly Phe Asp Pro Thr Arg Cys Ile Phe Asn Gly Asn Gly Lys
            180                 185                 190

Ile Leu Glu Asp Leu Val Leu Ala Ala Gln Glu Gly Val Phe Val Asn
        195                 200                 205

Ile Asp Ser Glu Phe Asp Leu Glu Asn Ile Val Glu Ala Ala Lys Arg
    210                 215                 220

Ala Gly Lys Lys Val Asn Val Leu Leu Arg Ile Asn Pro Asp Val Asp
225                 230                 235                 240

Pro Gln Val His Pro Tyr Val Ala Thr Gly Asn Lys Asn Ser Lys Phe
                245                 250                 255
```

-continued

```
Gly Ile Arg Asn Glu Lys Leu Gln Cys Phe Leu Asp Ala Val Lys Glu
            260                 265                 270

His Pro Asn Glu Leu Lys Leu Val Gly Ala His Cys His Leu Gly Ser
        275                 280                 285

Thr Ile Thr Lys Val Asp Ile Phe Arg Asp Ala Ala Thr Ile Met Ile
    290                 295                 300

Asn Tyr Ile Asp Gln Ile Arg Asp Gln Gly Phe Glu Val Asp Tyr Leu
305                 310                 315                 320

Asn Ile Gly Gly Gly Leu Gly Ile Asp Tyr Tyr His Ser Gly Ala Ile
                325                 330                 335

Leu Pro Thr Pro Arg Asp Leu Ile Asp Thr Val Arg Asp Leu Val Ile
            340                 345                 350

Ser Arg Gly Leu Asn Leu Ile Ile Glu Pro Gly Arg Ser Leu Ile Ala
        355                 360                 365

Asn Thr Cys Cys Leu Val Asn Arg Val Thr Gly Val Lys Thr Asn Gly
    370                 375                 380

Ser Lys Asn Phe Ile Val Ile Asp Gly Ser Met Ala Glu Leu Ile Arg
385                 390                 395                 400

Pro Ser Leu Tyr Asp Ala Tyr Gln His Ile Glu Leu Val Ser Pro Ala
                405                 410                 415

Pro Ser Asn Ala Glu Thr Glu Thr Phe Asp Val Val Gly Pro Val Cys
            420                 425                 430

Glu Ser Ala Asp Phe Leu Gly Lys Gly Arg Glu Leu Pro Thr Pro Ala
        435                 440                 445

Lys Gly Thr Gly Leu Val Val His Asp Ala Gly Ala Tyr Cys Met Ser
    450                 455                 460

Met Ala Ser Thr Tyr Asn Leu Lys Met Arg Pro Pro Glu Tyr Trp Val
465                 470                 475                 480

Glu Asp Asp Gly Ser Val Ser Lys Ile Arg His Gly Glu Thr Phe Glu
                485                 490                 495

Asp His Ile Arg Phe Phe Glu Gly Leu
            500                 505
```

<210> SEQ ID NO 55
<211> LENGTH: 858
<212> TYPE: DNA
<213> ORGANISM: Triticum aestivum

<400> SEQUENCE: 55

```
tttgagttgg agtacctgaa tattggaggt ggtttgggga tagactacca ccacactggt      60

gcagtcttgc ctacacctat ggatcttatc aacactgtcc gggaattggt cctctcacgg     120

gatcttactc tcattattga acctggaaga tccctgatcg ccaatacttg ctgcttcgtc     180

aataaggtca ctggtgtaaa atcgaatggc acgaagaatt tcattgtagt tgatggcagc     240

atggccgagc tcatcaggcc tagtctatat ggagcatatc agcatataga actagtttct     300

ccctctccag gtgcagaagt agcaaccttc gatattgttg ggccagtctg cgaatctgca     360

gatttccttg gcaaagacag ggagcttcca acacctgaca agggagctgg tttggttgtc     420

cacgacgcag gagcctactg catgagcatg gcttcgacct acaacctgaa gatgaggcca     480

gccgagtatt gggtagagga cgatgggtcc attgttaaga tcaggcacgg tgaaacattt     540

gacgactaca tgaagttctt tgatggtctt cctgcctagg cccttttatc ttgttttggg     600

caagcgtagc ccttttcatt tgatgagcgc atctcgtgga agattcgtgt gggaaaacta     660

ttcacttgtt tgttatgtgg gtcatcccca tcaagcatgg gggtttttat ttgttagaat     720
```

```
agagtccaac aagtttagtg attgtagaga ttgaatggac ttactgcatt gttatcaatt    780

cttgtttata ctatataaag ggtccgactc ctcccaataa agttaaagaa tattgttgtt    840

tacttttatc taaaaaaa                                                  858


<210> SEQ ID NO 56
<211> LENGTH: 192
<212> TYPE: PRT
<213> ORGANISM: Triticum aestivum

<400> SEQUENCE: 56

Phe Glu Leu Glu Tyr Leu Asn Ile Gly Gly Gly Leu Gly Ile Asp Tyr
  1               5                  10                  15

His His Thr Gly Ala Val Leu Pro Thr Pro Met Asp Leu Ile Asn Thr
             20                  25                  30

Val Arg Glu Leu Val Leu Ser Arg Asp Leu Thr Leu Ile Ile Glu Pro
         35                  40                  45

Gly Arg Ser Leu Ile Ala Asn Thr Cys Cys Phe Val Asn Lys Val Thr
     50                  55                  60

Gly Val Lys Ser Asn Gly Thr Lys Asn Phe Ile Val Val Asp Gly Ser
 65                  70                  75                  80

Met Ala Glu Leu Ile Arg Pro Ser Leu Tyr Gly Ala Tyr Gln His Ile
                 85                  90                  95

Glu Leu Val Ser Pro Ser Pro Gly Ala Glu Val Ala Thr Phe Asp Ile
            100                 105                 110

Val Gly Pro Val Cys Glu Ser Ala Asp Phe Leu Gly Lys Asp Arg Glu
        115                 120                 125

Leu Pro Thr Pro Asp Lys Gly Ala Gly Leu Val Val His Asp Ala Gly
    130                 135                 140

Ala Tyr Cys Met Ser Met Ala Ser Thr Tyr Asn Leu Lys Met Arg Pro
145                 150                 155                 160

Ala Glu Tyr Trp Val Glu Asp Asp Gly Ser Ile Val Lys Ile Arg His
                165                 170                 175

Gly Glu Thr Phe Asp Asp Tyr Met Lys Phe Phe Asp Gly Leu Pro Ala
            180                 185                 190


<210> SEQ ID NO 57
<211> LENGTH: 526
<212> TYPE: PRT
<213> ORGANISM: Arabidopsis thaliana

<400> SEQUENCE: 57

Met Gly Gln Thr Asn Ser Glu Thr Gln Gln Ala Arg Leu Tyr Thr Gln
  1               5                  10                  15

Asn Ser Gln Lys Gln Leu Leu Arg Ser Phe Leu Leu Leu His Leu Ile
             20                  25                  30

Phe Gly Tyr Gln Ser His Lys Thr Leu Arg Met Ala Ala Ala Thr Gln
         35                  40                  45

Phe Leu Ser Gln Pro Ser Ser Leu Asn Pro His Gln Leu Lys Asn Gln
     50                  55                  60

Thr Ser Gln Arg Ser Arg Ser Ile Pro Val Leu Ser Leu Lys Ser Thr
 65                  70                  75                  80

Leu Lys Pro Leu Lys Arg Leu Ser Val Lys Ala Ala Val Val Ser Gln
                 85                  90                  95

Asn Ser Ser Lys Thr Val Thr Lys Phe Asp His Cys Phe Lys Lys Ser
            100                 105                 110
```

-continued

```
Ser Asp Gly Phe Leu Tyr Cys Glu Gly Thr Lys Val Glu Asp Ile Met
        115                 120                 125

Glu Ser Val Glu Arg Arg Pro Phe Tyr Leu Tyr Ser Lys Pro Gln Ile
    130                 135                 140

Thr Arg Asn Leu Glu Ala Tyr Lys Glu Ala Leu Glu Gly Val Ser Ser
145                 150                 155                 160

Val Ile Gly Tyr Ala Ile Lys Ala Asn Asn Asn Leu Lys Ile Leu Glu
                165                 170                 175

His Leu Arg Ser Leu Gly Cys Gly Ala Val Leu Val Ser Gly Asn Glu
            180                 185                 190

Leu Arg Leu Ala Leu Arg Ala Gly Phe Asp Pro Thr Lys Cys Ile Phe
        195                 200                 205

Asn Gly Asn Gly Lys Ser Leu Glu Asp Leu Val Leu Ala Ala Gln Glu
    210                 215                 220

Gly Val Phe Val Asn Val Asp Ser Glu Phe Asp Leu Asn Asn Ile Val
225                 230                 235                 240

Glu Ala Ser Arg Ile Ser Gly Lys Gln Val Asn Val Leu Leu Arg Ile
                245                 250                 255

Asn Pro Asp Val Asp Pro Gln Val His Pro Tyr Val Ala Thr Gly Asn
            260                 265                 270

Lys Asn Ser Lys Phe Gly Ile Arg Asn Glu Lys Leu Gln Trp Phe Leu
        275                 280                 285

Asp Gln Val Lys Ala His Pro Lys Glu Leu Lys Leu Val Gly Ala His
    290                 295                 300

Cys His Leu Gly Ser Thr Ile Thr Lys Val Asp Ile Phe Arg Asp Ala
305                 310                 315                 320

Ala Val Leu Met Ile Glu Tyr Ile Asp Glu Ile Arg Arg Gln Gly Phe
                325                 330                 335

Glu Val Ser Tyr Leu Asn Ile Gly Gly Gly Leu Gly Ile Asp Tyr Tyr
            340                 345                 350

His Ala Gly Ala Val Leu Pro Thr Pro Met Asp Leu Ile Asn Thr Val
        355                 360                 365

Arg Glu Leu Val Leu Ser Arg Asp Leu Asn Leu Ile Ile Glu Pro Gly
    370                 375                 380

Arg Ser Leu Ile Ala Asn Thr Cys Cys Phe Val Asn His Val Thr Gly
385                 390                 395                 400

Val Lys Thr Asn Gly Thr Lys Asn Phe Ile Val Ile Asp Gly Ser Met
                405                 410                 415

Ala Glu Leu Ile Arg Pro Ser Leu Tyr Asp Ala Tyr Gln His Ile Glu
            420                 425                 430

Leu Val Ser Pro Pro Pro Ala Glu Ala Glu Val Thr Lys Phe Asp Val
        435                 440                 445

Val Gly Pro Val Cys Glu Ser Ala Asp Phe Leu Gly Lys Asp Arg Glu
    450                 455                 460

Leu Pro Thr Pro Pro Gln Gly Ala Gly Leu Val Val His Asp Ala Gly
465                 470                 475                 480

Ala Tyr Cys Met Ser Met Ala Ser Thr Tyr Asn Leu Lys Met Arg Pro
                485                 490                 495

Pro Glu Tyr Trp Val Glu Glu Asp Gly Ser Ile Thr Lys Ile Arg His
            500                 505                 510

Ala Glu Thr Phe Asp Asp His Leu Arg Phe Phe Glu Gly Leu
        515                 520                 525
```

<210> SEQ ID NO 58
<211> LENGTH: 1143
<212> TYPE: DNA
<213> ORGANISM: Oryza sativa

<400> SEQUENCE: 58

```
gcacgaggtc gccgccatcg ctgcccttcg cgccctcgat gtcaagtccc acgccgtctc     60

catccacctc accaagggcc tccccctcgg ctccggcctc ggctcctccg ccgcctccgc    120

cgccgccgct gccaaggccg ttgacgccct cttcggctcc ctcctacacc aagatgacct    180

cgtcctcgcg ggcctcgagt ccgagaaagc cgtcagtggc ttccacgccg acaacatcgc    240

cccggccatc ctcggcggct tcgtcctcgt ccgcagctac gaccccttcc acctcatccc    300

gctctcctcc ccacctgccc tccgcctcca cttcgtcctc gtcacgcccg acttcgaggc    360

gcccaccagc aagatgcgtg ccgcgctgcc caaacaggtg gccgtccacc agcacgtccg    420

caactccagc caagcggccg cgcttgtcgc cgctgtgctg caaggggacg ccaccctcat    480

cggctccgca atgtcctccg acggcatcgt ggagccaacc agggcgccgc tgattcctgg    540

catggctgcg gtcaaggccg cggcgttgga agctggggca ttgggctgca ccatcagtgg    600

agcagggcca actgctgtgg ctgtcattga cggggaggag aagggcgagg aggttggccg    660

gaggatggtg gaggcattcg ccaatgccgg caatctcaaa gcaacagcta ctgttgctca    720

gctcgataga gttggtgcca gggttatctc tacctccact ttggagtagg aagatctggg    780

aggactgctc cggtaggtca aatttggaat ggctcacatg gacactagtg ggaggagaag    840

aaggggggat tggtgtgttt tgtaattcct gggctgacca gaacgattgt cagtcagttg    900

ggttgtgaat tgtgtgatgt agtagcaaac tgattcgtgc cggcaattga attgcaataa    960

gctagtggtt gcagcatcac ctggcgaggc gtagctagga gatgcagaaa cagcattttg   1020

acatgtgtgg gtgttgacat gcaacgaata aaatgaatga agctgaattg gggtttaaaa   1080

aaaaaaaaaa aaaaaaaaaa aaaaaaaaaa aaaaaaaaaa aaaaaaaaaa aaaaaaaata   1140

aaa                                                                 1143
```

<210> SEQ ID NO 59
<211> LENGTH: 255
<212> TYPE: PRT
<213> ORGANISM: Oryza sativa

<400> SEQUENCE: 59

```
His Glu Val Ala Ala Ile Ala Ala Leu Arg Ala Leu Asp Val Lys Ser
  1               5                  10                  15

His Ala Val Ser Ile His Leu Thr Lys Gly Leu Pro Leu Gly Ser Gly
             20                  25                  30

Leu Gly Ser Ser Ala Ala Ser Ala Ala Ala Ala Ala Lys Ala Val Asp
         35                  40                  45

Ala Leu Phe Gly Ser Leu Leu His Gln Asp Asp Leu Val Leu Ala Gly
     50                  55                  60

Leu Glu Ser Glu Lys Ala Val Ser Gly Phe His Ala Asp Asn Ile Ala
 65                  70                  75                  80

Pro Ala Ile Leu Gly Gly Phe Val Leu Val Arg Ser Tyr Asp Pro Phe
                 85                  90                  95

His Leu Ile Pro Leu Ser Ser Pro Pro Ala Leu Arg Leu His Phe Val
            100                 105                 110

Leu Val Thr Pro Asp Phe Glu Ala Pro Thr Ser Lys Met Arg Ala Ala
        115                 120                 125
```

```
Leu Pro Lys Gln Val Ala Val His Gln His Val Arg Asn Ser Ser Gln
    130                 135                 140

Ala Ala Ala Leu Val Ala Ala Val Leu Gln Gly Asp Ala Thr Leu Ile
145                 150                 155                 160

Gly Ser Ala Met Ser Ser Asp Gly Ile Val Glu Pro Thr Arg Ala Pro
                165                 170                 175

Leu Ile Pro Gly Met Ala Ala Val Lys Ala Ala Ala Leu Glu Ala Gly
            180                 185                 190

Ala Leu Gly Cys Thr Ile Ser Gly Ala Gly Pro Thr Ala Val Ala Val
        195                 200                 205

Ile Asp Gly Glu Glu Lys Gly Glu Glu Val Gly Arg Arg Met Val Glu
    210                 215                 220

Ala Phe Ala Asn Ala Gly Asn Leu Lys Ala Thr Ala Thr Val Ala Gln
225                 230                 235                 240

Leu Asp Arg Val Gly Ala Arg Val Ile Ser Thr Ser Thr Leu Glu
                245                 250                 255


<210> SEQ ID NO 60
<211> LENGTH: 370
<212> TYPE: PRT
<213> ORGANISM: Arabidopsis thaliana

<400> SEQUENCE: 60

Met Ala Ser Leu Cys Phe Gln Ser Pro Ser Lys Pro Ile Ser Tyr Phe
  1               5                  10                  15

Gln Pro Lys Ser Asn Pro Ser Pro Pro Leu Phe Ala Lys Val Ser Val
             20                  25                  30

Phe Arg Cys Arg Ala Ser Val Gln Thr Leu Val Ala Val Glu Pro Glu
         35                  40                  45

Pro Val Phe Val Ser Val Lys Thr Phe Ala Pro Ala Thr Val Ala Asn
     50                  55                  60

Leu Gly Pro Gly Phe Asp Phe Leu Gly Cys Ala Val Asp Gly Leu Gly
 65                  70                  75                  80

Asp His Val Thr Leu Arg Val Asp Pro Ser Val Arg Ala Gly Glu Val
                 85                  90                  95

Ser Ile Ser Glu Ile Thr Gly Thr Thr Thr Lys Leu Ser Thr Asn Pro
            100                 105                 110

Leu Arg Asn Cys Ala Gly Ile Ala Ala Ile Ala Thr Met Lys Met Leu
        115                 120                 125

Gly Ile Arg Ser Val Gly Leu Ser Leu Asp Leu His Lys Gly Leu Pro
    130                 135                 140

Leu Gly Ser Gly Leu Gly Ser Ser Ala Ala Ser Ala Ala Ala Ala Ala
145                 150                 155                 160

Val Ala Val Asn Glu Ile Phe Gly Arg Lys Leu Gly Ser Asp Gln Leu
                165                 170                 175

Val Leu Ala Gly Leu Glu Ser Glu Ala Lys Val Ser Gly Tyr His Ala
            180                 185                 190

Asp Asn Ile Ala Pro Ala Ile Met Gly Gly Phe Val Leu Ile Arg Asn
        195                 200                 205

Tyr Glu Pro Leu Asp Leu Lys Pro Leu Lys Phe Pro Ser Asp Lys Asp
    210                 215                 220

Leu Phe Phe Val Leu Val Ser Pro Glu Phe Glu Ala Pro Thr Lys Lys
225                 230                 235                 240

Met Arg Ala Ala Leu Pro Thr Glu Ile Pro Met Val His His Val Trp
```

-continued

```
                245                 250                 255

Asn Ser Ser Gln Ala Ala Ala Leu Val Ala Ala Val Leu Glu Gly Asp
            260                 265                 270

Ala Val Met Leu Gly Lys Ala Leu Ser Ser Asp Lys Ile Val Glu Pro
        275                 280                 285

Thr Arg Ala Pro Leu Ile Pro Gly Met Glu Ala Val Lys Lys Ala Ala
    290                 295                 300

Leu Glu Ala Gly Ala Phe Gly Cys Thr Ile Ser Gly Ala Gly Pro Thr
305                 310                 315                 320

Ala Val Ala Val Ile Asp Ser Glu Glu Lys Gly Gln Val Ile Gly Glu
                325                 330                 335

Lys Met Val Glu Ala Phe Trp Lys Val Gly His Leu Lys Ser Val Ala
            340                 345                 350

Ser Val Lys Lys Leu Asp Lys Val Gly Ala Arg Leu Val Asn Ser Val
        355                 360                 365

Ser Arg
    370


<210> SEQ ID NO 61
<211> LENGTH: 1508
<212> TYPE: DNA
<213> ORGANISM: Zea mays

<400> SEQUENCE: 61

aaggatggcg tcgtggtcgt cgccctcagc cgccgccaac gccgcctcgg gcgccccgatt     60

cggcccccttc ccgagcggag ggcagcggct cgcgccgtgt ccgtcgctcg tccgcggaac    120

tcccgccccg acgctcgtcc tcaggctcca cccggacggc cgtggccatg gcctcctcgc    180

gcacaccggc ccctctccct cctcgcggtg ccgcgccgtc gccgccgagg tcgggggcct    240

caacatcgcc aacgacgtca cccagctcat cggcaacaca ccaatggtgt atctcaacaa    300

cgtcgtcaag ggctctgtcg ccaatgtcgc tgctaagctc gagattatgg agccctgctg    360

tagcgtcaag gacaggatag ggtacagtat gataaatgat gctgaacaga agggcttgat    420

tactcctgga aagagtgttt tggtggaagc aacaagtgga aacacaggca ttggtcttgc    480

tttcattgct gcttccaaag gatataagct gatactaaca atgccttcat caatgagcat    540

ggagagaaga gtcctcctta gagcttttgg tgccgaactt gtccttactg atgctgcaaa    600

agggatgaaa ggggccttag ataaggctac agagatttta aacaagacac caaattctta    660

catgcttcaa cagttcgata accctgccaa ccctcaggta cattatgaga ctactggtcc    720

agagatctgg gaggattcaa aggggaaggt ggatatattc attggtggaa ttggaacagg    780

ggggacaata tctggtgccg gccgttttct caaggagaaa aatcctggaa ttaaggttat    840

tggtattgag ccttctgaaa gtaacatact ctccggtgga aaacctggtc cacataagat    900

ccagggaatc ggcgcaggat ttgttccaag gaacttggat agcgatattc ttgatgaagt    960

aattgagata tcaagtgatg aagctgttga gacagcaaaa cagttggctg ttcaggaagg   1020

attactggtt ggaatctcct ctggagcagc cgccgctgct gccataaagg ttgccaaaag   1080

accagagaat gctggaaagc tgatagtggt tgtgtttccg agcttcggcg agaggtacct   1140

ttcatctgtc ctctatcagt ccataagaga agaatgtgag aacatgcaac ctgagccatg   1200

agggagccgt cactttaagc gggcatagta aatgtttctg aaataagacg cgtagccagc   1260

atcagtttgc tccacttgga atcatttggc catgctcact ctatcctttc gctagcctct   1320

atgaccggac ctaaactggt gtgtgagaaa catccacgac tgtcctccca actgctttcc   1380
```

```
taaagccaaa cgataacact ctcaataatt gtctatacga ttgaagctga tttgattggt   1440

aattgtaaac agcttgtctt tggatctttg aagtcaaaca aagtcagttg gttgaatcaa   1500

aaaaaaaa                                                            1508


<210> SEQ ID NO 62
<211> LENGTH: 398
<212> TYPE: PRT
<213> ORGANISM: Zea mays

<400> SEQUENCE: 62

Met Ala Ser Trp Ser Ser Pro Ser Ala Ala Ala Asn Ala Ala Ser Gly
  1               5                  10                  15

Ala Arg Phe Gly Pro Phe Pro Ser Gly Gly Gln Arg Leu Ala Pro Cys
             20                  25                  30

Pro Ser Leu Val Arg Gly Thr Pro Ala Pro Thr Leu Val Leu Arg Leu
         35                  40                  45

His Pro Asp Gly Arg Gly His Gly Leu Leu Ala His Thr Gly Pro Ser
     50                  55                  60

Pro Ser Ser Arg Cys Arg Ala Val Ala Ala Glu Val Gly Gly Leu Asn
 65                  70                  75                  80

Ile Ala Asn Asp Val Thr Gln Leu Ile Gly Asn Thr Pro Met Val Tyr
                 85                  90                  95

Leu Asn Asn Val Val Lys Gly Ser Val Ala Asn Val Ala Ala Lys Leu
            100                 105                 110

Glu Ile Met Glu Pro Cys Cys Ser Val Lys Asp Arg Ile Gly Tyr Ser
        115                 120                 125

Met Ile Asn Asp Ala Glu Gln Lys Gly Leu Ile Thr Pro Gly Lys Ser
    130                 135                 140

Val Leu Val Glu Ala Thr Ser Gly Asn Thr Gly Ile Gly Leu Ala Phe
145                 150                 155                 160

Ile Ala Ala Ser Lys Gly Tyr Lys Leu Ile Leu Thr Met Pro Ser Ser
                165                 170                 175

Met Ser Met Glu Arg Arg Val Leu Leu Arg Ala Phe Gly Ala Glu Leu
            180                 185                 190

Val Leu Thr Asp Ala Ala Lys Gly Met Lys Gly Ala Leu Asp Lys Ala
        195                 200                 205

Thr Glu Ile Leu Asn Lys Thr Pro Asn Ser Tyr Met Leu Gln Gln Phe
    210                 215                 220

Asp Asn Pro Ala Asn Pro Gln Val His Tyr Glu Thr Thr Gly Pro Glu
225                 230                 235                 240

Ile Trp Glu Asp Ser Lys Gly Lys Val Asp Ile Phe Ile Gly Gly Ile
                245                 250                 255

Gly Thr Gly Gly Thr Ile Ser Gly Ala Gly Arg Phe Leu Lys Glu Lys
            260                 265                 270

Asn Pro Gly Ile Lys Val Ile Gly Ile Glu Pro Ser Glu Ser Asn Ile
        275                 280                 285

Leu Ser Gly Gly Lys Pro Gly Pro His Lys Ile Gln Gly Ile Gly Ala
    290                 295                 300

Gly Phe Val Pro Arg Asn Leu Asp Ser Asp Ile Leu Asp Glu Val Ile
305                 310                 315                 320

Glu Ile Ser Ser Asp Glu Ala Val Glu Thr Ala Lys Gln Leu Ala Val
                325                 330                 335

Gln Glu Gly Leu Leu Val Gly Ile Ser Ser Gly Ala Ala Ala Ala Ala
```

-continued

```
            340                 345                 350

Ala Ile Lys Val Ala Lys Arg Pro Glu Asn Ala Gly Lys Leu Ile Val
        355                 360                 365

Val Val Phe Pro Ser Phe Gly Glu Arg Tyr Leu Ser Ser Val Leu Tyr
    370                 375                 380

Gln Ser Ile Arg Glu Glu Cys Glu Asn Met Gln Pro Glu Pro
385                 390                 395


<210> SEQ ID NO 63
<211> LENGTH: 1522
<212> TYPE: DNA
<213> ORGANISM: Oryza sativa

<400> SEQUENCE: 63

gcacgaggtt ctaactacgg aactactccc ctatccaaca cctccgagtc cgagcaacgc      60

aagatggcgt cgtggtcgtc gcccgtcgcc gccgccgcct tgcaggtcca tttcgggtcc     120

tcctgcttct tctccgcccg atcgccacga cagaccctcc tcctaccacc tctcgcccgc     180

aaccctacac tgaccatcca gccccggccc catcccttcc ggaacatcaa ctcctcctcc     240

tcctccagct ggatgtgcca cgccgtcgcc gccgaggtcg agggcctcaa catcgccgac     300

gacgtcaccc agctcatcgg caagactcca atggtatatc tcaacaacat cgtcaaggga     360

tgtgttgcca atgtcgctgc taagctcgag attatggagc cctgttgcag tgtcaaggac     420

aggataggat acagtatgat ttctgatgcg gaagagaaag gcttgataac tcctggaaag     480

agtgttttgg tggaaccaac aagtggaaat acaggcattg gtcttgcctt cattgctgct     540

tccagaggat ataaattaat attgaccatg cctgcatcaa tgagcatgga gagaagagtt     600

ctactcaaag cttttggcgc tgaacttgtc cttactgatg ccgcaaaagg gatgaagggg     660

gctgtagata aggctacaga gattttaaat aagacacctg atgcctatat gctgcagcag     720

tttgacaacc ctgccaaccc aaaggtacat tatgagacta ctgggccaga aatctgggag     780

gattctaaag ggaaggtgga tgtattcatt ggtggaattg gaacaggtgg aacaatatct     840

ggtgctggcc gtttcctgaa agagaaaaat cctggaatta aggttattgg tattgagcct     900

tctgagagta acatactctc tggtggaaaa cctggcccac ataagattca aggcattggg     960

gcaggatttg ttccaaggaa cttggatagt gaagttctcg atgaagtgat tgagatatct    1020

agtgatgagg ctgttgagac agcaaagcaa ttggctcttc aggaaggatt actggttgga    1080

atttcatctg gggcagcagc agcagctgcc attaaagttg caaaaagacc agaaaatgct    1140

ggaaagttgg tagtggttgt gtttccaagc tttggtgaga ggtacctttc atctatcctt    1200

tttcagtcga taagagaaga atgtgagaag ttgcaacctg aaccatgagc ctaacttcag    1260

tgttcacaac atcataattg tttctgagat ttctggccat tagttttttt ttctgagaag    1320

tatcatacca ctccatagct gtttgttcga taaataaaac agttaccttt gcacttataa    1380

tgaggcttgt gagggtactg tgaaatttct ctgaacatct tctactcttc tcttttatcc    1440

ttaaatcaat ctgggagcag tttgtaatac atacgtaaat ttaaagctgg gtgtttggta    1500

attgtaaaaa aaaaaaaaaa aa                                             1522


<210> SEQ ID NO 64
<211> LENGTH: 415
<212> TYPE: PRT
<213> ORGANISM: Oryza sativa

<400> SEQUENCE: 64
```

-continued

```
Ala Arg Gly Ser Asn Tyr Gly Thr Thr Pro Leu Ser Asn Thr Ser Glu
  1               5                  10                  15

Ser Glu Gln Arg Lys Met Ala Ser Trp Ser Ser Pro Val Ala Ala Ala
             20                  25                  30

Ala Leu Gln Val His Phe Gly Ser Ser Cys Phe Phe Ser Ala Arg Ser
         35                  40                  45

Pro Arg Gln Thr Leu Leu Leu Pro Pro Leu Ala Arg Asn Pro Thr Leu
     50                  55                  60

Thr Ile Gln Pro Arg Pro His Pro Phe Arg Asn Ile Asn Ser Ser Ser
 65                  70                  75                  80

Ser Ser Ser Trp Met Cys His Ala Val Ala Ala Glu Val Glu Gly Leu
                 85                  90                  95

Asn Ile Ala Asp Asp Val Thr Gln Leu Ile Gly Lys Thr Pro Met Val
            100                 105                 110

Tyr Leu Asn Asn Ile Val Lys Gly Cys Val Ala Asn Val Ala Ala Lys
        115                 120                 125

Leu Glu Ile Met Glu Pro Cys Cys Ser Val Lys Asp Arg Ile Gly Tyr
    130                 135                 140

Ser Met Ile Ser Asp Ala Glu Glu Lys Gly Leu Ile Thr Pro Gly Lys
145                 150                 155                 160

Ser Val Leu Val Glu Pro Thr Ser Gly Asn Thr Gly Ile Gly Leu Ala
                165                 170                 175

Phe Ile Ala Ala Ser Arg Gly Tyr Lys Leu Ile Leu Thr Met Pro Ala
            180                 185                 190

Ser Met Ser Met Glu Arg Arg Val Leu Leu Lys Ala Phe Gly Ala Glu
        195                 200                 205

Leu Val Leu Thr Asp Ala Ala Lys Gly Met Lys Gly Ala Val Asp Lys
    210                 215                 220

Ala Thr Glu Ile Leu Asn Lys Thr Pro Asp Ala Tyr Met Leu Gln Gln
225                 230                 235                 240

Phe Asp Asn Pro Ala Asn Pro Lys Val His Tyr Glu Thr Thr Gly Pro
                245                 250                 255

Glu Ile Trp Glu Asp Ser Lys Gly Lys Val Asp Val Phe Ile Gly Gly
            260                 265                 270

Ile Gly Thr Gly Gly Thr Ile Ser Gly Ala Gly Arg Phe Leu Lys Glu
        275                 280                 285

Lys Asn Pro Gly Ile Lys Val Ile Gly Ile Glu Pro Ser Glu Ser Asn
    290                 295                 300

Ile Leu Ser Gly Gly Lys Pro Gly Pro His Lys Ile Gln Gly Ile Gly
305                 310                 315                 320

Ala Gly Phe Val Pro Arg Asn Leu Asp Ser Glu Val Leu Asp Glu Val
                325                 330                 335

Ile Glu Ile Ser Ser Asp Glu Ala Val Glu Thr Ala Lys Gln Leu Ala
            340                 345                 350

Leu Gln Glu Gly Leu Leu Val Gly Ile Ser Ser Gly Ala Ala Ala Ala
        355                 360                 365

Ala Ala Ile Lys Val Ala Lys Arg Pro Glu Asn Ala Gly Lys Leu Val
    370                 375                 380

Val Val Val Phe Pro Ser Phe Gly Glu Arg Tyr Leu Ser Ser Ile Leu
385                 390                 395                 400

Phe Gln Ser Ile Arg Glu Glu Cys Glu Lys Leu Gln Pro Glu Pro
                405                 410                 415
```

<210> SEQ ID NO 65
<211> LENGTH: 383
<212> TYPE: PRT
<213> ORGANISM: Spinacia oleracea

<400> SEQUENCE: 65

```
Met Ala Ser Leu Val Asn Asn Ala Tyr Ala Ala Ile Arg Thr Ser Lys
  1               5                  10                  15

Leu Glu Leu Arg Glu Val Lys Asn Leu Ala Asn Phe Arg Val Gly Pro
             20                  25                  30

Pro Ser Ser Leu Ser Cys Asn Asn Phe Lys Lys Val Ser Ser Ser Pro
         35                  40                  45

Ile Thr Cys Lys Ala Val Ser Leu Ser Pro Pro Ser Thr Ile Glu Gly
     50                  55                  60

Leu Asn Ile Ala Glu Asp Val Ser Gln Leu Ile Gly Lys Thr Pro Met
 65                  70                  75                  80

Val Tyr Leu Asn Asn Val Ser Lys Gly Ser Val Ala Asn Ile Ala Ala
                 85                  90                  95

Lys Leu Glu Ser Met Glu Pro Cys Cys Ser Val Lys Asp Arg Ile Gly
            100                 105                 110

Tyr Ser Met Ile Asp Asp Ala Glu Gln Lys Gly Val Ile Thr Pro Gly
        115                 120                 125

Lys Thr Thr Leu Val Glu Pro Thr Ser Gly Asn Thr Gly Ile Gly Leu
    130                 135                 140

Ala Phe Ile Ala Ala Ala Arg Gly Tyr Lys Ile Thr Leu Thr Met Pro
145                 150                 155                 160

Ala Ser Met Ser Met Glu Arg Arg Val Ile Leu Lys Ala Phe Gly Ala
                165                 170                 175

Glu Leu Val Leu Thr Asp Pro Ala Lys Gly Met Lys Gly Ala Val Glu
            180                 185                 190

Lys Ala Glu Glu Ile Leu Lys Lys Thr Pro Asp Ser Tyr Met Leu Gln
        195                 200                 205

Gln Phe Asp Asn Pro Ala Asn Pro Lys Ile His Tyr Glu Thr Thr Gly
    210                 215                 220

Pro Glu Ile Trp Glu Asp Thr Lys Gly Lys Val Asp Ile Phe Val Ala
225                 230                 235                 240

Gly Ile Gly Thr Gly Gly Thr Ile Ser Gly Val Gly Arg Tyr Leu Lys
                245                 250                 255

Glu Arg Asn Pro Gly Val Gln Val Ile Gly Ile Glu Pro Thr Glu Ser
            260                 265                 270

Asn Ile Leu Ser Gly Gly Lys Pro Gly Pro His Lys Ile Gln Gly Leu
        275                 280                 285

Gly Ala Gly Phe Val Pro Ser Asn Leu Asp Leu Gly Val Met Asp Glu
    290                 295                 300

Val Ile Glu Val Ser Ser Glu Glu Ala Val Glu Met Ala Lys Gln Leu
305                 310                 315                 320

Ala Met Lys Glu Gly Leu Leu Val Gly Ile Ser Ser Gly Ala Ala Ala
                325                 330                 335

Ala Ala Ala Val Arg Ile Gly Lys Arg Pro Glu Asn Ala Gly Lys Leu
            340                 345                 350

Ile Ala Val Val Phe Pro Ser Phe Gly Glu Arg Tyr Leu Ser Ser Ile
        355                 360                 365

Leu Phe Gln Ser Ile Arg Glu Glu Cys Glu Asn Met Lys Pro Glu
    370                 375                 380
```

```
<210> SEQ ID NO 66
<211> LENGTH: 386
<212> TYPE: PRT
<213> ORGANISM: Solanum tuberosum

<400> SEQUENCE: 66

Met Ala Ser Phe Ile Asn Asn Pro Leu Thr Ser Leu Cys Asn Thr Lys
  1               5                  10                  15

Ser Glu Arg Asn Asn Leu Phe Lys Ile Ser Leu Tyr Glu Ala Gln Ser
             20                  25                  30

Leu Gly Phe Ser Lys Leu Asn Gly Ser Arg Lys Val Ala Phe Pro Ser
         35                  40                  45

Val Val Cys Lys Ala Val Ser Val Pro Thr Lys Ser Ser Thr Glu Ile
     50                  55                  60

Glu Gly Leu Asn Ile Ala Glu Asp Val Thr Gln Leu Ile Gly Asn Thr
 65                  70                  75                  80

Pro Met Val Tyr Leu Asn Thr Ile Ala Lys Gly Cys Val Ala Asn Ile
                 85                  90                  95

Ala Ala Lys Leu Glu Ile Met Glu Pro Cys Cys Ser Val Lys Asp Arg
            100                 105                 110

Ile Gly Phe Ser Met Ile Val Asp Ala Glu Glu Lys Gly Leu Ile Ser
        115                 120                 125

Pro Gly Lys Thr Val Leu Val Glu Pro Thr Ser Gly Asn Thr Gly Ile
    130                 135                 140

Gly Leu Ala Phe Ile Ala Ala Ser Arg Gly Tyr Lys Leu Ile Leu Thr
145                 150                 155                 160

Met Pro Ala Ser Met Ser Leu Glu Arg Arg Val Ile Leu Lys Ala Phe
                165                 170                 175

Gly Ala Glu Leu Val Leu Thr Asp Pro Ala Lys Gly Met Lys Gly Ala
            180                 185                 190

Val Ser Lys Ala Glu Glu Ile Leu Asn Asn Thr Pro Asp Ala Tyr Ile
        195                 200                 205

Leu Gln Gln Phe Asp Asn Pro Ala Asn Pro Lys Ile His Tyr Glu Thr
    210                 215                 220

Thr Gly Pro Glu Ile Trp Glu Asp Thr Lys Gly Lys Ile Asp Ile Leu
225                 230                 235                 240

Val Ala Gly Ile Gly Thr Gly Gly Thr Ile Thr Gly Thr Gly Arg Phe
                245                 250                 255

Leu Lys Glu Gln Asn Pro Asn Ile Lys Ile Ile Gly Val Glu Pro Thr
            260                 265                 270

Glu Ser Asn Val Leu Ser Gly Gly Lys Pro Gly Pro His Lys Ile Gln
        275                 280                 285

Gly Ile Gly Ala Gly Phe Ile Pro Gly Asn Leu Asp Gln Asp Val Met
    290                 295                 300

Asp Glu Val Ile Glu Ile Ser Ser Asp Glu Ala Val Glu Thr Ala Arg
305                 310                 315                 320

Thr Leu Ala Leu Gln Glu Gly Leu Leu Val Gly Ile Ser Ser Gly Ala
                325                 330                 335

Ala Ala Leu Ala Ala Ile Gln Val Gly Lys Arg Pro Glu Asn Ala Gly
            340                 345                 350

Lys Leu Ile Gly Val Val Phe Pro Ser Tyr Gly Glu Arg Tyr Leu Ser
        355                 360                 365

Ser Ile Leu Phe Gln Ser Ile Arg Glu Glu Cys Glu Lys Met Lys Pro
    370                 375                 380
```

Glu Leu
385

<210> SEQ ID NO 67
<211> LENGTH: 1581
<212> TYPE: DNA
<213> ORGANISM: Zea mays

<400> SEQUENCE: 67
ggccgtggct tactggcttc cacccacagc cttcgcactt ccctccttcc tcgcaaatgg 60
ccgtcgccgt ccccaacgct cccggccgcc tcttccttct ccaatccacc ccgttcccga 120
accctagcag ctcggcatcc gccgctcgag cccaatcctt ccgcgtacca cccctccgcc 180
tctcgctatt ccgacgcatg gctgggcgct cgctgacggt gatcgcaggc gcctccggcg 240
gctccgaacg agatctcagc gcctccgcag tctccgtgga ggccctggac tccgtcgcct 300
ccgattctga cttagagacg aaggagccca gtgtgtcgac gatgctgacg agcttcgaga 360
actcgttcga caagtatggg gctctgagca caccgctgta ccagaccgcc acctttaagc 420
agccttcagc tacagattat ggaacttatg attacactag aagtggtaac cctactcgtg 480
atgttctcca gagcctcatg gctaagcttg agaaagcaga tcaagcattc tgcttcacca 540
gcgggatggc ggcgttagct gcagtaaaac acctccttca ggctggacaa gaaatagttg 600
ctggtgagga catatatggt ggttctgatc gtctactctc gcaagttgtg ccaagaaatg 660
gaatagttgt aaaacgagta gatacaacga aaattagtga tgtggtgtct gcaattggac 720
cctccactag actggtttgg ctcgaaagtc ccacgaaccc tcgtcagcaa attactgaca 780
ttaagacaat ctcagagata gcgcattctc atggtgctct tgttttggtt gacaacagca 840
tcatgtctcc agtgctctcc cgtcctatag aactgggagc tgatatcgtg atgcactcgg 900
ctaccaaatt tatagcggga catagtgatc ttatggctgg aattcttgca gtgaagggtg 960
agagtttggc taaagaggta gggtttctgc aaaatgctga agggtcgggt ctggcacctt 1020
ttgactgctg gctttgcttg aggggaatca aaaccatggc tctgcgggtg gagaaacaac 1080
aggctaatgc ccagaagatt gctgaattcc tggcgtctca cccgagggtc aagcaagtaa 1140
actacgctgg gcttcctgac catcctgggc gagctttaca ctattcccag gcaaagggag 1200
cgggctctgt tctcagtttt ctcaccggct cactggccct ctcaaagcac gtcgtggaga 1260
ccaccaagta cttcagcgta acagtcagct tcgggagcgt gaagtccctc atcagcctgc 1320
cgtgcttcat gtcccacgca tcaatccctg cctcggtccg cgaggagcgt ggcctaaccg 1380
acgacctcgt ccggatatcg gtcggcatcg aggatgtcga ggacctcatc gccgatctgg 1440
accgcgcgct cagaactggc ccggtgtaga catcgccgat ccttaggtca tgtcaagcta 1500
tcttttgatg attcattggt tgactgcttg cgtgatgata ataatgggaa tgttgcttgg 1560
ataaaaaaaa aaaaaaaaaa a 1581

<210> SEQ ID NO 68
<211> LENGTH: 470
<212> TYPE: PRT
<213> ORGANISM: Zea mays

<400> SEQUENCE: 68

Met Ala Val Ala Val Pro Asn Ala Pro Gly Arg Leu Phe Leu Leu Gln
1 5 10 15

Ser Thr Pro Phe Pro Asn Pro Ser Ser Ser Ala Ser Ala Ala Arg Ala
20 25 30

```
Gln Ser Phe Arg Val Pro Pro Leu Arg Leu Ser Leu Phe Arg Arg Met
         35                  40                  45

Ala Gly Arg Ser Leu Thr Val Ile Ala Gly Ala Ser Gly Gly Ser Glu
     50                  55                  60

Arg Asp Leu Ser Ala Ser Ala Val Ser Val Glu Ala Leu Asp Ser Val
 65                  70                  75                  80

Ala Ser Asp Ser Asp Leu Glu Thr Lys Glu Pro Ser Val Ser Thr Met
                 85                  90                  95

Leu Thr Ser Phe Glu Asn Ser Phe Asp Lys Tyr Gly Ala Leu Ser Thr
            100                 105                 110

Pro Leu Tyr Gln Thr Ala Thr Phe Lys Gln Pro Ser Ala Thr Asp Tyr
        115                 120                 125

Gly Thr Tyr Asp Tyr Thr Arg Ser Gly Asn Pro Thr Arg Asp Val Leu
    130                 135                 140

Gln Ser Leu Met Ala Lys Leu Glu Lys Ala Asp Gln Ala Phe Cys Phe
145                 150                 155                 160

Thr Ser Gly Met Ala Ala Leu Ala Ala Val Lys His Leu Leu Gln Ala
                165                 170                 175

Gly Gln Glu Ile Val Ala Gly Glu Asp Ile Tyr Gly Gly Ser Asp Arg
            180                 185                 190

Leu Leu Ser Gln Val Val Pro Arg Asn Gly Ile Val Val Lys Arg Val
        195                 200                 205

Asp Thr Thr Lys Ile Ser Asp Val Val Ser Ala Ile Gly Pro Ser Thr
    210                 215                 220

Arg Leu Val Trp Leu Glu Ser Pro Thr Asn Pro Arg Gln Gln Ile Thr
225                 230                 235                 240

Asp Ile Lys Thr Ile Ser Glu Ile Ala His Ser His Gly Ala Leu Val
                245                 250                 255

Leu Val Asp Asn Ser Ile Met Ser Pro Val Leu Ser Arg Pro Ile Glu
            260                 265                 270

Leu Gly Ala Asp Ile Val Met His Ser Ala Thr Lys Phe Ile Ala Gly
        275                 280                 285

His Ser Asp Leu Met Ala Gly Ile Leu Ala Val Lys Gly Glu Ser Leu
    290                 295                 300

Ala Lys Glu Val Gly Phe Leu Gln Asn Ala Glu Gly Ser Gly Leu Ala
305                 310                 315                 320

Pro Phe Asp Cys Trp Leu Cys Leu Arg Gly Ile Lys Thr Met Ala Leu
                325                 330                 335

Arg Val Glu Lys Gln Gln Ala Asn Ala Gln Lys Ile Ala Glu Phe Leu
            340                 345                 350

Ala Ser His Pro Arg Val Lys Gln Val Asn Tyr Ala Gly Leu Pro Asp
        355                 360                 365

His Pro Gly Arg Ala Leu His Tyr Ser Gln Ala Lys Gly Ala Gly Ser
    370                 375                 380

Val Leu Ser Phe Leu Thr Gly Ser Leu Ala Leu Ser Lys His Val Val
385                 390                 395                 400

Glu Thr Thr Lys Tyr Phe Ser Val Thr Val Ser Phe Gly Ser Val Lys
                405                 410                 415

Ser Leu Ile Ser Leu Pro Cys Phe Met Ser His Ala Ser Ile Pro Ala
            420                 425                 430

Ser Val Arg Glu Glu Arg Gly Leu Thr Asp Asp Leu Val Arg Ile Ser
        435                 440                 445
```

-continued

```
Val Gly Ile Glu Asp Val Glu Asp Leu Ile Ala Asp Leu Asp Arg Ala
    450                 455                 460

Leu Arg Thr Gly Pro Val
465                 470
```

<210> SEQ ID NO 69
<211> LENGTH: 1685
<212> TYPE: DNA
<213> ORGANISM: Oryza sativa

<400> SEQUENCE: 69

```
aggcaaccat gagcgccgcc gccgccgccg ccgccgccgc cgcaatcccc acctctctcg     60
gccgcctctt ccacctccgc cccaccccga accccctcccg gaaccttagc ggcagctcag    120
cgcaacccct cctccgcctc agctaccacc cacgcctcac gctctctcgc cgcatggagg    180
cgccggcggc gatcgccgac tcccacggcg gcggcgacct gagcgcgtcc gcggtcggcg    240
cggaggcgct gggcgccgtc gccgctccgg atttcgatgt ggagatgaag gagcctagcg    300
tggcgacgat actgacgagc ttcgagaact cgttcgatgg gttcgggtct atgagcacgc    360
cgctgtacca gacggccacg tttaagcagc cttcagcaac cgataatgga ccttatgatt    420
acactagaag tggtaaccct acacgtgatg ttctccaaag ccttatggct aagcttgaga    480
aggcggatca ggcattctgc ttcaccagtg ggatggcagc actagctgca gtaacacacc    540
tccttaagtc tggacaagaa atagttgctg gagaggacat atatggtggc tcagaccgtc    600
tgctctcaca agttgccccg agacatggga ttgtagtaaa acgaattgat acaaccaaaa    660
ttagtgaggt aacttctgca attgggccct tgactaaact agtatggctt gaaagtccca    720
ccaatccccg tctacaaatt actgatataa agaaaatagc agagatagct cattaccatg    780
gtgctcttgt tttagtagac aacagcatca tgtctcctgt gctctcccgt cctctagaac    840
ttggagcaga tattgttatg cactcagcaa ccaaatttat agctggacat agcgatctta    900
tggctggaat tcttgcggtg aagggtgaaa gcagcttggc taaagagatt gcatttctac    960
aaaatgctga aggatcaggt ttggcaccat ttgattgctg gctttgtttg agaggaatca   1020
aaaccatggc tttgcgggtg gagaagcagc aggctaatgc tcagaagatt gctgaatttc   1080
tagcttctca tccaagagta aagaaagtga actatgcagg acttcctgat catcctggac   1140
gatctctaca ctattcccag gcaaagggag cgggttcagt tctcagtttc ctaactggtt   1200
cattagctct ctcaaaacat gttgttgaga ccacaaagta cttcaatgta acagttagct   1260
ttggaagtgt gaaatcgctc attagcctgc catgcttcat gtcacacgcc agcatccctt   1320
ctgcggttcg cgaggagcgc ggcctgacag acgatctagt caggatatcg gttggaattg   1380
aggatgccga cgacctcata gcggatcttg atcatgctct ccggtctggt ccagcttaga   1440
gcctgtgaat tctgtgccct tcctgttcgt tagggatgta gatgtggtca tgtgggtgct   1500
atctgtgtgg gtgattgatt cattggtcaa ctcaataagc tgctgtgtca tcgagggaat   1560
aaagacaatc tatcccaaat tttttaacac catatggtga ccaactgacc atgatatggt   1620
cttaatcaat tgatatttat agaaggtttc tttgaactgc aaaaaaaaaa aaaaaaaaaa   1680
aaaaa                                                              1685
```

<210> SEQ ID NO 70
<211> LENGTH: 476
<212> TYPE: PRT
<213> ORGANISM: Oryza sativa

<400> SEQUENCE: 70

-continued

```
Met Ser Ala Ala Ala Ala Ala Ala Ala Ala Ala Ala Ile Pro Thr Ser
  1               5                  10                  15

Leu Gly Arg Leu Phe His Leu Arg Pro Thr Pro Asn Pro Ser Arg Asn
             20                  25                  30

Leu Ser Gly Ser Ser Ala Gln Pro Leu Leu Arg Leu Ser Tyr His Pro
         35                  40                  45

Arg Leu Thr Leu Ser Arg Arg Met Glu Ala Pro Ala Ala Ile Ala Asp
     50                  55                  60

Ser His Gly Gly Gly Asp Leu Ser Ala Ser Ala Val Gly Ala Glu Ala
 65                  70                  75                  80

Leu Gly Ala Val Ala Ala Pro Asp Phe Asp Val Glu Met Lys Glu Pro
                 85                  90                  95

Ser Val Ala Thr Ile Leu Thr Ser Phe Glu Asn Ser Phe Asp Gly Phe
            100                 105                 110

Gly Ser Met Ser Thr Pro Leu Tyr Gln Thr Ala Thr Phe Lys Gln Pro
        115                 120                 125

Ser Ala Thr Asp Asn Gly Pro Tyr Asp Tyr Thr Arg Ser Gly Asn Pro
    130                 135                 140

Thr Arg Asp Val Leu Gln Ser Leu Met Ala Lys Leu Glu Lys Ala Asp
145                 150                 155                 160

Gln Ala Phe Cys Phe Thr Ser Gly Met Ala Ala Leu Ala Ala Val Thr
                165                 170                 175

His Leu Leu Lys Ser Gly Gln Glu Ile Val Ala Gly Glu Asp Ile Tyr
            180                 185                 190

Gly Gly Ser Asp Arg Leu Leu Ser Gln Val Ala Pro Arg His Gly Ile
        195                 200                 205

Val Val Lys Arg Ile Asp Thr Thr Lys Ile Ser Glu Val Thr Ser Ala
    210                 215                 220

Ile Gly Pro Leu Thr Lys Leu Val Trp Leu Glu Ser Pro Thr Asn Pro
225                 230                 235                 240

Arg Leu Gln Ile Thr Asp Ile Lys Lys Ile Ala Glu Ile Ala His Tyr
                245                 250                 255

His Gly Ala Leu Val Leu Val Asp Asn Ser Ile Met Ser Pro Val Leu
            260                 265                 270

Ser Arg Pro Leu Glu Leu Gly Ala Asp Ile Val Met His Ser Ala Thr
        275                 280                 285

Lys Phe Ile Ala Gly His Ser Asp Leu Met Ala Gly Ile Leu Ala Val
    290                 295                 300

Lys Gly Glu Ser Ser Leu Ala Lys Glu Ile Ala Phe Leu Gln Asn Ala
305                 310                 315                 320

Glu Gly Ser Gly Leu Ala Pro Phe Asp Cys Trp Leu Cys Leu Arg Gly
                325                 330                 335

Ile Lys Thr Met Ala Leu Arg Val Glu Lys Gln Gln Ala Asn Ala Gln
            340                 345                 350

Lys Ile Ala Glu Phe Leu Ala Ser His Pro Arg Val Lys Lys Val Asn
        355                 360                 365

Tyr Ala Gly Leu Pro Asp His Pro Gly Arg Ser Leu His Tyr Ser Gln
    370                 375                 380

Ala Lys Gly Ala Gly Ser Val Leu Ser Phe Leu Thr Gly Ser Leu Ala
385                 390                 395                 400

Leu Ser Lys His Val Val Glu Thr Thr Lys Tyr Phe Asn Val Thr Val
                405                 410                 415
```

-continued

```
Ser Phe Gly Ser Val Lys Ser Leu Ile Ser Leu Pro Cys Phe Met Ser
            420                 425                 430

His Ala Ser Ile Pro Ser Ala Val Arg Glu Glu Arg Gly Leu Thr Asp
        435                 440                 445

Asp Leu Val Arg Ile Ser Val Gly Ile Glu Asp Ala Asp Asp Leu Ile
    450                 455                 460

Ala Asp Leu Asp His Ala Leu Arg Ser Gly Pro Ala
465                 470                 475


<210> SEQ ID NO 71
<211> LENGTH: 1699
<212> TYPE: DNA
<213> ORGANISM: Triticum aestivum

<400> SEQUENCE: 71

gcacgagagc gtggccacga tactgaccag cttcgagaac tcgttcgaca agtatggggc     60

tctcagcacg ccgctgtacc agacggccac cttcaagcag ccttcagcaa ccgttaatgg    120

agcttatgat tatactagaa gtggcaaccc tactcgtgat gttctccaga gccttatggc    180

taagctcgag aaggcagacc aagcattctg cttcactagt gggatggcat cactggctgc    240

agtaacacac ctccttcagg ctggacaaga aatagttgct ggagaggaca tatatggtgg    300

ctctgatcgt ctgctctcac aagttgtccc aagaaatgga attgtagtaa aacgggtcga    360

tacaactaaa attaacgacg tgactgctgc aatcggaccc ttgactagac tagtttggct    420

tgaaagtccc accaatcctc gtcaacaaat tactgatata aagaaaatct cagagatagc    480

tcattctcat ggtgcacttg ttttggtgga caacagtatc atgtctccag tgctatcctg    540

gcctatagaa cttggagcag atattgtgat gcactcagct accaaattta tagctggaca    600

cagtgatctt atggctggaa ttcttgctgt aaagggtgaa agcttggcta aggagattgc    660

atttctacaa aacgctgaag gttctggttt ggcacctttt gattgttggc tttgcttgag    720

agggatcaaa accatggcct tacgggtgga aaagcaacag gataatgccc agaagattgc    780

tgaattctta gcttctcatc caagggtcaa gcaagtgaat tatgctggac ttcctgatca    840

tcctggccga tctttacact actctcaggc aaagggagcg ggctctgtcc tcagtttcca    900

aactggttca ttgtctctct caaagcatgt tgttgagaca accaagtact tcaacgtaac    960

agttagcttc ggaagtgtga agtcactcat aagcttgccc tgcttcatgt cgcacgcgag   1020

catcccttcc tcggtgcgag aggagcgtgg gttgactgat gatctagtac ggatatcggt   1080

gggtattgag gatgtggatg acctcatagc tgatcttgat tacgcgctca ggtccggtcc   1140

agcatagatc atacaaaatc tggactatgg cgcttcgggt tctagttaat caagttgtag   1200

atgtgatatg cattggtgat tcatttgtta agctgcaaca gtaataataa acttctgcac   1260

gagtattttc tgaaatgacg agcccacggt tgtatgtgtt gttcctcata ggcttcaaca   1320

gaaaaaccct gaggccaact gacaagtagc aacattcata aacttcacaa catcgatact   1380

tggttctgcc catgttcatt tttcttggct gccattgtga cggctttgta gctcaagtag   1440

gaaggagtga catggccgtt ggttgatggg gagaaaagga gttggttcgt cggatcgatc   1500

cgtgtaggcg cttgtgtatt ttgtatatgg tgtttttcgt ctgtgcaggt gagtctgtgt   1560

atacatctgg agactggatt attcatggtc attggtgtgg cggtgaagaa taatgtgacg   1620

attcttttgt agtgtatcta agaactgtga tgttcttgtg caaaaaaaaa aaaaaaaaaa   1680

aaaaaaaaaa aaaaaaaaa                                                1699
```

```
<210> SEQ ID NO 72
<211> LENGTH: 381
<212> TYPE: PRT
<213> ORGANISM: Triticum aestivum

<400> SEQUENCE: 72

His Glu Ser Val Ala Thr Ile Leu Thr Ser Phe Glu Asn Ser Phe Asp
  1               5                  10                  15

Lys Tyr Gly Ala Leu Ser Thr Pro Leu Tyr Gln Thr Ala Thr Phe Lys
             20                  25                  30

Gln Pro Ser Ala Thr Val Asn Gly Ala Tyr Asp Tyr Thr Arg Ser Gly
         35                  40                  45

Asn Pro Thr Arg Asp Val Leu Gln Ser Leu Met Ala Lys Leu Glu Lys
     50                  55                  60

Ala Asp Gln Ala Phe Cys Phe Thr Ser Gly Met Ala Ser Leu Ala Ala
 65                  70                  75                  80

Val Thr His Leu Leu Gln Ala Gly Gln Glu Ile Val Ala Gly Glu Asp
                 85                  90                  95

Ile Tyr Gly Gly Ser Asp Arg Leu Leu Ser Gln Val Val Pro Arg Asn
            100                 105                 110

Gly Ile Val Val Lys Arg Val Asp Thr Thr Lys Ile Asn Asp Val Thr
        115                 120                 125

Ala Ala Ile Gly Pro Leu Thr Arg Leu Val Trp Leu Glu Ser Pro Thr
    130                 135                 140

Asn Pro Arg Gln Gln Ile Thr Asp Ile Lys Lys Ile Ser Glu Ile Ala
145                 150                 155                 160

His Ser His Gly Ala Leu Val Leu Val Asp Asn Ser Ile Met Ser Pro
                165                 170                 175

Val Leu Ser Trp Pro Ile Glu Leu Gly Ala Asp Ile Val Met His Ser
            180                 185                 190

Ala Thr Lys Phe Ile Ala Gly His Ser Asp Leu Met Ala Gly Ile Leu
        195                 200                 205

Ala Val Lys Gly Glu Ser Leu Ala Lys Glu Ile Ala Phe Leu Gln Asn
    210                 215                 220

Ala Glu Gly Ser Gly Leu Ala Pro Phe Asp Cys Trp Leu Cys Leu Arg
225                 230                 235                 240

Gly Ile Lys Thr Met Ala Leu Arg Val Glu Lys Gln Gln Asp Asn Ala
                245                 250                 255

Gln Lys Ile Ala Glu Phe Leu Ala Ser His Pro Arg Val Lys Gln Val
            260                 265                 270

Asn Tyr Ala Gly Leu Pro Asp His Pro Gly Arg Ser Leu His Tyr Ser
        275                 280                 285

Gln Ala Lys Gly Ala Gly Ser Val Leu Ser Phe Gln Thr Gly Ser Leu
    290                 295                 300

Ser Leu Ser Lys His Val Val Glu Thr Thr Lys Tyr Phe Asn Val Thr
305                 310                 315                 320

Val Ser Phe Gly Ser Val Lys Ser Leu Ile Ser Leu Pro Cys Phe Met
                325                 330                 335

Ser His Ala Ser Ile Pro Ser Ser Val Arg Glu Glu Arg Gly Leu Thr
            340                 345                 350

Asp Asp Leu Val Arg Ile Ser Val Gly Ile Glu Asp Val Asp Asp Leu
        355                 360                 365

Ile Ala Asp Leu Asp Tyr Ala Leu Arg Ser Gly Pro Ala
    370                 375                 380
```